United States Patent
Hakak et al.

(10) Patent No.: US 8,691,498 B2
(45) Date of Patent: Apr. 8, 2014

(54) METHODS OF SCREENING FOR A COMPOUND THAT REDUCES ATHEROGENESIS

(75) Inventors: Yaron Hakak, San Diego, CA (US); David J. Unett, San Diego, CA (US); Joel Gatlin, San Diego, CA (US); Chen W. Liaw, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 784 days.

(21) Appl. No.: 11/991,232

(22) PCT Filed: Aug. 29, 2006

(86) PCT No.: PCT/US2006/033651
§ 371 (c)(1),
(2), (4) Date: Oct. 7, 2009

(87) PCT Pub. No.: WO2007/027661
PCT Pub. Date: Mar. 8, 2007

(65) Prior Publication Data
US 2010/0331238 A1 Dec. 30, 2010

Related U.S. Application Data

(60) Provisional application No. 60/714,137, filed on Sep. 2, 2005.

(51) Int. Cl.
*C12Q 1/00* (2006.01)
*C12Q 1/68* (2006.01)
*C07K 14/705* (2006.01)

(52) U.S. Cl.
USPC .................................. 435/4; 435/6; 530/350

(58) Field of Classification Search
None
See application file for complete search history.

(56) References Cited

U.S. PATENT DOCUMENTS

| | | | |
|---|---|---|---|
| 2005/0089866 A1 | 4/2005 | Hinuma et al. | |
| 2005/0154029 A1 | 7/2005 | Unett et al. | |

FOREIGN PATENT DOCUMENTS

| | | | |
|---|---|---|---|
| WO | WO2005007111 A2 | | 1/2005 |
| WO | WO 2005/050225 | * | 6/2005 |
| WO | WO2005050225 A2 | | 6/2005 |

OTHER PUBLICATIONS

Perry, et al, 2010, The G-protein-coupled receptor, GPR84, is important for eye development in *Xenopus laevis*. Dev Dyn.; 239(11): 3024-3037.*
Wang et al., Medium-chain fatty acids as ligands for orphan G protein-coupled receptor GPR84. J. Biol. Chem. 281:34457-34464, 2006.*
Filizola, et al., "BUNDLE: a program for building the transmembrane domains of G-protein-coupled receptors", J. Comput. Aided Mol. Des., 1998, 12:111-8.
Gouldson, et al., "Domain swapping in G-protein coupled receptor dimers", Protein Eng., 1998, 11:1181-93.
Hebert, et al., "Structural and functional aspects of G protein-coupled receptor oligomerization", Biochem. Cell Biol., 1998, 76:1-11.
Inglese, et al., "Structure and mechanism of the G protein-coupled receptor kinases", J. Biol. Chem., 1993, 268:23735-8.
Jackson, "Structure and function of G protein coupled receptors", Pharmacol. Ther., 1991, 50:425-42.
Leung, et al., "Gonadotropin-releasing hormone receptor: gene structure, expression and regulation", Biol. Signals., 1996, 5:63-9.
Missale, et al., "Dopamine receptors: from structure to junction", Physiol. Rev., 1998, 78:189-225.
Ostrowski, et al., "Mutagenesis of the beta2-Adrenergic Receptor: How Structure Elucidates Function Annual Review of Pharmacology and Toxicology", 1992, 32:167-183.
Sealfon, et al., "Functional domains of the gonadotropin-releasing hormone receptor", Cell Mol. Neurobiol., 1995, 15:25-42.
Venkararaman, et al., "The G-protein coupled receptor, GPR84 regulates IL-4 production by T lymphocytes in response to CD3 crosslinking.", Immunology Letters 101 (2005) 144-153.
Wess, et al., "Identification of a small intracellular region of the muscarinic m3 receptor as a determinant of selective coupling to PI turnover", FEBS Letters, 1989, 258:133-6.
Wong, et al., "Chimeric muscarinic cholinergic: beta-adrenergic receptors that activate Gs in response to muscarinic agonists", J. Biol. Chem., 1990, 265:6219-24.
Yeagle, et al., "Structure of the G-protein-coupled receptor, rhodopsin: a domain approach", Biochem. Soc. Trans., 1998, 26:520-31.
Yousefi, et al., "Cloning and expression analysis of a novel G-protein-coupled receptor selectively expressed on granulocytes." Journal of Leukocyte Biology vol. 69, Jun. 200, pp. 1045-1052, 2001.

* cited by examiner

*Primary Examiner* — Ruixiang Li
(74) *Attorney, Agent, or Firm* — James S. Keddie; Bozicevic, Field & Francis, LLP

(57) ABSTRACT

The present invention relates to methods of using a G protein-coupled receptor (GPCR) to identify whether a candidate compound is a modulator of atherogenesis. In certain embodiments, the GPCR couples to Gi. In certain embodiments, the GPCR is human. Agonists of the invention are useful as therapeutic agents for the prevention or treatment of atherosclerosis and atherosclerotic disease, including coronary artery disease, myocardial infarction, peripheral arterial disease, and ischemic stroke. Agonists of the invention are additionally useful as therapeutic agents for the prevention or treatment of conditions related to MCP-1 expression, including but not limited to rheumatoid arthritis, Crohn's disease, and multiple sclerosis.

10 Claims, 17 Drawing Sheets

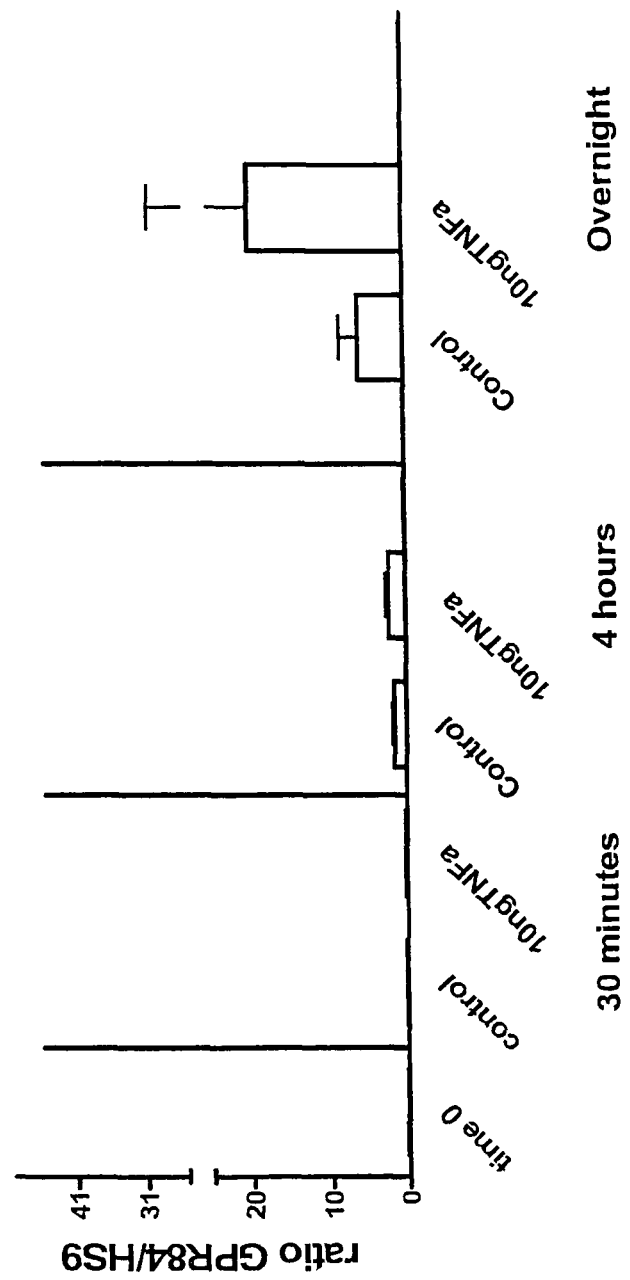
Figure 3A. TNFα Upregulates GPR84 Expression in Primary Adherent Human Monocytes

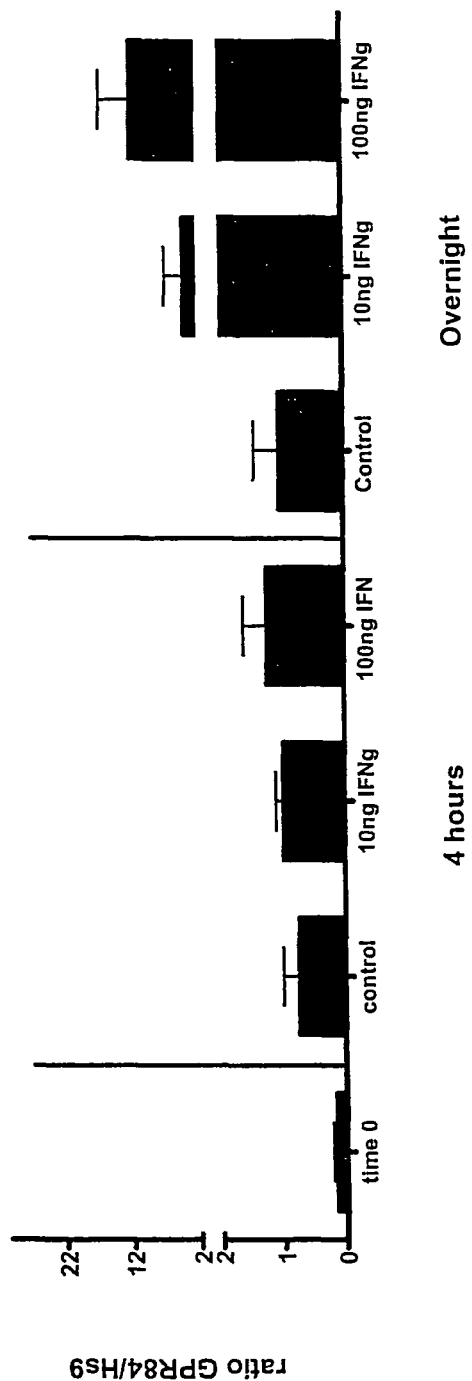
Figure 3B. IFNγ Upregulates GPR84 Expression in Primary Adherent Human Monocytes

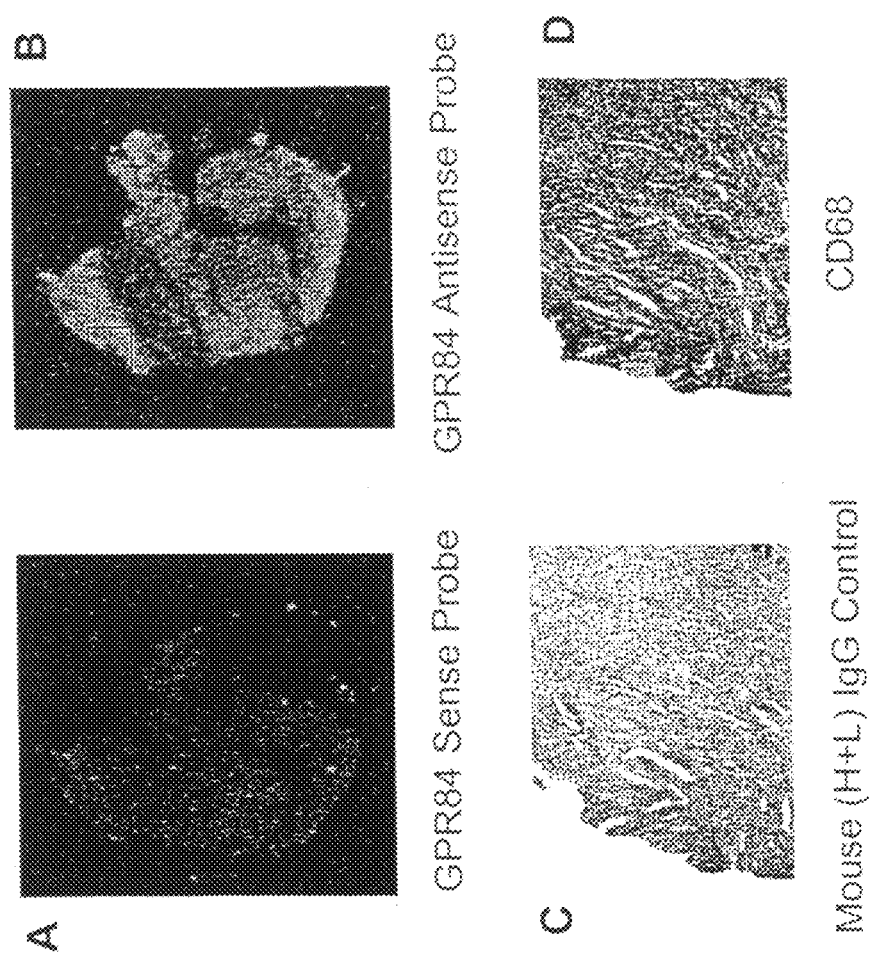

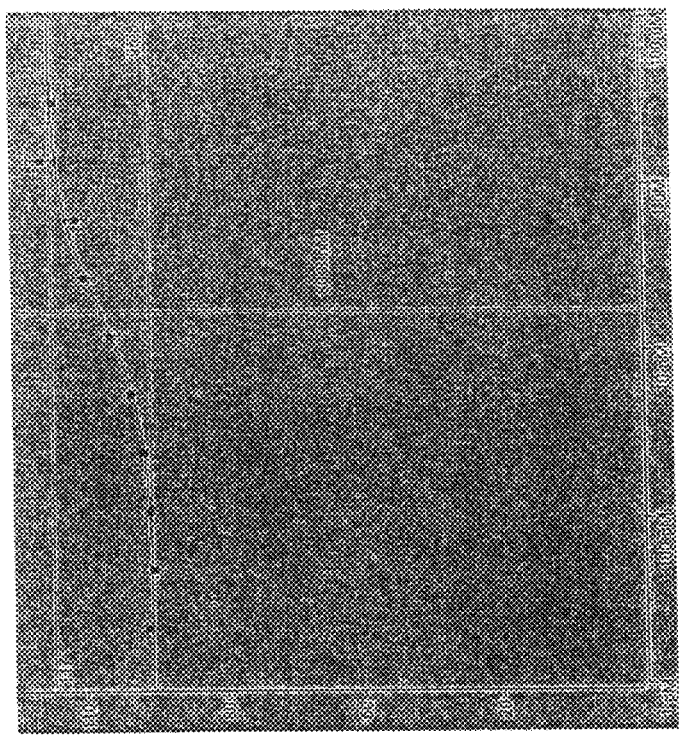

SEQUENCE LISTING

<160> NUMBER OF SEQ ID NOS: 23

<210> SEQ ID NO 1
<211> LENGTH: 1191
<212> TYPE: DNA
<213> ORGANISM: Homo Sapiens

<400> SEQUENCE: 1
atgtggaaca gctctgacgc caacttctcc tgctaccatg agtctgtgct gggctatcgt    60

```
tatgttgcag ttagctgggg ggtggtggtg gctgtgacag gcaccgtggg caatgtgctc      120
accctactgg ccttggccat ccagcccaag ctccgtaccc gattcaacct gctcatagcc      180
aacctcacac tggctgatct cctctactgc acgctccttc agcccttctc tgtggacacc      240
tacctccacc tgcactggcg caccggtgcc accttctgca gggtatttgg gctcctcctt      300
tttgcctcca attctgtctc catcctgacc ctctgcctca tcgcactggg acgctacctc      360
ctcattgccc accctaagct tttccccaa gttttcagtg ccaaggggat agtgctggca       420
ctggtgagca cctgggttgt gggcgtggcc agctttgctc ccctctggcc tatttatatc      480
ctggtacctg tagtctgcac ctgcagcttt gaccgcatcc gaggccggcc ttacaccacc      540
atcctcatgg gcatctactt tgtgcttggg ctcagcagtg ttggcatctt ctattgcctc      600
atccaccgcc aggtcaaacg agcagcacag gcactggacc aatacaagtt gcgacaggca      660
agcatccact ccaaccatgt ggccaggact gatgaggcca tgcctggtcg tttccaggag      720
ctggacagca ggttagcatc aggaggaccc agtgagggga tttcatctga gccagtcagt      780
gctgccacca cccagaccct ggaaggggac tcatcagaag tgggagacca gatcaacagc      840
aagagagcta agcagatggc agagaaaagc cctccagaag catctgccaa agcccagcca      900
attaaaggag ccagaagagc tccggattct tcatcggaat ttgggaaggt gactcgaatg      960
tgttttgctg tgttcctctg ctttgccctg agctacatcc ccttcttgct gctcaacatt     1020
ctggatgcca gagtccaggc tccccgggtg gtccacatgc ttgctgccaa cctcacctgg     1080
ctcaatggtt gcatcaaccc tgtgctctat gcagccatga accgccaatt ccgccaagca     1140
tatggctcca ttttaaaaag agggcccgg agtttccata ggctccatta g                1191
```

<210> SEQ ID NO 2
<211> LENGTH: 396
<212> TYPE: PRT
<213> ORGANISM: Homo Sapiens

<400> SEQUENCE: 2

```
Met Trp Asn Ser Ser Asp Ala Asn Phe Ser Cys Tyr His Glu Ser Val
1               5                   10                  15

Leu Gly Tyr Arg Tyr Val Ala Val Ser Trp Gly Val Val Ala Val
                20                  25                  30

Thr Gly Thr Val Gly Asn Val Leu Thr Leu Ala Leu Ala Ile Gln
            35                  40                  45

Pro Lys Leu Arg Thr Arg Phe Asn Leu Ile Ala Asn Leu Thr Leu
        50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Thr Phe Cys Arg Val Phe
                85                  90                  95

Gly Leu Leu Leu Phe Ala Ser Asn Ser Val Ser Ile Leu Thr Leu Cys
                100                 105                 110

Leu Ile Ala Leu Gly Arg Tyr Leu Leu Ile Ala His Pro Lys Leu Phe
            115                 120                 125

Pro Gln Val Phe Ser Ala Lys Gly Ile Val Leu Ala Leu Val Ser Thr
        130                 135                 140

Trp Val Val Gly Val Ala Ser Phe Ala Pro Leu Trp Pro Ile Tyr Ile
145                 150                 155                 160

Leu Val Pro Val Val Cys Thr Cys Ser Phe Asp Arg Ile Arg Gly Arg
                165                 170                 175
```

```
Pro Tyr Thr Thr Ile Leu Met Gly Ile Tyr Phe Val Leu Gly Leu Ser
            180                 185                 190

Ser Val Gly Ile Phe Tyr Cys Leu Ile His Arg Gln Val Lys Arg Ala
        195                 200                 205

Ala Gln Ala Leu Asp Gln Tyr Lys Leu Arg Gln Ala Ser Ile His Ser
    210                 215                 220

Asn His Val Ala Arg Thr Asp Glu Ala Met Pro Gly Arg Phe Gln Glu
225                 230                 235                 240

Leu Asp Ser Arg Leu Ala Ser Gly Gly Pro Ser Glu Gly Ile Ser Ser
                245                 250                 255

Glu Pro Val Ser Ala Ala Thr Thr Gln Thr Leu Glu Gly Asp Ser Ser
            260                 265                 270

Glu Val Gly Asp Gln Ile Asn Ser Lys Arg Ala Lys Gln Met Ala Glu
        275                 280                 285

Lys Ser Pro Pro Glu Ala Ser Ala Lys Ala Gln Pro Ile Lys Gly Ala
    290                 295                 300

Arg Arg Ala Pro Asp Ser Ser Glu Phe Gly Lys Val Thr Arg Met
305                 310                 315                 320

Cys Phe Ala Val Phe Leu Cys Phe Ala Leu Ser Tyr Ile Pro Phe Leu
                325                 330                 335

Leu Leu Asn Ile Leu Asp Ala Arg Val Gln Ala Pro Arg Val Val His
            340                 345                 350

Met Leu Ala Ala Asn Leu Thr Trp Leu Asn Gly Cys Ile Asn Pro Val
        355                 360                 365

Leu Tyr Ala Ala Met Asn Arg Gln Phe Arg Gln Ala Tyr Gly Ser Ile
    370                 375                 380

Leu Lys Arg Gly Pro Arg Ser Phe His Arg Leu His
385                 390                 395

<210> SEQ ID NO 3
<211> LENGTH: 1191
<212> TYPE: DNA
<213> ORGANISM: Mus Musculus

<400> SEQUENCE: 3
atgtggaaca gctcagatgc caacttctcc tgctaccatg agtctgtgtt gggctatcga      60
tactttgcaa ttatctgggg cgtggcagtg gctgtgacag gcacggtggg caatgtgctc     120
actctgctgg ccttggccat tcgtcccaag ctccgaaccc gcttcaacct gctcattgcc     180
aacctcaccc tggctgatct actctactgc acgtcctgc agccttctc cgtggacaca      240 tacctccacc tccattggcg taccggcgcg gtcttctgta gaatatttgg actcctcctc     300
tttacttcca attctgtctc catcctcacc ctctgtctca ttgctctagg acgctaccct      360
ctcattgccc accctaagct ctttcccag gttttcagtg ccaaggggat cgtgctggca      420
ctggtgggca gctgggttgt gggggtgacc agctttgccc ccctctggaa tgtttttgtc     480
ttggtgccag ttgtctgcac ctgcagcttt gaccgcatgc gaggccggcc ttacaccacc     540
atcctcatgg gcatctactt tgtgcttggg ctcagcagcg tgggcgtctt ctactgcctc     600
atccaccggc aagtgaagcg tgcggctcga gcactggacc aatacgggct gcatcaggcc     660
agcatccgct ctcatcaggt ggctgggaca caagaagcca tgcctggcca cttccaggag     720
ctagacagcg gggttgcctc aagagggccc agcgagggga tttcatctga gccagtcagt     780
gctgcgacca cgcagaccct ggaaggtgat cgtcagaag ctggggggcca gggcattaga      840 aaggcagctc aacagatcgc agagagaagc cttccagaag tgcatcgcaa gccccgggaa     900
```

```
actgcaggag ctcgcagagc cacagatgcc ccatcagagt tcgggaaggt gacccgtatg    960
tgcttcgcag tgttcctctg cttcgccctc agctacatcc ccttcctgtt gctcaacatt   1020
ctggacgcca ggggccgtgc tccacgagta gtgcacatgg tggctgccaa cctcacctgg   1080
ctcaacagct gcatcaaccc tgtgctctat gcagccatga accgccagtt cgccacgcg    1140 tatggctcca tcctgaaacg cgggccacag agtttccgcc ggttccatta a            1191
```

<210> SEQ ID NO 4
<211> LENGTH: 396
<212> TYPE: PRT
<213> ORGANISM: Mus Musculus

<400> SEQUENCE: 4

```
Met Trp Asn Ser Ser Asp Ala Asn Phe Ser Cys Tyr His Glu Ser Val
1               5                   10                  15

Leu Gly Tyr Arg Tyr Phe Ala Ile Ile Trp Gly Val Ala Val Ala Val
            20                  25                  30

Thr Gly Thr Val Gly Asn Val Leu Thr Leu Ala Leu Ala Ile Arg
        35                  40                  45

Pro Lys Leu Arg Thr Arg Phe Asn Leu Leu Ile Ala Asn Leu Thr Leu
50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Val Phe Cys Arg Ile Phe
                85                  90                  95

Gly Leu Leu Leu Phe Thr Ser Asn Ser Val Ser Ile Leu Thr Leu Cys
            100                 105                 110

Leu Ile Ala Leu Gly Arg Tyr Leu Leu Ile Ala His Pro Lys Leu Phe
        115                 120                 125

Pro Gln Val Phe Ser Ala Lys Gly Ile Val Leu Ala Leu Val Gly Ser
130                 135                 140

Trp Val Val Gly Val Thr Ser Phe Ala Pro Leu Trp Asn Val Phe Val
145                 150                 155                 160

Leu Val Pro Val Val Cys Thr Cys Ser Phe Asp Arg Met Arg Gly Arg
                165                 170                 175

Pro Tyr Thr Thr Ile Leu Met Gly Ile Tyr Phe Val Leu Gly Leu Ser
            180                 185                 190

Ser Val Gly Val Phe Tyr Cys Leu Ile His Arg Gln Val Lys Arg Ala
        195                 200                 205

Ala Arg Ala Leu Asp Gln Tyr Gly Leu His Gln Ala Ser Ile Arg Ser
210                 215                 220

His Gln Val Ala Gly Thr Gln Glu Ala Met Pro Gly His Phe Gln Glu
225                 230                 235                 240

Leu Asp Ser Gly Val Ala Ser Arg Gly Pro Ser Glu Gly Ile Ser Ser
                245                 250                 255

Glu Pro Val Ser Ala Ala Thr Gln Thr Leu Glu Gly Asp Ser Ser
            260                 265                 270

Glu Ala Gly Gly Gln Gly Ile Arg Lys Ala Ala Gln Ile Ala Glu
        275                 280                 285

Arg Ser Leu Pro Glu Val His Arg Lys Pro Arg Glu Thr Ala Gly Ala
290                 295                 300

Arg Arg Ala Thr Asp Ala Pro Ser Glu Phe Gly Lys Val Thr Arg Met
305                 310                 315                 320

Cys Phe Ala Val Phe Leu Cys Phe Ala Leu Ser Tyr Ile Pro Phe Leu
                325                 330                 335
```

Leu Leu Asn Ile Leu Asp Ala Arg Gly Arg Ala Pro Arg Val Val His
            340                 345                 350

Met Val Ala Ala Asn Leu Thr Trp Leu Asn Ser Cys Ile Asn Pro Val
            355                 360                 365

Leu Tyr Ala Ala Met Asn Arg Gln Phe Arg His Ala Tyr Gly Ser Ile
            370                 375                 380

Leu Lys Arg Gly Pro Gln Ser Phe Arg Arg Phe His
385                 390                 395

<210> SEQ ID NO 5
<211> LENGTH: 1191
<212> TYPE: DNA
<213> ORGANISM: Rattus Norvegicus

<400> SEQUENCE: 5
atgtggaaca gctcagatga caacttctcc tgctaccatg agtctgtatt gggctatcga      60
tactttgcag ttatctgggg catggtagtg gctgcaacag gcaccgtggg caatgtgctc     120
accctgttgg ccttggccat ccgtcccaaa ctccgaaccc gtttcaacct gctcattgcc     180
aacctcaccc tggctgatct actctactgc acgtcctgc agcctttctc cgtggacaca      240
tacctccacc tccattggcg caccggcgcc atcttctgta gaatattcgg actcctcctc     300
tttacttcca attctgtctc cattcttacc ctctgtctca ttgctctagg acgctacctt     360
ctcattgccc accctaagct cttttcccag ttttcagtg ccaaggggat cgtgctggca      420
ctagtgggca gctgggttgt gggggtgacc agctttgccc ccctctggaa tgtttatgtc     480
ttggtgccag ttgtctgcac ctgcagcttt gaccgcgtgc gaggccggcc ttacaccacc     540
atcctcatgg catcttctt tgtggttggg ctcagcagcg tgggcgtctt ctactgcctc      600
atccaccgcc aagtgaagcg tgcggctcga gcgctggaca aatatgggct gcaggaggcc     660
agcatgcgct cccatcaggt gtctgggaca catgaagctg tgccaggcca cttccaggag     720
ctagacagcg ggcttgcatc aagaggtccc agcgaaggga tttcatctga gccagtcagt     780
gctgcgacga cacagaccct ggaaggtgat tcgtcagaag cggggggacca gggcatgaga     840 aaggcagctc agcagatctc agagagaagc cttccagaag tgcatcgcaa gactggagga     900
gctgcaggag cacgcagagc cacggatgca ccatcggagt tcgggaaggt gacccgtatg     960
tgctttgcag tgttcctttg cttcgtcctc agctacatcc ctttcctgct gctcaacatt    1020
ctggacgcca ggggccgcgc tccacgagta gtgcatatgg ttgctgccaa cctcacctgg    1080
ctcaacagct gcatcaaccc tgtgctctat gcagccatga accgccagtt cgccaggct     1140 tatggctcca tcctgaaacg cgggccacag agtttccgac ggttccatta g            1191

<210> SEQ ID NO 6
<211> LENGTH: 396
<212> TYPE: PRT
<213> ORGANISM: Rattus Norvegicus

<400> SEQUENCE: 6

Met Trp Asn Ser Ser Asp Asp Asn Phe Ser Cys Tyr His Glu Ser Val
1               5                   10                  15

Leu Gly Tyr Arg Tyr Phe Ala Val Ile Trp Gly Met Val Val Ala Ala
            20                  25                  30

Thr Gly Thr Val Gly Asn Val Leu Thr Leu Leu Ala Leu Ala Ile Arg
            35                  40                  45

Pro Lys Leu Arg Thr Arg Phe Asn Leu Leu Ile Ala Asn Leu Thr Leu
50                  55                  60

-continued

```
Ala Asp Leu Leu Tyr Cys Thr Leu Leu Gln Pro Phe Ser Val Asp Thr
 65                  70                  75                  80

Tyr Leu His Leu His Trp Arg Thr Gly Ala Ile Phe Cys Arg Ile Phe
                 85                  90                  95

Gly Leu Leu Phe Thr Ser Asn Ser Val Ser Ile Leu Thr Leu Cys
            100                 105                 110

Leu Ile Ala Leu Gly Arg Tyr Leu Leu Ile Ala His Pro Lys Leu Phe
        115                 120                 125

Pro Gln Val Phe Ser Ala Lys Gly Ile Val Leu Ala Leu Val Gly Ser
    130                 135                 140

Trp Val Val Gly Val Thr Ser Phe Ala Pro Leu Trp Asn Val Tyr Val
145                 150                 155                 160

Leu Val Pro Val Val Cys Thr Cys Ser Phe Asp Arg Val Arg Gly Arg
                165                 170                 175

Pro Tyr Thr Thr Ile Leu Met Gly Ile Phe Val Val Gly Leu Ser
            180                 185                 190

Ser Val Gly Val Phe Tyr Cys Leu Ile His Arg Gln Val Lys Arg Ala
        195                 200                 205

Ala Arg Ala Leu Asp Lys Tyr Gly Leu Gln Glu Ala Ser Met Arg Ser
    210                 215                 220

His Gln Val Ser Gly Thr His Glu Ala Val Pro Gly His Phe Gln Glu
225                 230                 235                 240

Leu Asp Ser Gly Leu Ala Ser Arg Gly Pro Ser Glu Gly Ile Ser Ser
                245                 250                 255

Glu Pro Val Ser Ala Ala Thr Thr Gln Thr Leu Glu Gly Asp Ser Ser
            260                 265                 270

Glu Ala Gly Asp Gln Gly Met Arg Lys Ala Ala Gln Gln Ile Ser Glu
        275                 280                 285

Arg Ser Leu Pro Glu Val His Arg Lys Thr Gly Gly Ala Ala Gly Ala
    290                 295                 300

Arg Arg Ala Thr Asp Ala Pro Ser Glu Phe Gly Lys Val Thr Arg Met
305                 310                 315                 320

Cys Phe Ala Val Phe Leu Cys Phe Val Leu Ser Tyr Ile Pro Phe Leu
                325                 330                 335

Leu Leu Asn Ile Leu Asp Ala Arg Gly Arg Ala Pro Arg Val Val His
            340                 345                 350

Met Val Ala Ala Asn Leu Thr Trp Leu Asn Ser Cys Ile Asn Pro Val
        355                 360                 365

Leu Tyr Ala Ala Met Asn Arg Gln Phe Arg Gln Ala Tyr Gly Ser Ile
    370                 375                 380

Leu Lys Arg Gly Pro Gln Ser Phe Arg Arg Phe His
385                 390                 395

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
actaagcttc tatcatgtgg aacagc                                          26

<210> SEQ ID NO 8
<211> LENGTH: 18
<212> TYPE: DNA
```

<213> ORGANISM: Artificial
<220> FEATURE:
<223> OTHER INFORMATION: primer

<400> SEQUENCE: 8
aggagacagt cctgaatt                                                   18

<210> SEQ ID NO 9
<211> LENGTH: 6
<212> TYPE: PRT
<213> ORGANISM: Artificial
<220> FEATURE:
<223> OTHER INFORMATION: Synthetic peptide N-terminal of Gaq

<400> SEQUENCE: 9

Thr Leu Glu Ser Ile Met
1               5

<210> SEQ ID NO 10
<211> LENGTH: 5
<212> TYPE: PRT
<213> ORGANISM: Artificial
<220> FEATURE:
<223> OTHER INFORMATION: Synthetic peptide C-terminal of Gaq

<400> SEQUENCE: 10

Glu Tyr Asn Leu Val
1               5

<210> SEQ ID NO 11
<211> LENGTH: 5
<212> TYPE: PRT
<213> ORGANISM: Artificial
<220> FEATURE:
<223> OTHER INFORMATION: Synthetic peptide C-terminal of Gai

<400> SEQUENCE: 11

Asp Cys Gly Leu Phe
1               5

<210> SEQ ID NO 12
<211> LENGTH: 36
<212> TYPE: DNA
<213> ORGANISM: Artificial
<220> FEATURE:
<223> OTHER INFORMATION: primer

<400> SEQUENCE: 12
gatcaagctt ccatggcgtg ctgcctgagc gaggag                               36

<210> SEQ ID NO 13
<211> LENGTH: 53
<212> TYPE: DNA
<213> ORGANISM: Artificial
<220> FEATURE:
<223> OTHER INFORMATION: primer

<400> SEQUENCE: 13
gatcggatcc ttagaacagg ccgcagtcct tcaggttcag ctgcaggatg gtg            53

<210> SEQ ID NO 14
<211> LENGTH: 1062
<212> TYPE: DNA
<213> ORGANISM: Artificial
<220> FEATURE:
<223> OTHER INFORMATION: chimeric polynucleotide

<400> SEQUENCE: 14

-continued

```
atggcgtgct gcctgagcga ggaggccaag gaagcccgga ggatcaacga cgagatcgag    60
cggcagctgc gcagggacaa gcgcgacgcc cgccgggagc tcaagctgct gctgctgggg   120
acagggagga gtggcaagtc gaccttcatc aagcagatga ggatcatcca cgggtcgggc   180
tactctgacg aagacaagcg cggcttcacc aagctggtgt atcagaacat cttcacggcc   240
atgcaggcca tgatcagagc gatggacaca ctcaagatcc catacaagta tgaacacaat   300
aaggctcatg cacaattggt tcgagaggtt gatgtggaga aggtgtctgc ttttgacgtc   360
cccgactacg cggcaataaa gagcttgtgg aatgatcctg gaatccagga gtgctacgac   420
agacgacggg aatatcagtt atctgactct accaaatact atctgaatga cttggaccgt   480
gtagccgacc cttcctatct gcctacacaa caagacgtgc ttagagttcg agtccccact   540
acagggatca tcgaataccc ctttgactta caaagtgtca ttttcagaat ggtcgatgta   600
gggggccaaa ggtcagagag aagaaaatgg atccactgct ttgaaaatgt cacctccatc   660
atgtttctag tagcgcttag cgaatatgat caagttcttg tggagtcaga caatgagaac   720
cgcatggagg agagcaaagc actctttaga acaattatca cctaccccctg gttccagaac   780 tcctctgtga ttctgttctt aaacaagaaa gatcttctag aggagaaaat catgtattcc   840
cacctagtcg actacttccc agaatatgat ggaccccaga gagatgccca ggcagctcga   900
gaattcatcc tgaaaatgtt cgtggacctg aaccccgaca gtgacaaaat catctactcc   960
cacttcacgt gcgccacaga taccgagaac atccgcttcg tctttgcagc cgtcaaggac  1020
accatcctgc agctgaacct gaaggactgc ggcctgttct aa                      1062
```

<210> SEQ ID NO 15
<211> LENGTH: 353
<212> TYPE: PRT
<213> ORGANISM: Artificial
<220> FEATURE:
<223> OTHER INFORMATION: chimeric polypeptide

<400> SEQUENCE: 15

```
Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175
```

-continued

```
Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Asp Cys Gly Leu
            340                 345                 350

Phe
```

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16 tccttttttgc ctccaattct gt          22

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
gcgtcccagt gcgatgag                18

<210> SEQ ID NO 18
<211> LENGTH: 16
<212> TYPE: DNA
<213> ORGANISM: Artificial
<220> FEATURE:
<223> OTHER INFORMATION: primer

<400> SEQUENCE: 18
tccatcctga ccctct                  16

<210> SEQ ID NO 19
<211> LENGTH: 1227
<212> TYPE: DNA
<213> ORGANISM: Artificial
<220> FEATURE:
<223> OTHER INFORMATION: chimeric polynucleotide

<400> SEQUENCE: 19

```
atgtacccat acgacgtccc agactacgct ggaagcttgt ggaacagctc tgacgccaac    60
ttctcctgct accatgagtc tgtgctgggc tatcgttatg ttgcagttag ctgggggtg    120
gtggtggctg tgacaggcac cgtgggcaat gtgctcaccc tactggcctt ggccatccag   180
cccaagctcc gtacccgatt caacctgctc atagccaacc tcacactggc tgatctcctc   240
tactgcacgc tccttcagcc cttctctgtg gacacctacc tccacctgca ctggcgcacc   300
ggtgccacct tctgcagggt atttgggctc ctccttttg cctccaattc tgtctccatc   360
ctgaccctct gcctcatcgc actgggacgc tacctcctca ttgcccaccc taagctttt    420
ccccaagttt tcagtgccaa ggggatagtg ctggcactgg tgagcacctg ggttgtgggc   480
gtggccagct ttgctcccct ctggcctatt tatatcctgg tacctgtagt ctgcacctgc   540
agctttgacc gcatccgagg ccggccttac accaccatcc tcatgggcat ctactttgtg   600
cttgggctca gcagtgttgg catcttctat tgcctcatcc accgccaggt caaacgagca   660
gcacaggcac tggaccaata caagttgcga caggcaagca tccactccaa ccatgtggcc   720
aggactgatg aggccatgcc tggtcgtttc caggagctgg acagcaggtt agcatcagga   780
ggacccagtg aggggatttc atctgagcca gtcagtgctg ccaccaccca gaccctggaa   840
ggggactcat cagaagtggg agaccagatc aacagcaaga gagctaagca gatggcagag   900
aaaagccctc cagaagcatc tgccaaagcc cagccaatta aggagccag aagagctccg    960
gattcttcat cggaatttgg gaaggtgact cgaatgtgtt ttgctgtgtt cctctgctt   1020
gccctgagct acatcccctt cttgctgctc aacattctgg atgccagagt ccaggctccc  1080
cgggtggtcc acatgcttgc tgccaacctc acctggctca atggttgcat caaccctgtg  1140
ctctatgcag ccatgaaccg ccaattccgc caagcatatg ctccattttt aaaaagaggg  1200
ccccggagtt tccataggct ccattag                                      1227
```

<210> SEQ ID NO 20
<211> LENGTH: 408
<212> TYPE: PRT
<213> ORGANISM: Artificial
<220> FEATURE:
<223> OTHER INFORMATION: chimeric polypeptide

<400> SEQUENCE: 20

Met Tyr Pro Tyr Asp Val Pro Asp Tyr Ala Gly Ser Leu Trp Asn Ser
1               5                   10                  15

Ser Asp Ala Asn Phe Ser Cys Tyr His Glu Ser Val Leu Gly Tyr Arg
            20                  25                  30

Tyr Val Ala Val Ser Trp Gly Val Val Ala Val Thr Gly Thr Val
        35                  40                  45

Gly Asn Val Leu Thr Leu Leu Ala Leu Ala Ile Gln Pro Lys Leu Arg
    50                  55                  60

Thr Arg Phe Asn Leu Leu Ile Ala Asn Leu Thr Leu Ala Asp Leu Leu
65                  70                  75                  80

Tyr Cys Thr Leu Leu Gln Pro Phe Ser Val Asp Thr Tyr Leu His Leu
                85                  90                  95

His Trp Arg Thr Gly Ala Thr Phe Cys Arg Val Phe Gly Leu Leu Leu
            100                 105                 110

Phe Ala Ser Asn Ser Val Ser Ile Leu Thr Leu Cys Leu Ile Ala Leu
        115                 120                 125

Gly Arg Tyr Leu Leu Ile Ala His Pro Lys Leu Phe Pro Gln Val Phe
    130                 135                 140

-continued

```
Ser Ala Lys Gly Ile Val Leu Ala Leu Val Ser Thr Trp Val Gly
145                 150                 155                 160

Val Ala Ser Phe Ala Pro Leu Trp Pro Ile Tyr Ile Leu Val Pro Val
            165                 170                 175

Val Cys Thr Cys Ser Phe Asp Arg Ile Arg Gly Arg Pro Tyr Thr Thr
        180                 185                 190

Ile Leu Met Gly Ile Tyr Phe Val Leu Gly Leu Ser Ser Val Gly Ile
            195                 200                 205

Phe Tyr Cys Leu Ile His Arg Gln Val Lys Arg Ala Ala Gln Ala Leu
210                 215                 220

Asp Gln Tyr Lys Leu Arg Gln Ala Ser Ile His Ser Asn His Val Ala
225                 230                 235                 240

Arg Thr Asp Glu Ala Met Pro Gly Arg Phe Gln Glu Leu Asp Ser Arg
            245                 250                 255

Leu Ala Ser Gly Gly Pro Ser Glu Gly Ile Ser Ser Glu Pro Val Ser
        260                 265                 270

Ala Ala Thr Thr Gln Thr Leu Glu Gly Asp Ser Ser Glu Val Gly Asp
            275                 280                 285

Gln Ile Asn Ser Lys Arg Ala Lys Gln Met Ala Glu Lys Ser Pro Pro
290                 295                 300

Glu Ala Ser Ala Lys Ala Gln Pro Ile Lys Gly Ala Arg Arg Ala Pro
305                 310                 315                 320

Asp Ser Ser Ser Glu Phe Gly Lys Val Thr Arg Met Cys Phe Ala Val
            325                 330                 335

Phe Leu Cys Phe Ala Leu Ser Tyr Ile Pro Phe Leu Leu Leu Asn Ile
        340                 345                 350

Leu Asp Ala Arg Val Gln Ala Pro Arg Val Val His Met Leu Ala Ala
            355                 360                 365

Asn Leu Thr Trp Leu Asn Gly Cys Ile Asn Pro Val Leu Tyr Ala Ala
370                 375                 380

Met Asn Arg Gln Phe Arg Gln Ala Tyr Gly Ser Ile Leu Lys Arg Gly
385                 390                 395                 400

Pro Arg Ser Phe His Arg Leu His
                405
```

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
tccaggccag tacggaattc                                             20

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
actttcctcg ccaaaccagt ag                                          22

<210> SEQ ID NO 23
<211> LENGTH: 21
<212> TYPE: DNA
<213> ORGANISM: Artificial

-continued

```
<220> FEATURE:
<223> OTHER INFORMATION: probe

<400> SEQUENCE: 23
ctggtatttt ccttgcacca a                                                  21
```

METHODS OF SCREENING FOR A COMPOUND THAT REDUCES ATHEROGENESIS

FIELD OF THE INVENTION

The present invention relates to methods of using a G protein-coupled receptor (GPCR) to identify whether a candidate compound is a modulator of atherogenesis. In certain embodiments, the GPCR couples to Gi. In certain embodiments, the GPCR is human. Agonists of the invention are useful as therapeutic agents for inhibiting atherogenesis and for the prevention or treatment of atherosclerosis and atherosclerotic disease, including coronary artery disease, myocardial infarction, peripheral arterial disease, and ischemic stroke. Agonists of the invention are additionally useful as therapeutic agents for the prevention or treatment of conditions related to MCP-1 expression, including but not limited to rheumatoid arthritis, Crohn's disease, and multiple sclerosis.

BACKGROUND OF THE INVENTION

The following discussion is intended to facilitate the understanding of the invention, but is not intended nor admitted to be prior art to the invention.

A. Atherosclerosis

Atherosclerosis is a complex disease that is characterized by cholesterol deposition and monocyte infiltration into the subendothelial space, resulting in foam cell formation. Cardiovascular disease (mainly atherosclerosis) accounts for 35% of all deaths in the U.S.A. and similar Western countries. The monocyte/macrophage plays key roles both in the initiation and progression of atherosclerosis; for example, hypercholesterolemic mice become extremely resistant to atherosclerosis if they are bred to macrophage-deficient mice [Smith et al, PNAS (1995) 92:8264-8268].

ATP-binding cassette transporter 1 (ABCA1) controls apoAI-mediated cholesterol efflux from macrophages. Expression of ABCA1 is induced during monocyte differentiation into macrophages. ABCA1 protein is dramatically decreased in human atheroma in comparison to nonlesional tissue [Forcheron et al, Arterioscler Thromb Vasc Biol (2005) 25:1711-1717]. Inactivation of ABCA1 in macrophages markedly increases atherosclerosis and foam cell accumulation in ApoE$^{-/-}$ mice [Aiello et al, Arterioscler Thromb Vasc Biol (2002) 22:630-637]. ABCA1 upregulation in macrophages inhibits the progression of atherosclerotic lesions [Van Eck et al, Arterioscler Thromb Vasc Biol. (2006) 26:929-934].

Monocyte chemoattractant protein (MCP-1) is a key mediator of monocyte trafficking. In situ hybridization carried out on atherosclerotic human arteries detected MCP-1 mRNA macrophage-rich regions of atherosclerotic lesions but not in sublesional medial smooth muscle cells or in normal arteries [Yla-Herttuala et al, PNAS (1991) 88:5252-5256; Lutgens et al, Circulation (2005) 111:3443-3452]. MOP-1 expression by macrophages increases the progression of atherosclerosis by increasing both macrophage numbers and oxidized lipid accumulation [Aiello et al, Arterioscler Thromb Vasc Biol (1999) 19:1518-1525]. Use of knockout mice has implicated MCP-1 in attracting macrophage recruitment in atherosclerosis. Atherosclerosis is essentially abolished in MCP-1$^{-/-}$ mice indicating that MCP-1 is absolutely required for atherosclerosis from its earliest stages [Gu et al, Mol Cell (1998) 2:275-281]. Using a dominant-negative mutant of MCP-1, it has been shown that vascular inflammation mediated by MCP-1 has a central role in the development of atherosclerosis, and plaque destabilization, leading to acute myocardial ischemia [Egashira, Hypertension (2003) 41:834-841].

Conditions related to expression of MCP-1 in monocytes/macrophages additional to atherosclerosis and atherosclerotic disease include, but are not limited to, rheumatoid arthritis [see, e.g., Koch et al, J Clin Invest (1992) 90:772-779; Dawson et al, Expert Opin Ther Targets (2003) 7:35-48].

An agent that decreases expression of MCP-1 or increases expression of ABCA1 is useful in the treatment of atherosclerosis and atherosclerotic disease, and an agent which is a small molecule is further advantageous.

B. GPR84

GPR84 is a GPCR asserted to be selectively expressed in granulocytes [Yousefi et al., J Leukoc Biol (2001) 69:1045-1052]. GPR84 has been conjectured to have a role in regulating early IL-4 gene expression in activated T cells [Venkataraman et al, Immunol Lett (2005) 101:144-153].

C. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

| | | |
|---|---|---|
| CLARITIN ® (allergies) | PROZAC ® (depression) | VASOTEC ® (hypertension) |
| PAXIL ® (depression) | ZOLOFT ® (depression) | ZYPREXA ®(psychotic disorder) |
| COZZAR ® (hypertension) | IMITREX ® (migraine) | ZANTAC ® (reflux) |
| PROPULSID ® (reflux disease) | RISPERDAL ® (schizophrenia) | SEREVENT ® (asthma) |
| PEPCID ® (reflux) | GASTER ® (ulcers) | ATROVENT ® (bronchospasm) |
| EFFEXOR ® (depression) | DEPAKOTE ® (epilepsy) | CARDURA ®(prostatic hypertrophy) |
| ALLEGRA ® (allergies) | LUPRON ® (prostate cancer) | ZOLADEX ® (prostate cancer) |
| DIPRIVAN ® (anesthesia) | BUSPAR ® (anxiety) | VENTOLIN ® (bronchospasm) |
| HYTRIN ® (hypertension) | WELLBUTRIN ® (depression) | ZYRTEC ® (rhinitis) |
| PLAVIX ® (MI/stroke) | TOPROL-XL ® (hypertension) | TENORMIN ® (angina) |
| XALATAN ® (glaucoma) | SINGULAIR ® (asthma) | DIOVAN ® (hypertension) |
| HARNAL ® (prostatic hyperplasia) | | |

(Med Ad News 1999 Data).

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Gs-coupled GPCRs elevate-intracellular cAMP levels. GPCRs coupled to Gi, Go, or Gz lower intracellular cAMP levels. Gq-coupled GPCRs elevate intracellular $IP_3$ and $Ca^{2+}$ levels.

There are also promiscuous G proteins, which appear to couple several classes of GPCRs to the phospholipase C pathway, such as G15 or G16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24]. A GPCR coupled to the phospholipase C pathway elevates intracellular $IP_3$ and $Ca^{2+}$ levels.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

Nucleotide sequence encoding human GPR84 polypeptide is given in SEQ ID NO:1. The amino acid sequence of said encoded human GPR84 polypeptide is given in SEQ ID NO:2. Nucleotide sequence encoding mouse GPR84 polypeptide is given in SEQ ID NO:3. The amino acid sequence of said encoded mouse GPR84 polypeptide is given in SEQ ID NO:4. Nucleotide sequence encoding rat GPR84 polypeptide is given in SEQ ID NO:5. The amino acid sequence of said encoded rat GPR84 polypeptide is given in SEQ ID NO:6. Nucleotide sequence encoding amino acids 2-396 of SEQ ID NO:2 fused N-terminally with a hemagglutinin (HA) epitope tag is given in SEQ ID NO:19. The amino acid sequence of said encoded amino acids 2-396 of SEQ ID NO:2 fused N-terminally with a hemagglutinin (HA) epitope tag is given in SEQ ID NO:20.

Applicants have shown that GPR84 is expressed endogenously in monocytes/macrophages. Applicants have shown that activation of GPR84 leads to decreased levels of intracellular cAMP, consistent with GPR84 being Gi-coupled. Applicants have shown that an agonist of GPR84 selectively modulates cytokine expression in monocytes/macrophages, including decreasing MCP-1 expression. Applicants have shown that an agonist of GPR84 increases expression of ABCA1 in monocytes/macrophages. The present invention features methods relating to GPR84 for identifying a candidate compound as a modulator of atherogenesis, as an agonist for use as a pharmaceutical agent for atherosclerosis or an atherosclerotic disease, as a compound for the prevention or treatment of atherosclerosis or an atherosclerotic disease, or as a compound for the prevention or treatment of a condition related to MCP-1 expression. The present invention additionally features methods of using an agonist of GPR84 for preventing or treating atherosclerosis or an atherosclerotic disease in a mammal. The present invention additionally features methods of using an agonist of GPR84 for preventing or treating a condition related to MCP-1 expression in a mammal. Agonists of the invention are useful as therapeutic agents for inhibiting atherogenesis and for the prevention or treatment of atherosclerosis and atherosclerotic disease, including coronary artery disease, myocardial infarction, peripheral arterial disease, and ischemic stroke. Agonists of the invention are additionally useful as therapeutic agents for the prevention or treatment of conditions related to MCP-1 expression, including but not limited to rheumatoid arthritis, Crohn's disease, and multiple sclerosis.

In a first aspect, the invention features a method of identifying a candidate compound as a modulator of atherogenesis, comprising the steps of:
(a) contacting the candidate compound with a GPCR comprising an amino acid sequence selected from the group consisting of:
  (i) the amino acid sequence of SEQ ID NO:2;
  (ii) amino acids 2-396 of SEQ ID NO:2;
  (iii) amino acids 2-396 of SEQ ID NO:2, wherein the GPCR does not comprise amino acids 1-396 of SEQ ID NO:2;
  (iv) the amino acid sequence of SEQ ID NO:20;
  (v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
  (vi) the amino acid sequence of a G protein-coupled receptor encoded by a polynucleotide hybridizing under stringent conditions to the complement of SEQ ID NO:1;
  (vii) the amino acid sequence of an endogenous G protein-coupled receptor having at least about 75% identity, at least about 80% identity, at least about 85% identity, at least about 90% identity, or at least about 95% identity to SEQ ID NO:2;
(viii) the amino acid sequence of SEQ ID NO:4;
(ix) amino acids-2-396 of SEQ ID NO:4;
(x) amino acids 2-396 of SEQ ID NO:4 wherein the GPCR does not comprise amino acids 1-396 of SEQ ID NO:4;
(xi) the amino acid sequence of a G protein-coupled receptor encoded by a polynucleotide hybridizing under stringent conditions to the complement of SEQ ID NO:3;
(xii) the amino acid sequence of an endogenous G protein-coupled receptor having at least about 75% identity, at least about 80% identity, at least about 85% identity, at least about 90% identity, or at least about 95% identity to SEQ ID NO:4;
(xiii) the amino acid sequence of SEQ ID NO:6;
(xiv) amino acids 2-396 of SEQ ID NO:6;
(xv) amino acids 2-396 of SEQ ID NO:6, wherein the GPCR does not comprise amino acids 1-396 of SEQ ID NO:6;
(xvi) the amino acid sequence of a G protein-coupled receptor encoded by a polynucleotide hybridizing under stringent conditions to the complement of SEQ ID NO:5; and
(xvii) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof;
wherein the receptor couples to a G protein; and
(b) determining the ability of the compound to inhibit or stimulate functionality of the GPCR,
wherein the ability of the compound to inhibit or stimulate functionality of the GPCR is indicative of the compound being a modulator of atherogenesis.

The invention also features a method of identifying a candidate compound as a modulator of MCP-1 expression, comprising the steps of:
(a) contacting the candidate compound with a GPCR comprising an amino acid sequence selected from the group consisting of:
(i) the amino acid sequence of SEQ ID NO:2;
(ii) amino acids 2-396 of SEQ ID NO:2;
(iii) amino acids 2-396 of SEQ ID NO:2, wherein the GPCR does not comprise amino acids 1-396 of SEQ ID NO:2;
(iv) the amino acid sequence of SEQ ID NO:20;
(v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
(vi) the amino acid sequence of a G protein-coupled receptor encoded by a polynucleotide hybridizing under stringent conditions to the complement of SEQ ID NO:1;
(vii) the amino acid sequence of an endogenous G protein-coupled receptor having at least about 75% identity, at least about 80% identity, at least about 85% identity, at least about 90% identity, or at least about 95% identity to SEQ ID NO:2;
(viii) the amino acid sequence of SEQ ID NO:4;
(ix) amino acids 2-396 of SEQ ID NO:4;
(x) amino acids 2-396 of SEQ ID NO:4 wherein the GPCR doei not comprise amino acids 1-396 of SEQ ID NO:4;
(xi) the amino acid sequence of a G protein-coupled receptor encoded by a polynucleotide hybridizing under stringent conditions to the complement of SEQ ID NO:3;
(xii) the amino acid sequence of an endogenous G protein-coupled receptor having at least about 75% identity, at least about 80% identity, at least about 85% identity, at least about 90% identity, or at least about 95% identity to SEQ ID NO:4;
(xiii) the amino acid sequence of SEQ ID NO:6;
(xiv) amino acids 2-396 of SEQ ID NO:6;
(xv) amino acids 2-396 of SEQ ID NO:6, wherein the GPCR does not comprise amino acids 1-396 of SEQ ID NO:6;
(xvi) the amino acid sequence of a G protein-coupled receptor encoded by a polynucleotide hybridizing under stringent conditions to the complement of SEQ ID NO:5; and
(xvii) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof;
wherein the receptor couples to a G protein; and
(b) determining the ability of the compound to inhibit or stimulate functionality of the GPCR,
wherein the ability of the compound to inhibit or stimulate functionality of the GPCR is indicative of the compound being a modulator of MCP-1 expression.

The invention also features a method of identifying a candidate compound as a modulator of ABCA1 expression, comprising the steps of:
(a) contacting the candidate compound with a GPCR comprising an amino acid sequence selected from the group consisting of:
(i) the amino acid sequence of SEQ ID NO:2;
(ii) amino acids 2-396 of SEQ ID NO:2;
(iii) amino acids 2-396 of SEQ ID NO:2, wherein the GPCR does not comprise amino acids 1-396 of SEQ ID NO:2;
(iv) the amino acid sequence of SEQ ID NO:20;
(v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
(vi) the amino acid sequence of a G protein-coupled receptor encoded by a polynucleotide hybridizing under stringent conditions to the complement of SEQ ID NO:1;
(vii) the amino acid sequence of an endogenous G protein-coupled receptor having at least about 75% identity, at least about 80% identity, at least about 85% identity, at least about 90% identity, or at least about 95% identity to SEQ ID NO:2;
(viii) the amino acid sequence of SEQ ID NO:4;
(ix) amino acids 2-396 of SEQ ID NO:4;
(x) amino acids 2-396 of SEQ ID NO:4 wherein the GPCR does not comprise amino acids 1-396 of SEQ ID NO:4;

(xi) the amino acid sequence of a G protein-coupled receptor encoded by a polynucleotide hybridizing under stringent conditions to the complement of SEQ ID NO:3;
(xii) the amino acid sequence of an endogenous G protein-coupled receptor having at least about 75% identity, at least about 80% identity, at least about 85% identity, at least about 90% identity, or at least about 95% identity to SEQ ID NO:4;
(xiii) the amino acid sequence of SEQ ID NO:6;
(xiv) amino acids 2-396 of SEQ ID NO:6;
(xv) amino acids 2-396 of SEQ ID NO:6, wherein the GPCR does not comprise amino acids 1-396 of SEQ ID NO:6;
(xvi) the amino acid sequence of a G protein-coupled receptor encoded by a polynucleotide hybridizing under stringent conditions to the complement of SEQ ID NO:5; and
(xvii) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof;
wherein the receptor couples to a G protein; and
  (b) determining the ability of the compound to inhibit or stimulate functionality of the GPCR,
    wherein the ability of the compound to inhibit or stimulate functionality of the GPCR is indicative of the compound being a modulator of ABCA1 expression.

The invention also features a method of identifying a candidate compound as an agonist for use as a pharmaceutical agent for atherosclerosis or an atherosclerotic disease, comprising the steps of:
  (a) contacting the candidate compound with a GPCR comprising an amino acid sequence selected from the group consisting of:
    (i) the amino acid sequence of SEQ ID NO:2;
    (ii) amino acids 2-396 of SEQ ID NO:2;
    (iii) amino acids 2-396 of SEQ ID NO:2, wherein the GPCR does not comprise amino acids 1-396 of SEQ ID NO:2;
    (iv) the amino acid sequence of SEQ ID NO:20;
    (v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
    (vi) the amino acid sequence of a G protein-coupled receptor encoded by a polynucleotide hybridizing under stringent conditions to the complement of SEQ ID NO:1;
    (vii) the amino acid sequence of an endogenous G protein-coupled receptor having at least about 75% identity, at least about 80% identity, at least about 85% identity, at least about 90% identity, or at least about 95% identity to SEQ ID NO:2;
    (viii) the amino acid sequence of SEQ ID NO:4;
    (ix) amino acids 2-396 of SEQ ID NO:4;
    (x) amino acids 2-396 of SEQ ID NO:4 wherein the GPCR does not comprise amino acids 1-396 of SEQ ED NO:4;
    (xi) the amino acid sequence of a G protein-coupled receptor encoded by a polynucleotide hybridizing under stringent conditions to the complement of SEQ ID NO:3;
    (xii) the amino acid sequence of an endogenous G protein-coupled receptor having at least about 75% identity, at least about 80% identity, at least about 85% identity, at least about 90% identity, or at least about 95% identity to SEQ ID NO:4;
    (xiii) the amino acid sequence of SEQ ID NO:6;
    (xiv) amino acids 2-396 of SEQ ID NO:6;
    (xv) amino acids 2-396 of SEQ ID NO:6, wherein the GPCR does not comprise amino acids 1-396 of SEQ ID NO:6;
    (xvi) the amino acid sequence of a G protein-coupled receptor encoded by a polynucleotide hybridizing under stringent conditions to the complement of SEQ ID NO:5; and
    (xvii) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof;
wherein the receptor couples to a G protein; and
  (b) determining the ability of the compound to stimulate functionality of the GPCR,
    wherein the ability of the compound to stimulate functionality of the GPCR is indicative of the compound being an agonist for use as a pharmaceutical agent for atherosclerosis or an atherosclerotic disease.

In some embodiments, the agonist for use as a pharmaceutical agent for atherosclerosis or an atherosclerotic disease is an agonist for use as a pharmaceutical agent for atherosclerosis. In some embodiments, the agonist for use as a pharmaceutical agent for atherosclerosis or an atherosclerotic disease is an agonist for use as a pharmaceutical agent for an atherosclerotic disease. In some embodiments, the atherosclerotic disease is selected from the group consisting of coronary artery disease, myocardial infarction, peripheral artery disease, and ischemic stroke.

The invention also features a method of identifying a compound for inhibiting atherogenesis, comprising the steps of:
  (a) contacting a candidate candidate compound with a GPCR comprising an amino acid sequence selected from the group consisting of:
    (i) the amino acid sequence of SEQ ID NO:2;
    (ii) amino acids 2-396 of SEQ ID NO:2;
    (iii) amino acids 2-396 of SEQ ID NO:2, wherein the GPCR does not comprise amino acids 1-396 of SEQ ID NO:2;
    (iv) the amino acid sequence of SEQ ID NO:20;
    (v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
    (vi) the amino acid sequence of a G protein-coupled receptor encoded by a polynucleotide hybridizing under stringent conditions to the complement of SEQ ID NO:1;
    (vii) the amino acid sequence of an endogenous G protein-coupled receptor having at least about 75% identity, at least about 80% identity, at least about 85% identity, at least about 90% identity, or at least about 95% identity to SEQ ID NO:2;
    (viii) the amino acid sequence of SEQ ID NO:4;
    (ix) amino acids 2-396 of SEQ ID NO:4;
    (x) amino acids 2-396 of SEQ ID NO:4 wherein the GPCR does not comprise amino acids 1-396 of SEQ ID NO:4;

(xi) the amino acid sequence of a G protein-coupled receptor encoded by a polynucleotide hybridizing under stringent conditions to the complement of SEQ ID NO:3;
(xii) the amino acid sequence of an endogenous G protein-coupled receptor having at least about 75% identity, at least about 80% identity, at least about 85% identity, at least about 90% identity, or at least about 95% identity to SEQ ID NO:4;
(xiii) the amino acid sequence of SEQ ID NO:6;
(xiv) amino acids 2-396 of SEQ ID NO:6;
(xv) amino acids 2-396 of SEQ ID NO:6, wherein the GPCR does not comprise amino acids 1-396 of SEQ ID NO:6;
(xvi) the amino acid sequence of a G protein-coupled receptor encoded by a polynucleotide hybridizing under stringent conditions to the complement of SEQ ID NO:5; and
(xvii) the amino acid sequence of an endogenous G protein-coupled receptor having at least about 75% identity, at least about 80% identity, at least about 85% identity, at least about 90% identity, or at least about 95% identity to SEQ ID NO:6;
or a variant or biologically active fragment thereof;
wherein the receptor couples to a G protein; and
 (b) determining the ability of the candidate compound to stimulate functionality of the GPCR,
  wherein the ability of the candidate compound to stimulate functionality of the GPCR is indicative of the candidate compound being a compound for inhibiting atherogenesis.

The invention also features a method of identifying a compound for the prevention or treatment of atherosclerosis or an atherosclerotic disease, comprising the steps of:
 (a) contacting a candidate candidate compound with a GPCR comprising an amino acid sequence selected from the group consisting of:
  (i) the amino, acid sequence of SEQ ID NO:2;
  (ii) amino acids 2-396 of SEQ ID NO:2;
  (iii) amino acids 2-396 of SEQ ID NO:2, wherein the GPCR does not comprise amino acids 1-396 of SEQ ID NO:2;
  (iv) the amino acid sequence of SEQ ID NO:20;
  (v) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
  (vi) the amino acid sequence of a G protein-coupled receptor encoded by a polynucleotide hybridizing under stringent conditions to the complement of SEQ ID NO:1;
  (vii) the amino acid sequence of an endogenous G protein-coupled receptor having at least about 75% identity, at least about 80% identity, at least about 85% identity, at least about 90% identity, or at least about 95% identity to SEQ ID NO:2;
  (viii) the amino acid sequence of SEQ ID NO:4;
  (ix) amino acids 2-396 of SEQ ID NO:4;
  (x) amino acids 2-396 of SEQ ID NO:4 wherein the GPCR does not comprise amino acids 1-396 of SEQ ID NO:4;
  (xi) the amino acid sequence of a G protein-coupled receptor encoded by a polynucleotide hybridizing under stringent conditions to the complement of SEQ ID NO:3;
  (xii) the amino acid sequence of an endogenous G protein-coupled receptor having at least about 75% identity, at least about 80% identity, at least about 85% identity, at least about 90% identity, or at least about 95% identity to SEQ ID NO:4;
  (xiii) the amino acid sequence of SEQ ID NO:6;
  (xiv) amino acids 2-396 of SEQ ID NO:6;
  (xv) amino acids 2-396 of SEQ ID NO:6, wherein the GPCR does not comprise amino acids 1-396 of SEQ ID NO:6;
  (xvi) the amino acid sequence of a G protein-coupled receptor encoded by a polynucleotide hybridizing under stringent conditions to the complement of SEQ ID NO:5; and
  (xvii) the amino acid sequence of an endogenous G protein-coupled receptor having at least about 75% identity, at least about 80% identity, at least about 85% identity, at least about 90% identity, or at least about 95% identity to SEQ ID NO:6;
  or a variant or biologically active fragment thereof;
 wherein the receptor couples to a G protein; and
 (b) determining the ability of the candidate compound to stimulate functionality of the GPCR,
  wherein the ability of the candidate compound to stimulate functionality of the GPCR is indicative of the candidate compound being a compound for the prevention or treatment of atherosclerosis or an atherosclerotic disease.

In some embodiments, the compound for the prevention or treatment of atherosclerosis or an atherosclerotic disease is a compound for the prevention or treatment of atherosclerosis. In some embodiments, the compound for the prevention or treatment of atherosclerosis or an atherosclerotic disease is a compound for the prevention or treatment of an atherosclerotic disease.

In some embodiments, the atherosclerotic disease is selected from the group consisting of coronary artery disease, myocardial infarction, peripheral artery disease, and ischemic stroke.

The invention also features a method of identifying a compound for the prevention or treatment of a condition related to MCP-1 expression, comprising the steps of:
 (a) contacting a candidate candidate compound with a GPCR comprising an amino acid sequence selected from the group consisting of:
  (i) the amino acid sequence of SEQ ID NO:2;
  (ii) amino acids 2-396 of SEQ ID NO:2;
  (iii) amino acids 2-396 of SEQ ID NO:2, wherein the GPCR does not comprise amino acids 1-396 of SEQ ID NO:2;
  (iv) the amino acid sequence of SEQ ID NO:20;
  (v) the amino acid sequence of a G protein-coupled receptor encoded by a polynucleotide that is amplifiable by polymerase chain reaction (PCR) on a human DNA sample using specific primers. SEQ ID NO:7 and SEQ ID NO:8;
  (vi) the amino acid sequence of a G protein-coupled receptor encoded by a polynucleotide hybridizing under stringent conditions to the complement of SEQ ID NO:1;
  (vii) the amino acid sequence of an endogenous G protein-coupled receptor having at least about 75% identity, at least about 80% identity, at least about 85% identity, at least about 90% identity, or at least about 95% identity to SEQ ID NO:2;
  (viii) the amino acid sequence of SEQ ID NO:4;
  (ix) amino acids 2-396 of SEQ ID NO:4;

(x) amino acids 2-396 of SEQ ID NO:4 wherein the GPCR does not comprise amino acids 1-396 of SEQ ID NO:4;

(xi) the amino acid sequence of a G protein-coupled receptor encoded by a polynucleotide hybridizing under stringent conditions to the complement of SEQ ID NO:3;

(xii) the amino acid sequence of an endogenous G protein-coupled receptor having at least about 75% identity, at least about 80% identity, at least about 85% identity, at least about 90% identity, or at least about 95% identity to SEQ ID NO:4;

(xiii) the amino acid sequence of SEQ ID NO:6;

(xiv) amino acids 2-396 of SEQ ID NO:6;

(xv) amino acids 2-396 of SEQ ID NO:6, wherein the GPCR does not comprise amino acids 1-396 of SEQ ID NO:6;

(xvi) the amino acid sequence of a G protein-coupled receptor encoded by a polynucleotide hybridizing under stringent conditions to the complement of SEQ ID NO:5; and (xvii) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof;

wherein the receptor couples to a G protein; and (b) determining the ability of the candidate compound to stimulate functionality of the GPCR, wherein the ability of the candidate compound to stimulate functionality of the GPCR is indicative of the candidate compound being a compound for the prevention or treatment of a condition related to MCP-1 expression.

In some embodiments, the condition related to MCP-1 expression is selected from the group consisting of atherosclerosis, an atherosclerotic disease, rheumatoid arthritis, Crohn's disease, and multiple sclerosis.

In some embodiments, the condition related to MCP-1 expression is selected from the group consisting of atherosclerosis, rheumatoid arthritis, psoriatic arthritis, osteoarthritis, ulcerative colitis, Crohn's disease, insulin resistance, Type 1 diabetes, Type 2 diabetes, metabolic syndrome, obesity, lower than normal HDL-cholesterol, hypertension, hyperlipidemia, ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, multiple sclerosis, ischemic stroke, Parkinson's disease, prion-associated disease, excitotoxic injury, mild cognitive impairment (MCI) and Alzheimer's disease.

In some embodiments; the condition related to MCP-1 expression is an inflammation-related disease or disorder.

In some embodiments, the G protein is Gi.

In some embodiments, the G protein is Gq(del)/Gi chimeric G protein.

In some embodiments, said contacting is carried out in the absence of a known ligand of the receptor. In some embodiments, said contacting is carried out in the absence of a known agonist of the receptor. In some embodiments, said identifying is directly identifying.

In some embodiments, said contacting is carried out in the presence of a known ligand of the GPCR. In some embodiments, said contacting is carried out in the presence of a known agonist of the GPCR. In some embodiments, the known agonist of the GPCR is a compound selected from Table 1. In some embodiments, the known agonist is Compound 1.

In some embodiments, the human DNA human genomic DNA.

In some embodiments, the human DNA is human cDNA derived from a tissue or cell type that expresses GPR84. In some embodiments, the human cDNA is derived from a leukocyte. In some embodiments, the human cDNA is derived from a monocyte/macrophage. In certain embodiments, the human cDNA is derived from a granulocyte.

In some embodiments, the G protein-coupled receptor encoded by a polynucleotide hybridizing under stringent conditions to the complement of SEQ ID NO:1, SEQ ID NO:3 or SEQ ID NO:5 is an endogenous GPCR. In some embodiments, the G protein-coupled receptor encoded by a polynucleotide hybridizing under stringent conditions to the complement of SEQ ID NO:1, SEQ ID NO:3 or SEQ ID NO:5 can decrease a level of intracellular cAMP in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 can increase a level of intracellular $IP_3$ accumulation in a cell comprising Gq(del)/Gi chimeric G protein in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 can cause melanophore cells to undergo pigment aggregation in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 which can decrease a level of intracellular cAMP, which can increase a level of intracellular $IP_3$ accumulation in a cell comprising Gq(del)/Gi chimeric G protein, or which can cause melanophore cells to undergo pigment aggregation in response to a compound selected from Table 1 exhibits a detectable level of constitutive activity. In some embodiments, the compound selected from Table 1 is Compound 1.

In some embodiments, the ability of the compound to stimulate functionality of the GPCR is indicative of the compound being an inhibitor of atherogenesis. In some embodiments, the ability of the compound to stimulate functionality of the GPCR is indicative of the compound being a compound that decreases atherogenesis.

In some embodiments, the ability of the compound to stimulate functionality of the GPCR is indicative of the compound being a compound that decreases MCP-1 expression in monocytes/macrophages.

In some embodiments, the ability of the compound to stimulate functionality of the GPCR is indicative of the compound being a compound that increases ABCA1 expression in monocytes/macrophages.

In some embodiments, the MCP-1 expression comprises MCP-1 expression in monocytes/macrophages.

In some embodiments, the MCP-1 expression is in a monocyte/macrophage.

In some embodiments, the ABCA1 expression is in a monocyte/macrophage.

In some embodiments, the GPCR is recombinant.

In some embodiments, the GPCR is endogenous.

In some embodiments, the GPCR is a mammalin GPR84.

In some embodiments, the GPCR is constitutively active. In some embodiments, the GPCR that is endogenous is constitutively active. In some embodiments, the GPCR that is a mammalian GPR84 is constitutively active. In some embodiments, the mammalian GPR84 is a human GPR84. In some embodiments, the human GPR84 is SEQ ID NO:2 or an allele thereof.

In some embodiments, the GPCR exhibits a detectable level of constitutive activity. In some embodiments, the GPCR that is endogenous exhibits a detectable level of constitutive activity. In some embodiments, the GPCR that is a mammalian GPR84 exhibits a detectable level of constitutive activity. In some embodiments, the mammalian GPR84 is a human GPR84. In some embodiments, the human GPR84 is SEQ ID NO:2 or an allele thereof.

In some embodiments, said contacting comprises contacting with a host cell comprising the GPCR or with a host cell membrane that comprises the GPCR, wherein said host cell comprises an expression vector comprising a polynucleotide encoding the GPCR. In certain embodiments, the host cell is a eukaryotic host cell. In some embodiments, the eukaryotic host cell is a mammalian host cell. In some embodiments, the eukaryotic host cell is a melanophore host cell. In some embodiments, the eukaryotic host cell is a yeast host cell. In some embodiments, the mammalian host cell is a non-myeloid host cell. In some embodiments, the mammalian host cell is not identical to a monocyte or to a cell derived from a monocyte. In some embodiments, the mammalian host cell is a myeloid host cell. In some embodiments, the mammalian host cell is identical a monocyte or to a cell derived from a monocyte.

In some embodiments, said determining is by a process comprising the measurement of a level of a second messenger.

In some embodiments, said determining is by a process comprising the measurement of a level of a second messenger selected from the group consisting of cyclic AMP (cAMP), cyclic GMP (cGMP), inositol 1,4,5-triphosphate ($IP_3$), diacylglycerol (DAG), MAP kinase activity, MAPK/ERK kinase kinase-1 (MEKK1) activity, and $Ca^{2+}$. In some embodiments, said second messenger is cAMP. In some embodiments, the level of intracellular cAMP is decreased. In some embodiments relating to Gq(del)/Gi chimeric G protein, said second messenger is $IP_3$. In some embodiments, the level of intracellular $IP_3$ is increased. In some embodiments relating to Gq(del)/Gi chimeric G protein, said second messenger is $Ca^{2+}$ In some embodiments, the level of intracellular $Ca^{2+}$ is increased. In some embodiments, the $Ca^{2+}$ measurement is carried out by fluorometric imaging plate reader (FLIPR) assay.

In some embodiments, said determining is through the use of a Melanophore assay. In some embodiments, the melanophore cells undergo pigment aggregation.

In some embodiments, said determining is through the measurement of GTPγS binding to membrane comprising the GPCR. In some embodiments, GTPγS binding to membrane comprising the GPCR is increased.

In some embodiments, said determining is through CRE reporter assay. In some embodiments relating to Gq(del)/Gi chimeric G protein, said determining is through AP1-reporter assay. In some embodiments relating to Gq(del)/Gi chimeric G protein, said determining is through SRF-reporter assay.

In some embodiments, said determining is carried out with membrane comprising the GPCR.

In some embodiments, the modulator is an agonist, partial agonist, inverse agonist, or antagonist of the GPCR. In some embodiments, the agonist, partial agonist, inverse agonist, or antagonist of the GPCR is an agonist, partial agonist, inverse agonist, or antagonist of a mammalian GPR84. In some embodiments, the mammalian GPR84 is a human GPR84. In some embodiments, the modulator is an agonist of the GPCR. In some embodiments, the modulator is a partial agonist of the GPCR.

In some embodiments, the candidate compound is a small molecule. In some embodiments, the candidate compound is not an antibody or an antigen-binding fragment thereof. In some embodiments, the candidate compound is not a polypeptide. In some embodiments, the candidate compound is not a lipid. In certain embodiments, the candidate compound is not identical to a compound in Table 1. In certain embodiments, the candidate compound is not identical to Compound 1. In certain embodiments, the candidate compound is non-endogenous. In certain embodiments, the candidate compound is not endogenous. In some embodiments, the candidate compound is not material that a prokaryote or eukaryote naturally produces. In some embodiments, the candidate compound is not material that a prokaryote naturally produces. In some embodiments, the candidate compound is not material that a eukaryote naturally produces.

In some embodiments, the method further comprises the step of comparing the modulation of the receptor caused by the candidate compound to a second modulation of the receptor caused by contacting the receptor with a known modulator of the receptor.

In some embodiments, said method further comprises synthesis of the modulator or agonist or identified compound.

In some embodiments, said method further comprises: optionally, determining the structure of the modulator or agonist or identified compound; and providing the modulator or agonist or identified compound or the name or structure of the modulator or agonist or identified compound.

In some embodiments, said method further comprises: optionally, determining the structure of the modulator or agonist or identified compound; optionally, providing the modulator or agonist or identified compound or the name or structure of the modulator or agonist or identified compound; and producing or synthesizing the modulator or agonist or identified compound.

In some embodiments, said method further comprises formulating the modulator of atherogenesis, the modulator of MCP-1 expression, the modulator of ABCA1 expression, the agonist for use as a pharmaceutical agent for atherosclerosis or an atherosclerotic disease, the compound for the prevention or treatment of atherosclerosis or an atherosclerotic disease, or the compound for the prevention or treatment of a condition related to MCP-1 expression into a pharmaceutical. In some embodiments, said method further comprises formulating the modulator of atherogenesis, the modulator of MCP-1 expression, the modulator of ABCA1 expression, the agonist for use as a pharmaceutical agent for atherosclerosis or an atherosclerotic disease, the compound for the prevention or treatment of atherosclerosis or an atherosclerotic disease, or the compound for the prevention or treatment of a condition related to MCP-1 expression into a pharmaceutical composition.

In a second aspect, the invention features a modulator identifiable according to a method of the first aspect.

In certain embodiments, the modulator is a modulator of atherogenesis or a modulator of MCP-1 expression or a modulator of ABCA1 expression.

In some embodiments, the modulator is identified according to a method of the first aspect.

In some embodiments, the modulator is an agonist, a partial agonist, an inverse agonist, or an antagonist of the GPCR. In some embodiments, the agonist, partial agonist, inverse agonist, or antagonist of the GPCR is an agonist, partial agonist, inverse agonist, or antagonist of a mammalian GPR84. In some embodiments, the mammalian GPR84 is a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator is an agonist of the GPCR. In some embodiments, the agonist of the GPCR is an agonist of a mammalian GPR84. In some embodiments, the mammalian GPR84 is a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist with an $EC_{50}$ of less than about 10 µM, of less than about 1 µM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator is orally active.

In a third aspect, the invention features a pharmaceutical composition comprising a modulator of a mammalian GPR84 and a pharmaceutically acceptable carrier. The invention also relates to a composition comprising a modulator of a mammalian GPR84.

The invention also relates to a pharmaceutical composition comprising a modulator of atherogenesis or a modulator of MCP-1 expression or a modulator of ABCA1 expression and a pharmaceutically acceptable carrier or to a composition comprising the modulator of atherogenesis or the modulator of MCP-1 expression or the modulator of ABCA1 expression, wherein said modulator of atherogenesis or said modulator of MCP-1 expression or said modulator of ABCA1 expression is an agonist, partial agonist, inverse agonist or antagonist of a mammalian GPR84.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is according to the second aspect.

In some embodiments, the modulator of the mammalian GPR84 is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the modulator is an agonist with an $EC_{50}$ of less than about 10 μM, of less than about 1 μM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 μM. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 μM. In some embodiments, the modulator is an agonist with an $EC_{50}$ in said assay of less than a value selected from the interval of about 10 nM to 1 μM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator is orally active.

In a fourth aspect, the invention features a method of preparing a pharmaceutical composition comprising admixing a modulator of a mammalian GPR84 and a pharmaceutically acceptable carrier.

The invention also relates to a method of preparing a pharmaceutical composition comprising admixing a modulator of atherogenesis or a modulator of MCP-1 expression or a modulator of ABCA1 expression and a pharmaceutically acceptable carrier, wherein said modulator of atherogenesis or said modulator of MCP-1 expression or said modulator of ABCA1 expression is an agonist, partial agonist, inverse agonist or antagonist of a mammalian GPR84.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator of the mammalian GPR84 is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the method comprises admixing the modulator of a mammalian GPR84 or the modulator of atherogenesis or the modulator of MCP-1 expression or the modulator of ABCA1 expression and the pharmaceutically acceptable carrier and a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the modulator is an agonist with an $EC_{50}$ of less than about 10 µM, of less than about 1 µM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator is orally active.

In a fifth aspect, the invention features a method of inhibiting atherogenesis comprising administering to a mammal in need thereof a therapeutically effective amount of a modulator of the mammalian GPR84 or a pharmaceutical composition comprising the modulator and a pharmaceutically acceptable carrier or a composition comprising the modulator.

In some embodiments, the modulator is according to the second aspect. In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human. GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the mammal is a human.

In some embodiments, the modulator is an agonist with an $EC_{50}$ of less than about 10 µM, of less than about 1 µM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In some embodiments, said administering is oral.

In a sixth aspect, the invention features use of a modulator of a mammalian GPR84 or of a pharmaceutical composition comprising the modulator and a pharmaceutically acceptable carrier or of a composition comprising the modulator to inhibit atherogenesis in the human or animal body by therapy.

In some embodiments, the modulator is according to the second aspect. In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some, embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain, embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the pharmaceutical composition or the composition further comprise a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the animal is a non-human mammal.

In some embodiments, the modulator is an agonist with an $EC_{50}$ of less than about 10 µM, of less than about 1 µM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In, some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In a seventh aspect, the invention features a method of preventing or treating atherosclerosis or an atherosclerotic disease comprising administering to a mammal in need thereof a therapeutically effective amount of a modulator of the mammalian GPR84 or of a pharmaceutical composition comprising the modulator and a pharmaceutically acceptable carrier or of a composition comprising the modulator.

In certain embodiments, the method of preventing or treating atherosclerosis or an atherosclerotic disease is a method of preventing or treating atherosclerosis. In certain embodiments, the method of preventing or treating atherosclerosis or an atherosclerotic disease is a method of preventing or treating an atherosclerotic disease.

In some embodiments, the atherosclerotic disease is selected from the group consisting of coronary artery disease, myocardial infarction, peripheral arterial disease, and ischemic stroke.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the pharmaceutical composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the mammal is a human.

In some embodiments, the modulator is an agonist with an $EC_{50}$ of less than about 10 μM, of less than about 1 μM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 μM. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 μM. In some embodiments, the modulator is an agonist with an $EC_{50}$ in said assay of less than a value selected from the interval of about 10 nM to 1 μM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In some embodiments, said administering is oral.

In an eighth aspect, the invention features a use of a modulator of a mammalian GPR84 or of a pharmaceutical composition comprising the modulator and a pharmaceutically acceptable carrier or of a composition comprising the modulator to prevent or treat atherosclerosis or an atherosclerotic disease in the human or animal body by therapy.

In certain embodiments, to prevent or treat atherosclerosis or an atherosclerotic disease is to prevent or treat atherosclerosis. In certain embodiments, to prevent or treat atherosclerosis or an atherosclerotic disease is to prevent or treat an atherosclerotic disease.

In some embodiments, the atherosclerotic disease is selected from the group consisting of coronary artery disease, myocardial infarction, peripheral arterial disease, and ischemic stroke.

In some embodiments, the modulator is according to the second aspect. In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In, some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the animal is a non-human mammal.

In some embodiments, the modulator is an agonist with an $EC_{50}$ of less than about 10 μM, of less than about 1 μM, of less than about 100 nM, or of less than about 10 nM at human, mouse or rat GPR84, preferably at human, GPR84. In some embodiments, the modulator is an agonist with an $EC_{50}$ of less than a value selected from the interval of about 10 nM to 10 μm. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 μM. In some embodiments, the modulator is an agonist with an $EC_{50}$ in said assay of less than a value selected from the interval of about 10 nM to 1 μM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or agonist is orally active.

In a ninth aspect, the invention features a method of preventing or treating a condition related to MCP-1 expression comprising administering to a mammal in need thereof a therapeutically effective amount of a modulator of the mammalian GPR84 or of a pharmaceutical composition comprising the modulator and a pharmaceutically acceptable carrier or of a composition comprising the modulator.

In some embodiments, the condition related to MCP-1 expression is selected from the group consisting of atherosclerosis, an atherosclerotic disease, rheumatoid arthritis, Crohn's disease, and multiple sclerosis.

In some embodiments, the condition related to MCP-1 expression is selected from the group consisting of atherosclerosis, rheumatoid arthritis, psoriatic arthritis, osteoarthritis, ulcerative colitis, Crohn's disease, insulin resistance, Type 1 diabetes, Type 2 diabetes, metabolic syndrome, obesity, lower than normal HDL-cholesterol, hypertension, hyperlipidemia, ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, multiple sclerosis, ischemic stroke, Parkinson's disease, prion-associated disease, excitotoxic injury, mild cognitive impairment (MCI) and Alzheimer's disease.

In some embodiments, the condition related to MCP-1 expression is an inflammation-related disease or disorder.

In some embodiments, the MCP-1 expression comprises MCP-1 expression in a monocyte/macrophage.

In some embodiments, the MCP-1 expression is MCP-1 expression in a monocyte/macrophage.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ DD NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2; and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the mammal is a human.

In some embodiments, the modulator is an agonist with an $EC_{50}$ of less than about 10 μM, of less than about 1 μM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 μM. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In some embodiments, said administering is oral.

In a tenth aspect, the invention features use of a modulator of a mammalian GPR84 or of a pharmaceutical composition comprising the modulator and a pharmaceutically acceptable carrier or of a composition comprising the modulator to prevent or treat a condition related to MCP-1 expression in a human or animal body by therapy.

In some embodiments, the condition related to MCP-1 expression is selected from the group consisting of atherosclerosis, an atherosclerotic disease, rheumatoid arthritis, Crohn's disease, and multiple sclerosis.

In some embodiments, the condition related to MCP-1 expression is selected from the group consisting of atherosclerosis, rheumatoid arthritis, psoriatic arthritis, osteoarthritis, ulcerative colitis, Crohn's disease, insulin resistance, Type 1 diabetes, Type 2 diabetes, metabolic syndrome, obesity, lower than normal HDL-cholesterol, hypertension, hyperlipidemia, ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, multiple sclerosis, ischemic stroke, Parkinson's disease, prion-associated disease, excitotoxic injury, mild cognitive impairment (MCI) and Alzheimer's disease.

In some embodiments, the condition related to MCP-1 expression is an inflammation-related disease or disorder.

In some embodiments, the MCP-1 expression comprises MCP-1 expression in a monocyte/macrophage.

In some embodiments, the MCP-1 expression is MCP-1 expression in a monocyte/macrophage.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the animal is a non-human mammal.

In some embodiments, the modulator is an agonist with an $EC_{50}$ of less than about 10 µM, of less than about 1 µM, of less than about 100 nM, or of less than about 10 nM at human, mouse or rat GPR84, preferably at human GPR84. In some embodiments, the modulator is an agonist with an $EC_{50}$ of less than a value selected from the interval of about 10 nM to 10 μM. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 μM. In some embodiments, the modulator is an agonist with an $EC_{50}$ in said assay of less than a value selected from the interval of about 10 nM to 1 μM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In an eleventh aspect, the invention features a use of a modulator of a mammalian GPR84 or of a pharmaceutical composition comprising the modulator and a pharmaceutically acceptable carrier or of a composition comprising the modulator in the manufacture of a medicament for inhibiting atherogenesis in the mammal.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the mammal is a human.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the modulator is an agonist with an $EC_{50}$ of less than about 10 μM, of less than about 1 μM, of less than about 100 nM, or of less than about 10 nM. In some embodiments, the modulator is an agonist with an $EC_{50}$ of less than a value selected from the interval of about 10 nM to 10 μM. In some embodiments, modulator is an agonist with an $EC_{50}$ of less than a value selected from the interval of about 10 nM to 1 μM. In some embodiments, the modulator is an agonist with an $EC_{50}$ of less than a value selected from the interval of about 10 nM to 100 nM. In some embodiments, the modulator is an agonist with an $EC_{50}$ of less than about 10 μM, of less than about 1 μM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 μM, of less than about 1 μM, of less than about 100 nM, or of less than about 10 nM in said assay. In some embodiments, the modulator is an agonist with an $EC_{50}$ in said assay of less than a value selected from the interval of about 10 nM to 10 μM. In some embodiments, the modulator is an agonist with an $EC_{50}$ in said assay of less than a value selected from the interval of about 10 nM to 1 μM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In a twelfth aspect, the invention features use of a modulator of a mammalian GPR84 or of a pharmaceutical composition comprising the modulator and a pharmaceutically acceptable carrier or of a composition comprising the modulator in the manufacture of a medicament for preventing or treating atherosclerosis or an atherosclerotic disease in the mammal.

In certain embodiments, the medicament for preventing or treating atherosclerosis or an atherosclerotic disease is a medicament for preventing or treating atherosclerosis. In certain embodiments, the medicament for preventing or treating atherosclerosis or an atherosclerotic disease is a medicament for preventing or treating an atherosclerotic disease.

In some embodiments, the atherosclerotic disease is selected from the group consisting of coronary artery disease, myocardial infarction, peripheral arterial disease, and ischemic stroke.

In some embodiments, the modulator is according to the second aspect. In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the modulator is an agonist. In some embodiments, the agonist increases ABCA1 expression. In some embodiments, the agonist increases ABCA1 expression in a monocyte/macrophage.

In some embodiments, the mammal is a human.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the modulator is an agonist with an $EC_{50}$ of less than about 10 µM, of less than about 1 µM, of less than about 100 nM, or of less than about 10 nM. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator is orally active.

In a thirteenth aspect, the invention features use of a modulator of a mammalian GPR84 or of a pharmaceutical composition comprising the modulator and a pharmaceutically acceptable carrier or of a composition comprising the modulator in the manufacture of a medicament for preventing or treating a condition related to MCP-1 expression in the mammal.

In some embodiments, the condition related to MCP-1 expression is selected from the group consisting of atherosclerosis, an atherosclerotic disease, rheumatoid arthritis, Crohn's disease, and multiple sclerosis.

In some embodiments, the condition related to MCP-1 expression is selected from the group consisting of atherosclerosis, rheumatoid arthritis, psoriatic arthritis, osteoarthritis, ulcerative colitis, Crohn's disease, insulin resistance, Type 1 diabetes, Type 2 diabetes, metabolic syndrome, obesity, lower than normal HDL-cholesterol, hypertension, hyperlipidemia, ischemic heart disease, congestive heart failure, osteoporosis, restenosis, septic shock, ischemia/reperfusion injury, disseminated intravascular coagulation; psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, multiple sclerosis, ischemic stroke, Parkinson's disease, prion-associated disease, excitotoxic injury, mild cognitive impairment (MCI) and Alzheimer's disease.

In some embodiments, the condition related to MCP-1 expression is an inflammation-related disease or disorder.

In some embodiments, the MCP-1 expression comprises MCP-1 expression in a monocyte/macrophage.

In some embodiments, the MCP-1 expression is in a monocyte/macrophage.

In some embodiments, the modulator is according to the second aspect.

In some embodiments, the modulator of the mammalian GPR84 is a modulator of a human GPR84. In some embodiments, the modulator of the human GPR84 is a modulator of SEQ ID NO:2. In some embodiments, the modulator of the human GPR84 is a modulator of SEQ ID NO:20.

In some embodiments, the modulator is an agonist, partial agonist, inverse agonist, or antagonist of the mammalian GPR84.

In some embodiments, the modulator is a small molecule. In some embodiments, the modulator is not an antibody or an antigen-binding fragment thereof. In some embodiments, the modulator is not a polypeptide. In some embodiments, the modulator is not a lipid. In certain embodiments, the modulator is not identical to a compound in Table 1. In some embodiments, the modulator is not Compound 1, not Compound 2, and not Compound 3. In some embodiments, the modulator is not Compound 1. In some embodiments, the modulator is not Compound 2. In some embodiments, the modulator is not Compound 3. In some embodiments, the modulator is not Compound 1 or Compound 2. In some embodiments, the modulator is not Compound 1 or Compound 3. In some embodiments, the modulator is not Compound 2 or Compound 3. In certain embodiments, the modulator is non-endogenous. In certain embodiments, the modulator is not endogenous. In some embodiments, the modulator is not material that a prokaryote or eukaryote naturally produces. In some embodiments, the modulator is not material that a prokaryote naturally produces. In some embodiments, the modulator is not material that a eukaryote naturally produces.

In some embodiments, the modulator is a compound selected from Table 1. In some embodiments, the modulator is Compound 1.

In certain embodiments, the modulator of the mammalian GPR84 is an agonist of the mammalian GPR84. In some embodiments, the agonist of the mammalian GPR84 is an agonist of a human GPR84. In some embodiments, the agonist of the human GPR84 is an agonist of SEQ ID NO:2. In some embodiments, the agonist of the human GPR84 is an agonist of SEQ ID NO:20.

In some embodiments, the agonist is a small molecule. In some embodiments, the agonist is not an antibody or an antigen-binding fragment thereof. In some embodiments, the agonist is not a polypeptide. In some embodiments, the agonist is not a lipid. In certain embodiments, the agonist is not identical to a compound in Table 1. In some embodiments, the agonist is not Compound 1, not Compound 2, and not Compound 3. In some embodiments, the agonist is not Compound 1. In some embodiments, the agonist is not Compound 2. In some embodiments, the agonist is not Compound 3. In some embodiments, the agonist is not Compound 1 or Compound 2. In some embodiments, the agonist is not Compound 1 or Compound 3. In some embodiments, the agonist is not Compound 2 or Compound 3. In certain embodiments, the agonist is non-endogenous. In certain embodiments, the agonist is not endogenous. In some embodiments, the agonist is not material that a prokaryote or eukaryote naturally produces. In some embodiments, the agonist is not material that a prokaryote naturally produces. In some embodiments, the agonist is not material that a eukaryote naturally produces.

In some embodiments, the agonist is a compound selected from Table 1. In some embodiments, the agonist is Compound 1.

In some embodiments, the modulator is an agonist. In some embodiments, the agonist decreases MCP-1 expression. In some embodiments, the agonist decreases MCP-1 expression in a monocyte/macrophage.

In some embodiments, the mammal is a human.

In some embodiments, the pharmaceutical composition or the composition further comprises a compound selected from the group consisting of an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective for PDE4B2), a biologic agent for neutralizing tumor necrosis factor alpha (TNFα) activity (such as etanercept and infliximab), and CTLA4-Ig.

In some embodiments, the modulator is an agonist with an $EC_{50}$ of less than about 10 µM, of less than about 1 µM, of less than about 100 nM, or of less than about 10 nM. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than about 10 µM, of less than about 1 µM, of less than about 100 nM, or of less than about 10 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, or of less than about 10 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM.

In some embodiments, the agonist is a partial agonist.

In some embodiments, the modulator or the agonist is orally active.

In a fourteenth aspect, the invention features use of a GPCR to screen candidate compounds as pharmaceutical agents for inhibiting atherogenesis, as pharmaceutical agents for atherosclerosis or an atherosclerotic disease, or as pharmaceutical agents for a condition related to MCP-1 expression, wherein the GPCR comprises an amino acid sequence selected from the group consisting of:

(a) the amino acid sequence of SEQ ID NO:2;
(b) amino acids 2-396 of SEQ ID NO:2;
(c) amino acids 2-396 of SEQ ID NO:2, wherein the GPCR does not comprise amino acids 1-396 of SEQ ID NO:2;
(d) the amino acid sequence of SEQ ID NO:20;
(e) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
(f) the amino acid sequence of a G protein-coupled receptor encoded by a polynucleotide hybridizing under stringent conditions to the complement of SEQ ID NO:1;
(g) the amino acid sequence of an endogenous G protein-coupled receptor having at least about 75% identity, at least about 80% identity, at least about 85% identity, at least about 90% identity, or at least about 95% identity to SEQ ID NO:2;
(h) the amino acid sequence of SEQ ID NO:4;
(i) amino acids 2-396 of SEQ ID NO:4;
(j) amino acids 2-396 of SEQ ID NO:4 wherein the GPCR does not comprise amino acids 1-396 of SEQ ID NO:4;
(k) the amino acid sequence of a G protein-coupled receptor encoded by a polynucleotide hybridizing under stringent conditions to the complement of SEQ ID NO:3;
(l) the amino acid sequence of an endogenous G protein-coupled receptor having at least about 75% identity, at least about 80% identity, at least about 85% identity, at least about 90% identity, or at least about 95% identity to SEQ ID NO:4;
(m) the amino acid sequence of SEQ ID NO:6;
(n) amino acids 2-396 of SEQ ID NO:6;
(o) amino acids 2-396 of SEQ ID NO:6, wherein the GPCR does not comprise amino acids 1-396 of SEQ ID NO:6;
(p) the amino acid sequence of a G protein-coupled receptor encoded by a polynucleotide hybridizing under stringent conditions to the complement of SEQ ID NO:5; and
(q) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof.

In certain embodiments, pharmaceutical agents for atherosclerosis or an atherosclerotic disease are pharmaceutical agents for atherosclerosis. In certain embodiments, pharmaceutical agents for atherosclerosis or an atherosclerotic disease are pharmaceutical agents for an atherosclerotic disease.

In some embodiments, the atherosclerotic disease is selected from the group consisting of coronary artery disease, myocardial infarction, peripheral arterial disease, and ischemic stroke.

In some embodiments, the condition related to MCP-1 expression is selected from the group consisting of atherosclerosis, an atherosclerotic disease, rheumatoid arthritis, Crohn's disease, and multiple sclerosis.

In some embodiments, the condition related to MCP-1 expression is selected from the group consisting of atherosclerosis, rheumatoid arthritis, psoriatic arthritis, osteoarthritis, ulcerative colitis, Crohn's disease, insulin resistance, Type 1 diabetes, Type 2 diabetes, metabolic syndrome, obesity, lower than normal HDL-cholesterol, hypertension, hyperlipidemia, ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, multiple sclerosis, ischemic stroke, Parkinson's disease, prion-associated disease, excitotoxic injury, mild cognitive impairment (MCI) and Alzheimer's disease.

In some embodiments, the condition related to MCP-1 expression is an inflammation-related disease or disorder.

In a fifteenth aspect, the invention features an isolated polynucleotide encoding a G protein-coupled receptor, wherein the polynucleotide comprises a nucleic acid sequence selected from the group consisting of:
  (a) a nucleic acid sequence encoding the amino acid sequence of SEQ ID NO:6;
  (b) the nucleic acid sequence of SEQ ID NO:5;
  (c) nucleotides 4-1191 of SEQ ID NO:5;
  (d) nucleotides 1-1188 of SEQ ID NO:5;
  (e) nucleotides 4-1188 of SEQ ID NO:5;
  (f) a nucleic acid sequence hybridizing under stringent conditions to the complement of SEQ ID NO:5;
  (g) a nucleic acid sequence encoding an endogenous G protein-coupled receptor having at least about 95% identity to SEQ ID NO:6; and
  (h) a nucleic acid encoding a variant or biologically active fragment of SEQ ID NO:6;
or the complement thereof.

In some embodiments, the nucleic acid sequence encodes an endogenous rat GPCR. In some embodiments, the nucleic acid encodes an endogenous rat GPR84. In some embodiments, the nucleic acid encodes a non-endogenous version of an endogenous rat GPCR.

In a sixteenth aspect, the invention features a recombinant vector comprising an isolated polynucleotide according to the fifteenth aspect.

In some embodiments, the vector is an expression vector. In some embodiments, the expression vector is a eukaryotic expression vector. In some embodiments, the vector is an expression vector wherein the isolated polynucleotide is operably linked to a promoter.

In a seventeenth aspect, the invention features a host cell comprising a recombinant vector according to the sixteenth aspect.

In some embodiments, the host cell comprises an expression vector according to the twelfth aspect.

In some embodiments, the host cell is a eukaryotic cell. In some embodiments, the host cell is a melanophore cell. In some embodiments, the host cell is a mammalian cell. In some embodiments, the mammalian cell is a 293 cell, a 293T cell, a CHO cell or a COS-7 cell. In some embodiments, the host cell is a yeast cell.

In an eighteenth aspect, the invention features an isolated or recombinant GPCR polypeptide comprising an amino acid sequence selected from the group consisting of:
  (a) the amino acid sequence of SEQ ID NO:6;
  (b) amino acids 2-396 of SEQ ID NO:6;
  (c) amino acids 2-396 of SEQ ID NO:6, wherein the GPCR does not comprise amino acids 1-396 of SEQ ID NO:6;
  (d) the amino acid sequence of a G protein-coupled receptor encoded by a polynucleotide hybridizing under stringent conditions to the complement of SEQ ID NO:5; and
  (e) the amino acid sequence of an endogenous GPCR having at least 95% identity to SEQ ID NO:6;
or a variant or biologically active fragment thereof.

In some embodiments, the GPCR is an endogenous rat GPCR. In some embodiments, the GPCR is an endogenous rat GPR84. In some embodiments, the GPCR is non-endogenous. In some embodiments, the GPCR is a non-endogenous version of an endogenous rat GPCR.

In a nineteenth aspect, the invention features a method of making a recombinant host cell comprising the steps of:
  (a) transfecting an expression vector according to the sixteenth aspect into a suitable host cell; and
  (b) culturing the host cell under conditions which allow expression of the G protein-coupled receptor encoded by the expression vector.

In some embodiments, the host cell is a eukaryotic cell. In some embodiments, the host cell is a melanophore cell. In some embodiments, the host cell is a mammalian cell. In some embodiments, the mammalian cell is a 293 cell, a 293T cell, a CHO cell or a COS-7 cell. In some embodiments, the host cell is a yeast cell.

In a twentieth aspect, the invention features a method of identifying a candidate compound as a ligand of a GPCR, wherein the GPCR comprises an amino acid sequence selected from the group consisting of:
  (a) the amino acid sequence of SEQ ID NO:2;
  (b) amino acids 2-396 of SEQ ID NO:2;
  (h) amino acids 2-396 of SEQ ID NO:2, wherein the GPCR does not comprise amino acids 1-396 of SEQ ID NO:2;
  (i) the amino acid sequence of SEQ ID NO:20;
  (j) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
  (k) the amino acid sequence of a G protein-coupled receptor encoded by a polynucleotide hybridizing under stringent conditions to the complement of SEQ ID NO:1;
  (l) the amino acid sequence of an endogenous G protein-coupled receptor having at least about 75% identity, at least about 80% identity, at least about 85% identity, at least about 90% identity, or at least about 95% identity to SEQ ID NO:2;
  (h) the amino acid sequence of SEQ ID NO:4;
  (i) amino acids 2-396 of SEQ ID NO:4;
  (j) amino acids 2-396 of SEQ ID NO:4 wherein the GPCR does not comprise amino acids 1-396 of SEQ ID NO:4;
  (k) the amino acid sequence of a G protein-coupled receptor encoded by a polynucleotide hybridizing under stringent conditions to the complement of SEQ ID NO:3;
  (l) the amino acid sequence of an endogenous G protein-coupled receptor having at least about 75% identity, at least about 80% identity, at least about 85% identity, at least about 90% identity, or at least about 95% identity to SEQ ID NO:4;
  (m) the amino acid sequence of SEQ ID NO:6;
  (n) amino acids 2-396 of SEQ ID NO:6;
  (o) amino acids 2-396 of SEQ ID NO:6, wherein the GPCR does not comprise amino acids 1-396 of SEQ ID NO:6;
  (p) the amino acid sequence of a G protein-coupled receptor encoded by a polynucleotide hybridizing under stringent conditions to the complement of SEQ ID NO:5; and
  (q) the amino acid sequence of an endogenous G protein-coupled receptor having at least about 75% identity, at least about 80% identity, at least about 85% identity, at least about 90% identity, or at least about 95% identity to SEQ ID NO:6;
or a variant or biologically active fragment thereof;
comprising the steps of:

(a') contacting said GPCR with an optionally labeled known ligand to the GPCR in the presence or absence of the candidate compound;
(b') detecting the complex between the known ligand and said GPCR; and
(c') determining whether less of said complex is formed in the presence of the candidate compound than in the absence of the candidate compound, wherein said determination is indicative of the candidate compound being a ligand of said receptor.

In some embodiments, said contacting comprises contacting with a host cell comprising the GPCR or with a host cell membrane that comprises the GPCR, wherein said host cell comprises an expression vector comprising a polynucleotide encoding the GPCR. In certain embodiments, the host cell is a eukaryotic host cell. In some embodiments, the eukaryotic host cell is a mammalian host cell. In some embodiments, the eukaryotic host cell is a melanophore host cell. In some embodiments, the eukaryotic host cell is a yeast host cell. In some embodiments, the mammalian host cell is a non-myeloid host cell. In some embodiments, the mammalian host cell is not identical to a monocyte or to a cell derived from a monocyte. In some embodiments, the mammalian host cell is a myeloid host cell. In some embodiments, the mammalian host cell is identical a monocyte or to a cell derived from a monocyte.

In some embodiments, the known ligand to the GPCR is a known ligand to a mammalian GPR84. In some embodiments, the known ligand to the GPCR is a known ligand to a human GPR84.

In some embodiments, the known ligand to the GPCR is a known ligand to SEQ ID NO:2. In some embodiments, the known ligand to the GPCR is a known ligand to SEQ ID NO:20.

In some embodiments, the known ligand to the GPCR is a compound selected from Table 1. In some embodiments, the known ligand to the GPCR is Compound 1.

In some embodiments, the known ligand to the GPCR is a small molecule. In some embodiments, the known ligand to the GPCR is not an antibody or an antigen-binding fragment thereof. In some embodiments, the known ligand to the GPCR is not a polypeptide. In some embodiments, the known ligand to the GPCR is not a lipid. In certain embodiments, the known ligand to the GPCR is not identical to a compound in Table 1. In some embodiments, the known ligand to the GPCR is not Compound 1, not Compound 2, and not Compound 3. In some embodiments, the known ligand to the GPCR is not Compound 1. In some embodiments, the known ligand to the GPCR is not Compound 2. In some embodiments, the known ligand to the GPCR is not Compound 3. In some embodiments, the known ligand to the GPCR is not Compound 1 or Compound 2. In some embodiments, the known ligand to the GPCR is not Compound 1 or Compound 3. In some embodiments, the known ligand to the GPCR is not Compound 2 or Compound 3. In certain embodiments, the known ligand to the GPCR is non-endogenous. In certain embodiments, the known ligand to the GPCR is not endogenous. In some embodiments, the known ligand to the GPCR is not material that a prokaryote or eukaryote naturally produces. In some embodiments, the known ligand to the GPCR is not material that a prokaryote naturally produces. In some embodiments, the known ligand to the GPCR is not material that a eukaryote naturally produces.

The invention also features a method of identifying a ligand of a GPCR, wherein the GPCR comprises an amino acid sequence selected from the group consisting of:
(a) the amino acid sequence of SEQ ID NO:2;
(b) amino acids 2-396 of SEQ ID NO:2;
(c) amino acids 2-396 of SEQ ID NO:2, wherein the GPCR does not comprise amino acids 1-396 of SEQ ID NO:2;
(d) the amino acid sequence of SEQ ID NO:20;
(e) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
(f) the amino acid sequence of a G protein-coupled receptor encoded by a polynucleotide hybridizing under stringent conditions to the complement of SEQ ID NO:1;
(g) the amino acid sequence of an endogenous G protein-coupled receptor having at least about 75% identity, at least about 80% identity, at least about 85% identity, at least about 90% identity, or at least about 95% identity to SEQ ID NO:2;
(h) the amino acid sequence of SEQ ID NO:4;
(i) amino acids 2-396 of SEQ ID NO:4;
(j) amino acids 2-396 of SEQ ID NO:4 wherein the GPCR does not comprise amino acids 1-396 of SEQ ID NO:4;
(k) the amino acid sequence of a G protein-coupled receptor encoded by a polynucleotide hybridizing under stringent conditions to the complement of SEQ ID NO:3;
(l) the amino acid sequence of an endogenous G protein-coupled receptor having at least about 75% identity, at least about 80% identity, at least about 85% identity, at least about 90% identity, or at least about 95% identity to SEQ ID NO:4;
(m) the amino acid sequence of SEQ ID NO:6;
(n) amino acids 2-396 of SEQ ID NO:6;
(o) amino acids 2-396 of SEQ ID NO:6, wherein the GPCR does not comprise amino acids 1-396 of SEQ ID NO:6;
(p) the amino acid sequence of a G protein-coupled receptor encoded by a polynucleotide hybridizing under stringent conditions to the complement of SEQ ID NO:5; and
(q) the amino acid sequence of an endogenous G protein-coupled receptor having at least about 75% identity, at least about 80% identity, at least about 85% identity, at least about 90% identity, or at least about 95% identity to SEQ ID NO:6;
or a variant or biologically active fragment thereof;
comprising the steps of:
(a') contacting a test ligand with a host cell comprising said GPCR or with a host cell membrane that comprises said GPCR, under conditions which which permit interaction between said receptor and said test ligand; and
(b') detecting a ligand bound to said GPCR.

In some embodiments, the G protein-coupled receptor encoded by a polynucleotide hybridizing under stringent conditions to the complement of SEQ ID NO:1, SEQ ID NO:3 or SEQ ID NO:5 is an endogenous GPCR. In some embodiments, the G protein-coupled receptor encoded by a polynucleotide hybridizing under stringent conditions to the complement of SEQ ID NO:1, SEQ ID NO:3 or SEQ ID NO:5 can decrease a level of intracellular cAMP in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 can increase a level of intracellular $IP_3$ accumulation in a cell comprising Gq(del)/Gi chimeric G protein in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 can cause melanophore cells to undergo pigment aggregation in response to a compound selected from Table 1. In some embodiments, the G protein-coupled receptor encoded by a polynucleotide hybridizing under stringent conditions to the complement of SEQ ID NO:1, SEQ ID NO:3 or SEQ ID NO:5 which can decrease a level of intracellular cAMP, which can increase a level of intracellular IP$_3$ accumulation in a cell comprising Gq(del)/Gi chimeric G protein, or which can cause melanophore cells to undergo pigment aggregation in response to a compound selected from Table 1 exhibits a detectable level of constitutive activity. In some embodiments, the compound selected from Table 1 is Compound 1.

In a twenty-first aspect, the invention features a process for screening candidate compounds as compounds selected from the group consisting of:
 (a) modulators of atherogenesis;
 (b) modulators of MCP-1 expression;
 (c) modulators of ABCA1 expression;
 (d) compounds for inhibiting atherogenesis;
 (e) compounds for the prevention or treatment of atherosclerosis or an atherosclerotic disease; and
 (f) compounds for the prevention or treatment of a condition related to MCP-1 expression;
wherein said process comprises performing a method according to the twentieth aspect.

In certain embodiments, compounds for the prevention or treatment of atherosclerosis or an atherosclerotic disease are compounds for the prevention or treatment of atherosclerosis. In certain embodiments, compounds for the prevention or treatment of atherosclerosis or an atherosclerotic disease are compounds for the prevention or treatment of an atherosclerotic disease.

In certain embodiments, the process further comprises further identifying the identified ligand as a modulator of a mammalian GPR84. In some embodiments, the modulator of the mammalian GPR84 is an agonist, partial agonist, inverse agonist, or antagonist of the mammalian GPR84. In some embodiments, the modulator of the mammalian GPR84 is an agonist or partial agonist of the mammalian GPR84. In certain embodiments, the mammalian GPR84 is a human GPR84.

Applicant reserves the right to exclude any one or more candidate compounds from any of the embodiments of the invention. Applicant reserves the right to exclude any one or more modulators from any of the embodiments of the invention. By way of example and not limitation, Applicant reserves the right to exclude any one or more agonists from any of the embodiments of the invention. By way of example and not limitation, Applicant reserves the right to exclude Compound 1, Compound 2 and Compound 3 individually or in any combination from any of the embodiments of the invention. Applicant reserves the right to exclude any polynucleotide or polypeptide from any of the embodiments of the invention. Applicant additionally reserves the right to exclude any atherosclerotic disease or any condition related to MCP-1 expression from any of the embodiments of the invention. It is also expressly contemplated that atherosclerotic diseases of the invention can be included in an embodiment either individually or in any combination. It is also expressly contemplated that conditions related to MCP-1 expression of the invention can be included in an embodiment either individually or in any combination.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

Throughout this application, various publications, patents and published patent applications are cited. The disclosures of these publications, patents and published patent applications referenced in this application are herein incorporated by reference in their entirety into the present disclosure. Citation herein by Applicant of a publication, patent, or published patent application is not an admission by Applicant of said publication, patent, or published patent application as prior art.

This application claims the benefit of priority from the following provisional patent application, filed via U.S. Express mail with the United States Patent and Trademark Office on the indicated date: U.S. Provisional Patent Application No. 60/714,137, filed Sep. 2, 2005. The disclosure of the foregoing provisional patent application is herein incorporated by reference in its entirety.

BRIEF DESCRIPTION OF THE DRAWINGS

FIG. 1 depicts results from a primary screen of candidate compounds against a "target receptor" which is a Gsα Fusion Protein construct of an endogenous, constitutively active Gs-coupled GPCR unrelated to GPR84. Results for "Compound A" are provided in well A2. Results for "Compound "B" are provided in well G9. (See, Example 6.)

FIG. 3. A. Upregulation of GPR84 mRNA in human monocytes by TNFα. B. Upregulation of GPR84 mRNA in human monocytes by IFNγ. (See, Example 11.)

FIG. 4. Analysis of GPR84 mRNA expression in rheumatoid arthritis synovium by in situ hybridization. (See, Example 12.)

DETAILED DESCRIPTION

Definitions

Figure 1:
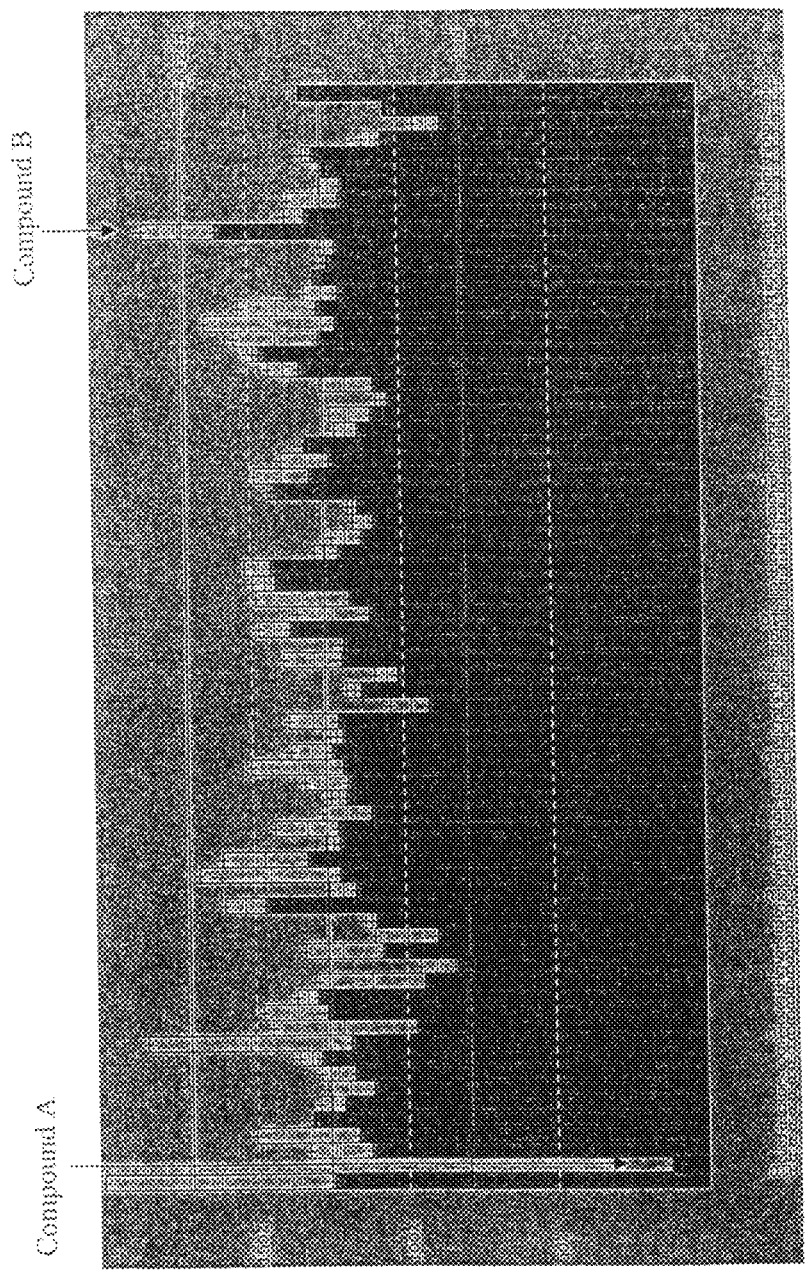
FIG. 1. By way of illustration and not limitation.

AGONIST shall mean an agent (e.g., ligand, candidate compound) that by virtue of binding to a GPCR activates the GPCR so as to elicit an intracellular response mediated by the GPCR. By way of example and not limitation, an agonist may be endogenous or non=endogenous.

AMINO ACID ABBREVIATIONS used herein are set out in Table A:

TABLE A

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONIST shall mean an agent (e.g., ligand, candidate compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An antagonist typically does not diminish the baseline intracellular response in the absence of an agonist or partial agonist. By way of example and not limitation, an antagonist may be endogenous or non-endogenous.

ANTIBODY is intended herein to encompass monoclonal antibody and polyclonal antibody. Antibodies of the present invention may be prepared by any suitable method known in the art.

ATHEROGENESIS as used herein refers to the formation of atheromatous plaques containing cholesterol and lipids on the innermost layer of the walls of large and medium-sized arteries. In some embodiments, a compound which reduces an atherosclerotic lesion area is an inhibitor of atherogenesis. In some embodiments, a compound which reduces a diameter of lipid droplets in fatty streaks is an inhibitor of atherogenesis.

ATHEROSCLEROSIS as used herein refers to a form of vascular disease characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease, including restenosis following revascularization procedures, coronary artery disease (also known as coronary heart disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

ATHEROSCLEROTIC DISEASE as used herein shall refer to vascular diseases and conditions that are recognized and understood by physicians practicing in the relevant fields of medicine, including but not limited to coronary artery disease, myocardial infarction, peripheral artery disease, and ischemic stroke. Atherosclerotic diseases may be included in embodiments of the invention individually or in any combination.

ATHEROSCLEROTIC LESION as used herein shall refer to an atheromatous plaque containing cholesterol and lipids on the innermost layer of the wall of a large or medium-sized artery.

BIOLOGICALLY ACTIVE FRAGMENT of a GPCR polypeptide or amino acid sequence shall mean a fragment of the polypeptide or amino acid sequence having structural and biochemical functions of a naturally occurring GPCR. In certain embodiments, the biologically active fragment couples to a G protein. In certain embodiments, the biologically active fragment binds to a ligand.

CANDIDATE COMPOUND shall mean a molecule (for example, and not limitation, a chemical compound) that is amenable to a screening technique and is used interchangeably herein with TEST COMPOUND. By way of example and not limitation, a candidate compound may be a compound not known to be a ligand or a modulator of a GPCR. By way of example and not limitation, a candidate compound may be endogenous or non-endogenous.

CODON shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

COMPOSITION means a material comprising at least one component.

COMPOUND EFFICACY or EFFICACY shall mean the ability of a compound to inhibit or stimulate one or more GPCR functions, e.g. by measurement of cAMP level, $IP_3$ level or $Ca^{2+}$ level in the presence or absence of a candidate compound. Exemplary means of measuring compound efficacy are disclosed in the Examples section of this patent document.

CONDITION RELATED TO MCP-1 EXPRESSION as used herein shall refer to diseases and conditions that are recognized and understood by physicians practicing in the relevant fields of medicine, including but not limited to atherosclerosis, an atherosclerotic disease, and rheumatoid arthritis. In certain embodiments, the condition related to MCP-1 expression is an inflammation-related disease or disorder. In certain embodiments, the condition related to MCP-1 expression is characterized by elevated MCP-1 expression. In some embodiments, the MCP-1 expression comprises MCP-1 expression in monocytes/macrophages. In some embodiments, the MCP-1 expression is MCP-1 expression in monocytes/macrophages. In some embodiments, the condition is related adversely to MCP-1 expression. Conditions related to MCP-1 expression may be included in embodiments of the invention individually or in any combination. In certain embodiments, the condition related to MCP-1 expression is selected from atherosclerosis, an atherosclerotic disease, rheumatoid arthritis, Crohn's disease, and multiple sclerosis.

CONSTITUTIVELY ACTIVE RECEPTOR shall mean a receptor stabilized in an active state by means other than through binding of the receptor to its ligand or a chemical equivalent thereof. A constitutively active receptor may be endogenous or non-endogenous.

CONSTITUTIVELY ACTIVATED RECEPTOR shall mean an endogenous receptor that has been modified so as to be constitutively active or to be more constitutively active.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound" or "test compound", shall mean the screening of a compound against a G protein-coupled receptor in the absence of a known ligand (e.g., a known agonist) to the G protein-coupled receptor.

ENDOGENOUS shall mean a material that a mammal naturally produces. Endogenous in reference to, for example and not limitation, the term "receptor," shall mean that which is naturally produced by a mammal (for example, and not limitation, a human). Endogenous shall be understood to encompass allelic variants of a gene as well as the allelic polypeptide variants so encoded. As used herein, "endogenous GPCR" and "native GPCR" are used interchangeably. By contrast, the term NON-ENDOGENOUS in this context shall mean that which is not naturally produced by a mammal (for example, and not limitation, a human).

EXPRESSION VECTOR shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

G PROTEIN-COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous GPCR. In the preferred form, the G protein can be fused directly to the C-terminus of the GPCR or there may be spacers between the two.

HOST CELL shall mean a cell capable of having a vector incorporated therein. In the present context, the vector will typically contain nucleic acid encoding a GPCR or GPCR fusion protein in operable connection with a suitable promoter sequence to permit expression of the GPCR or GPCR fusion protein to occur. In particular embodiment, the host cell is a eukaryotic host cell. In certain embodiments, the eukaryotic host cell is a mammalian host cell. In certain embodiments, the eukaryotic host cell is a melanophore host cell. In certain embodiments, the eukaryotic host cell is a yeast host cell.

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that a subject or animal requires or will benefit from treatment. This judgement is made based on, a variety of factors that are in the realm of a caregiver's expertise, but that include the knowledge that the subject or animal is ill, or will be ill, as the result of a condition that is treatable by the compounds of the invention.

INHIBIT or INHIBITING, in relationship to the term "response" shall mean that a response is decreased or prevented in the presence of a compound as opposed to in the absence of the compound.

INVERSE AGONIST shall mean an agent (e.g., ligand, candidate compound) which binds to either the endogenous form of a GPCR or to the constitutively activated form of a GPCR and which inhibits the baseline intracellular response initiated by the active form of the receptor below the normal base level activity which is observed in the absence of an agonist or partial agonist. By way of example and not limitation, an inverse agonist may be endogenous or non-endogenous.

LIGAND as used herein shall mean a molecule that specifically binds to a GPCR. An endogenous ligand is an endogenous molecule that binds to a native GPCR. By way of example and not limitation, a ligand may be endogenous or non-endogenous. A ligand of a GPCR may be, but is not limited to, an agonist, a partial agonist, an inverse agonist or an antagonist of the GPCR.

MCP-1 EXPRESSION as used herein shall refer to a cellular of steady-state MCP-1 mRNA or to a level of cell secreted MCP-1. In some embodiments, the cell is a monocyte/macrophage.

As used herein, the terms MODULATE or MODIFY are meant to refer to an increase or decrease in the amount, quality, or effect of a particular activity, function or molecule.

MODULATOR shall be understood to encompass agonist, partial agonist, inverse agonist and antagonist as hereinbefore defined.

MONOCYTE/MACROPHAGE as used herein is intended to encompass a monocyte, a monocyte which has differentiated toward a macrophage, and a macrophage, which is understood to include a monocyte-derived macrophage and a macrophage-derived foam cell. By way of example and not limitation, a monocyte, a monocyte-derived macrophage and a macrophage-derived foam cell may be included in embodiments of the invention relating to a MONOCYTE/MACROPHAGE individually or in any combination. A monocyte may undergo differentiation toward a macrophage either in vitro or in vivo.

PARTIAL AGONIST shall mean an agent (e.g., ligand, candidate compound) that by virtue of binding to a GPCR activates the GPCR so as to elicit an intracellular response mediated by the GPCR, albeit to a lesser extent or degree than does a full agonist. By way of example and not limitation, a partial agonist may be endogenous or non-endogenous.

PHARMACEUTICAL COMPOSITION shall mean a composition comprising at least one active ingredient, whereby the composition is amenable to investigation for a specified, efficacious outcome in a mammal (for example, and not limited to a human). Those of ordinary skill in the art will understand and appreciate the techniques appropriate for determining whether an active ingredient has a desired efficacious outcome e.g., based upon the needs of the artisan.

POLYNUCLEOTIDE shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, PEPTIDES, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

SECOND MESSENGER shall mean an intracellular response produced as a result of receptor activation. A second messenger can include, for example, inositol 1,4,5-triphosphate ($IP_3$), diacylglycerol (DAG), cyclic AMP (cAMP), cyclic GMP (cGMP), MAP kinase activity, MAPK/ERK kinase kinase-1 (MEKK1) activity, and $Ca^{2+}$. Second messenger response can be measured for a determination of receptor activation. In addition, second messenger response can be measured for the identification of candidate compounds as, for example, inverse agonists, partial agonists, agonists, and antagonists of the receptor.

SMALL MOLECULE shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 500 grams per mole.

STIMULATE or STIMULATING, in relationship to the term "response" shall mean that a response is increased in the presence of a compound as opposed to in the absence of the compound.

SUBJECT as used herein is a mammal. The mammal may be a human or it may be a non-human mammal. Non-human mammal is intended to include, but not be limited to, horse, cow, sheep, pig, cat, dog, rabbit, mouse, rat, and non-human primate. The non-human mammal may be a laboratory animal (such as a mouse, a rat, a hamster, a pig, a dog, a rabbit, etc.), a farm animal (such as a cow, a sheep, a goat, a horse, a pig, etc.), a human companion animal (such as a dog, a cat, etc.) or an exotic animal (such as an animal found in a zoo, etc.). Non-human mammals may be included in embodiments individually or in any combination. In certain embodiments, the subject is a human.

THERAPEUTICALLY EFFECTIVE AMOUNT as used herein refers to the amount of active compound or pharmaceutical agent that elicits the biological or medicinal response in a tissue, system, animal, subject or human that is being sought by a researcher, veterinarian, medical doctor or other clinician, which includes one or more of the following:

(1) Preventing the disease; for example, preventing a disease, condition or disorder in a subject that may be predisposed to the disease, condition or disorder but does not yet experience or display the pathology or symptomatology of the disease, (2) Inhibiting the disease; for example, inhibiting a disease, condition or disorder in a subject that is experiencing or displaying the pathology or symptomatology of the disease, condition or disorder (i.e., arresting further development of the pathology and/or symptomatology), and (3) Ameliorating the disease; for example, ameliorating a disease, condition or disorder in a subject that is experiencing or displaying the pathology or symptomatology of the disease, condition or disorder (i.e., reversing the pathology and/or symptomatology).

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differ in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

A. Introduction

The order of the following sections is set forth for presentational efficiency and is not intended, nor should be construed, as a limitation on the disclosure or the claims to follow.

B. Receptor Expression

1. GPCR Polypeptides of Interest

A GPCR of the invention may comprise an amino acid sequence selected from the group consisting of:

(a) the amino acid sequence of SEQ ID NO:2;
(b) amino acids 2-396 of SEQ ID NO:2;
(c) amino acids 2-396 of SEQ ID NO:2, wherein the GPCR does not comprise amino acids 1-396 of SEQ ID NO:2;
(d) the amino acid sequence of SEQ ID NO:20;
(e) the amino acid sequence of a G protein-coupled receptor encoded by a polynucleotide that is amplifiable by polymerase chain reaction (PCR) on a human DNA sample using specific primers SEQ ID NO:7 and SEQ ID NO:8;
(f) the amino acid sequence of a G protein-coupled receptor encoded by a polynucleotide hybridizing under stringent conditions to the complement of SEQ ID NO:1;
(g) the amino acid sequence of an endogenous G protein-coupled receptor having at least about 75% identity, at least about 80% identity, at least about 85% identity, at least about 90% identity, or at least about 95% identity to SEQ ID NO:2;
(h) the amino acid sequence of SEQ ID NO:4;
(i) amino acids 2-396 of SEQ ID NO:4;
(j) amino acids 2-396 of SEQ ID NO:4 wherein the GPCR does not comprise amino acids 1-396 of SEQ ID NO:4;
(k) the amino acid sequence of a G protein-coupled receptor encoded by a polynucleotide hybridizing under stringent conditions to the complement of SEQ ID NO:3;
(l) the amino acid sequence of an endogenous G protein-coupled receptor having at least about 75% identity, at least about 80% identity, at least about 85% identity, at least about 90% identity, or at least about 95% identity to SEQ ID NO:4;
(m) the amino acid sequence of SEQ ID NO:6;
(n) amino acids 2-396 of SEQ ID NO:6;
(o) amino acids 2-396 of SEQ ID NO:6, wherein the GPCR does not comprise amino acids 1-396 of SEQ ID NO:6;
(p) the amino acid sequence of a G protein-coupled receptor encoded by a polynucleotide hybridizing under stringent conditions to the complement of SEQ ID NO:5; and (q) the amino acid sequence of an endogenous G protein-coupled receptor having at least about 75% identity, at least about 80% identity, at least about 85% identity, at least about 90% identity, or at least about 95% identity to SEQ ID NO:6;

or a variant or biologically active fragment thereof.

In some embodiments, the GPCR comprising amino acids 2-396 of SEQ ID NO:2, wherein the GPCR does not comprise amino acids 1-396 of SEQ ID NO:2, is SEQ ID NO:20.

In some embodiments, the human DNA is human genomic DNA. In some embodiments, the human DNA is human cDNA derived from a tissue or cell type that expresses GPR84. In some embodiments, the human cDNA is derived from a leukocyte. In some embodiments, the human cDNA is derived from a monocyte/macrophage. In some embodiments, the human cDNA is derived from a granulocyte. In some embodiments the G protein-coupled receptor encoded by the polynucleotide that is amplifiable by polymerase chain reaction is an endogenous G protein-coupled receptor. In some embodiments the G protein-coupled receptor encoded by the polynucleotide that is amplifiable by polymerase chain reaction is a mammalian endogenous G protein-coupled receptor. In some embodiments the G protein-coupled receptor encoded by the polynucleotide that is amplifiable by polymerase chain reaction is an endogenous G protein-coupled receptor for which Compound 1 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments the G protein-coupled receptor encoded by the polynucleotide that is amplifiable by polymerase chain reaction is an endogenous G protein-coupled receptor for which Compound 2 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments the G protein-coupled receptor encoded by the polynucleotide that is amplifiable by polymerase chain reaction is an endogenous G protein-coupled receptor for which Compound 3 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM.

In some embodiments, a GPCR of the invention is recombinant. In some embodiments, the recombinant GPCR is recombinant human GPR84. In some embodiments, recombinant human GPR84 has SEQ ID NO:2. In some embodiments, the recombinant GPCR is a non-endogenous version of a human GPR84, wherein the non-endogenous version has SEQ ID NO:20.

In some embodiments, a GPCR of the invention is endogenous.

In some embodiments, a GPCR of the invention is a mammalian GPR84.

In some embodiments, a GPCR of the invention is constitutively active. In some embodiments, an endogenous GPCR of the invention is constitutively active. In some embodiments, a mammalian GPR84 of the invention is constitutively active. In some embodiments, the mammalian GPR84 is human GPR84. In some embodiments, the human GPR84 is SEQ ID NO:2 or an allele thereof.

In some embodiments, a GPCR of the invention exhibits a detectable level of constitutive activity. In some embodiments, an endogenous. GPCR of the invention exhibits a detectable level of constitutive activity. In some embodiments, a mammalian GPR84 of the invention exhibits a detectable level of constitutive activity. In some embodiments, the mammalian GPR84 is human GPR84. In some embodiments, the human GPR84 is SEQ ID NO:2 or an allele thereof.

By way of illustration and not limitation, deletion of an N-terminal methionine residue or an N-terminal signal peptide is envisioned to provide a biologically active fragment that may be used in the subject invention. In some embodiments, a biologically active fragment of the invention is a fragment optionally fused at its N-terminus to a peptide comprising an N-terminal methionine residue and an HA epitope tag (from hemagglutinin influenza virus). In some embodiments, a biologically active fragment of the invention is a fragment that can decrease a level of intracellular cAMP in response to a compound selected from Table 1. In some embodiments, a biologically active fragment of the invention is a fragment that can increase a level of intracellular $IP_3$ accumulation in a cell comprising Gq(del)/Gi chimeric G protein in response to a compound selected from Table 1. In some embodiments, a biologically active fragment of the invention is a fragment that can cause melanophore cells to undergo pigment aggregation in response to a compound selected from Table 1. In some embodiments, the compound selected from Table 1 is Compound 1. In some embodiments, a biologically active fragment is a fragment optionally fused at its N-terminus to a peptide comprising an N-terminal methionine residue and an HA epitope tag (from hemagglutinin influenza virus) for which Compound 1 is an agonist having an $EC_{50}$ value at said fragment optionally fused at its N-terminus to said peptide in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, a biologically active fragment is a fragment optionally fused at its N-terminus to a peptide comprising an N-terminal methionine residue and an HA epitope tag (from hemagglutinin influenza virus) for which Compound 2 is an agonist having an $EC_{50}$ value at said fragment optionally fused at its N-terminus to said peptide in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, a biologically active fragment is a fragment optionally fused at its N-terminus to a peptide comprising an N-terminal methionine residue and an HA epitope tag (from hemagglutinin influenza virus) for which Compound 3 is an agonist having an $EC_{50}$ value at said fragment optionally fused at its N-terminus to said peptide in melanophore assay according to Example 9, infra, of less than about 10 µM, less than about 5 µM, less than about 1 nM, less than about 100 nM, less than about 50 nM, less than about 25 nM, less than about 10 nM, or less than about 5 nM.

An allelic variant of human GPR84 of SEQ ID NO:2, of mouse GPR84 of SEQ ID NO:4, or of rat GPR84 of SEQ ID NO:6 is envisioned to be within the scope of the invention. In some embodiments, a GPCR that may be used in the subject methods may comprise an allelic variant of SEQ NO:2.

A variant which is a mammalian ortholog of human GPR84 of SEQ ID NO:2 is envisioned to be within the scope of the invention. By way of illustration and not limitation, additional to mouse GPR84 and rat GPR84, chimpanzee GPR84 (GenBank® Accession No. XP_522412) and cow GPR84

(GenBank® Accession No. AAX31354) are envisioned to be within the scope of the invention.

By way of example and not limitation, a variant of SEQ ID NO:2, SEQ ID NO:4 or SEQ ID NO:6 may be a polypeptide having any number of amino acid substitutions, amino acid deletions, or amino acid additions at any position in SEQ ID NO:2, SEQ ID NO:4 or SEQ ID NO:6 (e.g., the C- or N-terminus, or at internal positions).

A variant of SEQ ID NO:2, SEQ ID NO:4 or SEQ ID NO:6 having at least about 75%, at least about 80%, at least about 85%, at least about 90%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% identity to SEQ ID NO:2, SEQ ID NO:4 or SEQ ID NO:6, respectively, is envisioned to be within the scope of the invention. In some embodiments, said variant is a variant of SEQ ID NO:2. In some embodiments, the variant which is a variant of SEQ ID NO:2, SEQ ID NO:4 or SEQ ID NO:6 is an endogenous GPCR. In some embodiments, the variant can decrease a level of intracellular cAMP in response to a compound selected from Table 1. In some embodiments, the variant can increase a level of intracellular $IP_3$ accumulation in a cell comprising Gq(del)/Gi chimeric G protein in response to a compound selected from Table 1. In some embodiments, the variant can cause melanophore cells to undergo pigment aggregation in response to a compound selected from Table 1. In some embodiments, the variant which can decrease a level of intracellular cAMP, which can increase a level of intracellular $IP_3$ accumulation in a cell comprising Gq(del)/Gi chimeric G protein, or which can cause melanophore cells to undergo pigment aggregation in response to a compound selected from Table 1 exhibits a detectable level of constitutive activity. In some embodiments, the compound selected from Table 1 is Compound 1. In some embodiments, the variant is a GPCR for which Compound 1 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, the variant is a GPCR for which Compound 2 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, the variant is a GPCR for which Compound 3 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. Percent identity can be determined conventionally using known computer programs.

In certain embodiments, a variant GPCR that may be used in the subject methods has an amino acid sequence having at least about 75%, at least about 80%, at least about 85%, at least about 90%, at least about 95%, of at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9% identity to SEQ ID NO:2. By a variant GPCR having, for example, 95% "identity" to SEQ ID NO:2 is meant that the amino acid sequence of the variant is identical to amino acids 1-396 of SEQ ID NO:2 except that it may include up to five amino acid alterations per each 100 amino acids of amino acids SEQ ID NO:2. Thus, to obtain for example an amino acid sequence having at least 95% identity to the amino acid sequence of SEQ ID NO:2, up to 5% (5 of 100) of the amino acid residues in the sequence may be inserted, deleted, or substituted with another amino acid compared with amino acids 1-396 of SEQ ID NO:2. These alternations may occur at the amino or carboxy termini or anywhere between those terminal positions, interspersed either subjectly among residues in the sequence or in one or more contiguous groups within the sequence.

In some embodiments, a variant GPCR that may be used in the subject methods is a GPCR encoded by a polynucleotide hybridizing under stringent conditions to the complement of SEQ ID NO:1, SEQ ID NO:3 or SEQ ID NO:5. In some embodiments, the polynucleotide hybridizes under stringent conditions to the complement of SEQ ID NO:1. In some embodiments, the variant is an endogenous GPCR. In some embodiments, the variant can decrease a level of intracellular cAMP in response to a compound selected from Table 1. In some embodiments, the variant can increase a level of intracellular $IP_3$ accumulation in a cell comprising Gq(del)/Gi chimeric G protein in response to a compound selected from Table 1. In some embodiments, the variant can cause melanophore cells to undergo pigment aggregation in response to a compound selected from Table 1. In some embodiments, the variant which can decrease a level of intracellular cAMP, which can increase a level of intracellular $IP_3$ accumulation in a cell comprising Gq(del)/Gi chimeric G protein, or which can cause melanophore cells to undergo pigment aggregation in response to a compound selected from Table 1 exhibits a detectable level of constitutive activity. In some embodiments, the compound selected from Table 1 is Compound 1. In some embodiments, the variant is a GPCR for which Compound 1 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, the variant is a GPCR for which Compound 2 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. In some embodiments, the variant is a GPCR for which Compound 3 is an agonist having an $EC_{50}$ value at said receptor in melanophore assay according to Example 9, infra, of less than about 10 µM, less than about 5 µM, less than about 1 µM, less than about 100 nM, less than about 50 nM, less than about 25 nM, less than about 10 nM, or less than about 5 nM. Hybridization techniques are well known to the skilled artisan. In some embodiments, stringent hybridization conditions include overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by washing the filter in 0.1×SSC at about 50° C., at about 55° C., at about 60° C. or at about 65° C.

a. Sequence identity

A preferred method for determining the best overall match between a query sequence (e.g., the amino acid sequence of SEQ ID NO:2) and a sequence to be interrogated, also referred to as a global sequence alignment, can be determined using the FASTDB computer program based on the algorithm of Brutlag et al. [Comp App Biosci (1990) 6:237-245; the disclosure of which is herein incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only querey amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula, Renilla reniformis* or *Renilla muelleri*), or light emitting variants thereof. Other suitable reporter domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques. By way of example and not limitation, a variant of SEQ ID NO:5 may be a polynucleotide having any number of nucleotide substitutions, nucleotide deletions, or nucleotide additions at any position in SEQ ID NO:5 (e.g., the 5- or 3-terminus, or at internal positions).

For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8).

In some embodiments, the codons of the nucleic acids encoding polypeptides of interest are optimized for expression in, cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell. One suitable vector is pCMV, which is used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. The expression vector may be adenoviral. An exemplary adenoviral vector may be purchased as AdEasy™ from Qbiogene (Carlsbad, Calif.) [He T C et al, Proc Natl Acad Sci USA (1998) 95:2509-2514; and U.S. Pat. No. 5,922,576; the disclosure of each of which is herein incorporated by reference in its entirety]. Other suitable expression vectors will be readily apparent to those of ordinary skill in the art.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, *Cell* 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol. Pharmacol. 1999 56:1182-91; Ramsay et al., Br. J. Pharmacology, 2001, 315-323) and will not be described any further. It is expressly contemplated that such a fusion protein may contain a heterologous N-terminal domain (e.g., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites; multiple cloning sites, primer binding sites, ligatable ends, recombination sites etc., usually in order to facilitate the construction of a nucleic acid encoding a polypeptide of interest.

b. Host Cells

The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example, a yeast cell, a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); and mouse L cells (ATCC CCL-1).

In certain embodiments, melanophores are used. Melanophores are skin cells found in lower vertebrates. Relevant materials and methods will be followed according to the disclosure of U.S. Pat. No. 5,462,856 and U.S. Pat. No. 6,051,386. These patent disclosures are herein incorporated by reference in their entirety.

Additional cell lines will become apparent to those of ordinary skill in the art, and a wide variety of cell lines are available from the American Type Culture Collection, 10801 University Boulevard, Manassas, Va. 20110-2209.

C. Screening of Candidate Compounds

1. Generic GPCR Screening Assay Techniques

When a G protein receptor becomes active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. A preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid PIP$_2$, releasing two intracellular messengers: diacylglycerol (DAG) and inositol 1,4,5-triphosphate (IP$_3$). Increased accumulation of IP$_3$ is associated with activation of Gq- and Go-associated receptors. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Assays that detect IP$_3$ accumulation can be utilized to determine if a candidate compound is, e.g., an inverse agonist to a Gq- or Go-associated receptor (i.e., such a compound would decrease the levels of IP$_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian or a melanophore expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the GPCR. The GPCR Fusion Protein may be preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments, it is preferred that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 4(a) below) be available for insertion of a GPCR sequence therein; this provides for further efficiency in the context of large-scale screening of a variety of different GPCRs having different sequences.

As noted above, activated GPCRs that couple to Gi, Gz and Go are expected to inhibit the formation of cAMP making assays based upon these types of GPCRs challenging [i.e., the cAMP signal decreases upon activation, thus making the direct identification of, e.g., agonists (which would further decrease this signal) challenging]. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE B

| G protein | Effect on cAMP Production upon Activation of GPCR (i.e., constitutive activation or agonist binding) | Effect on IP$_3$ Accumulation upon Activation of GPCR (i.e., constitutive activation or agonist binding) | Effect on cAMP Production upon contact with an Inverse Agonist | Effect on IP$_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will force the endogenous Gi coupled receptor to couple to its non-endogenous G protein, Gq, such that the second messenger, for example, inositol triphosphate or diacylglycerol, can be measured in lieu of cAMP production.

4. Co-Transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In certain embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g., TSHR-A6231; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

D. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments, direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of subject members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the subject library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

In some embodiments, the candidate compound is a polypeptide. In some preferred embodiments, the candidate compound is a small molecule.

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

In certain embodiments, a modulator of the invention is orally active. A number of computational approaches available to those of ordinary skill in the art have been developed for prediction of oral bioavailability of a drug [Ooms et al., Biochim Biophys Acta (2002) 1587:118-25; Clark & Grootenhuis, Curr Opin Drug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). Furthermore, positron emission tomography (PET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety]. In some embodiments, a modulator of the invention is orally active.

In certain embodiments, modulator of the invention which is orally active is not able to cross the blood-brain barrier. In certain embodiments, modulator of the invention which is orally active is able to cross the blood-brain barrier. A number of computational approaches available to those of ordinary skill in the art have been developed for prediction of the permeation of the blood-brain barrier [Ooms et al., Biochim Biophys Acta (2002) 1587:118-25; Clark & Grootenhuis, Curr Opin Drug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is herein incorporated by reference in its entirety). A number of in vitro methods have been developed to predict blood-brain barrier permeability of drugs [Lohmann et al., J Drug Target (2002) 10:263-76; Hansen et al., J Pharm Biomed Anal (2002) 27:945-58; Otis et al., J Pharmacol Toxicol Methods (2001) 45:71-7; Dehouck et al, J Neurochem (1990) 54:1798-801; the disclosure of each of which is herein incorporated by reference in its entirety]. Furthermore, a number of strategies have been developed to enhance drug delivery across the blood-brain barrier [Scherrmann, Vascul Pharmacol (2002) 38:349-54; Pardridge, Arch Neurol (2002) 59:35-40; Pardridge, Neuron (2002) 36:555-8; the disclosure of each of which is hereby incorporated by reference in its entirety]. Finally, positron emission tomography (PET) has been successfully used by a number of groups to obtain direct measurements of drug distribution, including that within brain, in the mammalian body, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is herein incorporated by reference in its entirety].

In some embodiments, said modulator is selective for GPR84, wherein a modulator selective for GPR84 is understood to refer to a modulator having selectivity for GPR84 over one or more closely related receptors, such as GPR88 (GenBank® Accession No. NP_071332). In certain embodiments, a GPR84 selective, modulator is a GPR84 selective agonist having a selectivity for GPR84 over GPR88 of at least about 100-fold. In some preferred embodiments, GPR84 is human GPR84.

In some embodiments, the modulator is an agonist with an $EC_{50}$ of less than about 10 µM, of less than about 1 mM, of less than about 100 nM, of less than about 10 nM, or of less than about 1 nM. In some embodiments, the modulator is an agonist with an $EC_{50}$ of less than a value selected from the interval of about 10 nM to 10 µM. In some embodiments, modulator is an agonist with an $EC_{50}$ of less than a value selected from the interval of about 10 nM to 1 µM. In some embodiments, the modulator is an agonist with an $EC_{50}$ of less than a value selected from the interval of about 10 nM to 100 nM. In some embodiments, the modulator is an agonist with an $EC_{50}$ of less than a value selected from the interval of about 1 nM to 10 µM. In some embodiments, modulator is an agonist with an $EC_{50}$ of less than a value selected from the interval of about 1 nM to 1 µM. In some embodiments, the modulator is an agonist with an $EC_{50}$ of less than a value selected from the interval of about 1 nM to 100 nM. In some embodiments, the modulator is an agonist with an $EC_{50}$ of less than a value selected from the interval of about 1 nM to 10 nM. In some embodiments, the modulator is an agonist with an $EC_{50}$ of less than about 10 µM, of less than about 1 µM, of less than about 100 nM, of less than about 10 nM, or of less than about 1 nM in GTPγS binding assay carried out with membrane from transfected CHO cells, or in pigment aggregation assay carried out in transfected melanophores, or in cAMP assay carried out in transfected 293 cells, or in $IP_3$ assay carried out in transfected 293 cells comprising Gq(del)/Gi chimeric G protein, wherein the transfected CHO cells or the transfected melanophore cells or the transfected 293 cells express a recombinant GPR84 having an amino acid sequence selected from SEQ ID NO:20, SEQ ID NO:2, SEQ ID NO:4 and SEQ ID NO:6. In some embodiments, the recombinant GPR84 has the amino acid sequence of SEQ ID NO:20. In some embodiments, the recombinant GPR84 has the amino acid sequence of SEQ ID NO:2. In some embodiments, the modulator is an agonist with an $EC_{50}$ of less than about 10 µM, of less than about 1 µM, of less than about 100 nM, of less than about 10 nM, or of less than about 1 nM in said assay. In some embodiments, said modulator is an agonist with an $EC_{50}$ of less than 10 µM in said assay, of less than 9 µM in said assay, of less than 8 µM in said assay, of less than 7 µM in said assay, of less than 6 µM in said assay, of less than 5 µM in said assay, of less than 4 µM in said assay, of less than 3 µM in said assay, of less than 2 µM in said assay, of less than 1 µM in said assay, of less than 900 nM in said assay, of less than 800 nM in said assay, of less than 700 nM in said assay, of less than 600 nM in said assay, of less than 500 nM in said assay, of less than 400 nM in said assay, of less than 300 nM in said assay, of less than 200 nM in said assay, of less than 100 nM in said assay, of less than 90 nM in said assay, of less than 80 nM in said assay, of less than 70 nM in said assay, of less than 60 nM in said assay, of less than 50 nM in said assay, of less than 40 nM in said assay, of less than 30 nM in said assay, of less than 20 nM in said assay, of less than 10 nM, of less than 9 nM in said assay, of less than 8 nM in said assay, of less than 7 nM in said assay, of less than 6 nM in said assay, of less than 5 nM in said assay, of less than 4 nM n said assay, of less than 3 nM in said assay, of less than 2 nM in said assay, or of less than 1 nM in said assay. In some embodiments, the modulator is an agonist with an $EC_{50}$ in said assay of less than a value selected from the interval of about 10 nM to 10 µM. In some embodiments, the modulator is an agonist with an $EC_{50}$ in said assay of less than a value selected from the interval of about 10 nM to 1 µM. In some embodiments, the modulator is an agonist with an $EC_{50}$ in said assay of less than a value selected from the interval of about 10 nM to 100 nM. In some embodiments, the modulator is an agonist with an $EC_{50}$ in said assay of less than a value selected from the interval of about 1 nM to 10 µM. In some embodiments, the modulator is an agonist with an $EC_{50}$ in said assay of less than a value selected from the interval of about 1 nM to 1 µM. In some embodiments, the modulator is an agonist with an $EC_{50}$ in said assay of less than a value selected from the interval of about 1 nM to 100 nM. In some embodiments, the modulator is an agonist with an $EC_{50}$ in said assay of less than a value selected from the interval of about 1 nM to 10 nM.

E. Compounds of the Invention

Certain aspects of the present invention pertain to a compound selected from Table 1. The compounds in Table 1 can be obtained from commercial sources or can be prepared by one of skill in the art by synthetic methods.

TABLE 1

| Cmpd No. | Chemical Structure | Chemical Name |
|---|---|---|
| 1 | 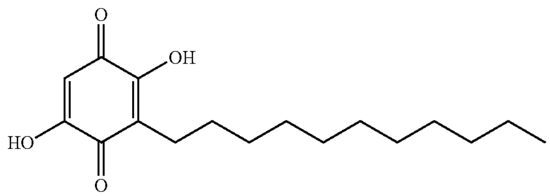 [SMILES: CCCCCCCCCCCC1=C(O)C(=O)C=C(O)C1=O] | 2,5-Dihydroxy-3-undecyl-[1,4]benzoquinone |
| 2 | 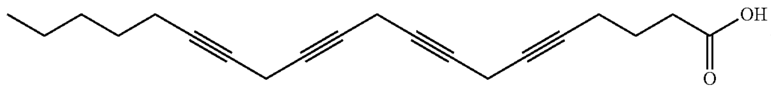 [SMILES: CCCCCC#CCC#CCC#CCC#CCCCC(=O)O] | Icosa-5,8,11,14-tetraynoic acid |
| 3 | 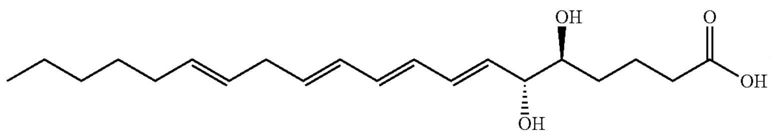 [SMILES: CCCCC/C=C/C/C=C/C=C/C=C/[C@@H](O)[C@@H](O)CCCC(=O)O] | 5S,6R-Dihydroxy-icosa-7,9,11,14-tetraenoic acid |

Additionally, compounds of the invention, including those illustrated in Table 1, encompass all pharmaceutically acceptable salts, solvates, and hydrates thereof. See, e.g., Berge et al, Journal of Pharmaceutical Sciences (1977) 66:1-19; and Polymorphism in Pharmaceutical Solids (1999) Brittain, ed., Marcel Dekker, Inc.; the disclosure of each of which is herein incorporated by reference in its entirety.

F. Pharmaceutical Compositions

Compounds of the invention can be formulated into pharmaceutical compositions using techniques well known in the art. By way of example and not limitation, compounds of the invention include but are not limited to modulators of a mammalian GPR84 (including but not limited to agonists, partial agonists, antagonists and inverse agonists of a mammalian GPR84) and ligands of a mammalian GPR84.

The invention provides methods of treatment (and prevention) by administration to a subject in need of said treatment or prevention) a therapeutically effect amount of a modulator of the invention [also see, e.g., PCT Application Number PCT/IB02/01461 published as WO 02/066505 on 29 Aug. 2002; the disclosure of each of which is herein incorporated by reference in its entirety]. In a preferred aspect, the modulator is an agonist. In a preferred aspect, the modulator is substantially purified. The subject is a mammal including, but not limited to cows, pigs, horses, chickens, non-human primates, cats, dogs, rabbits, rats, mice, etc., and is preferably a human.

Modulators of the invention can be administered to non-human mammals [see Examples, infra] and/or humans, alone or in pharmaceutical compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical composition is then provided at a therapeutically effective dose. A therapeutically effective dose refers to that amount of a modulator sufficient to result in prevention or amelioration of symptoms or physiological status of a disorder as determined illustratively and not by limitation by the methods described herein, wherein the prevention or amelioration of symptoms or physiological status of a disorder includes but is not limited to inhibiting atherogenesis, treating or preventing atherosclerosis or an atherosclerotic disease, and treating or preventing a condition related to MCP-1 expression.

It is expressly considered that the modulators of the invention may be provided alone or in combination with other pharmaceutically or physiologically acceptable compounds. Other compounds for the treatment of disorders of the invention, wherein the treatment of disorders of the invention includes but is not limited to inhibiting atherogenesis, treating or preventing atherosclerosis or an atherosclerotic disease, and treating or preventing a condition related to MCP-1 expression.

Combination Therapy

While the compounds of the invention can be administered as the sole active pharmaceutical agent (i.e., mono-therapy), compounds of the invention can also be used in combination with other pharmaceutical agents (i.e., combination-therapy) for the treatment of the diseases/conditions/disorders described herein. Therefore, another aspect of the present invention includes methods of treatment comprising administering to a subject in need of treatment a therapeutically effective amount of an agonist of the present invention in combination with one or more additional pharmaceutical agent as described herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the treatment diseases, conditions or disorders of the present invention in a subject.

Some embodiments of the present invention include methods of treatment of a disease, disorder or condition as described herein comprising administering to a subject in need of such treatment a therapeutically effect amount or dose of a compound of the present invention in combination with at least one pharmaceutical agent selected from the group consisting of: an HMG-CoA reductase inhibitor, cholesterol-lowering drugs (for example, fibrates that include: fenofibrate, bezafibrate, gemfibrozil, clofibrate and the like; bile acid sequestrants which include: cholestyramine, colestipol and the like; and niacin and analogs thereof or other such compound having agonist or partial agonist activity at the nicotinic acid receptor GPR109A), anti-lipolytic agents (for example, niacin and analogs thereof or other such compound having agonist or partial agonist activity at the nicotinic acid receptor GPR109A), and inflammation-lowering drugs. Compounds having agonist or partial agonist activity at the nicotinic acid receptor GPR109A are known in the art and include compounds disclosed in PCT/US2003/032174 (published as WO 2004/032938), PCT/US2004/018389 (published as WO 2005/011677), PCT/US2004/038920 (published as WO 2005/051937), and PCT/US2005/046599 (published as WO 2006/069242). In certain embodiments, the compounds having agonist or partial agonist activity at the nicotinic acid receptor GPR109A are orally active. In some embodiments, methods of the present invention include compounds of the present invention and the pharmaceutical agents are administered separately. In further embodiments, compounds of the present invention and the pharmaceutical agents are administered together.

Suitable pharmaceutical agents that can be used in conjunction with compounds of the present invention include the HMG-CoA reductase inhibitors. In certain embodiments, the HMG-CoA reductase inhibitor is orally active. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower plasma LDL-cholesterol concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Other treatments for one or more of the diseases cited herein include the use of pharmaceutical agents known in the art belonging to the classes of drugs referred to, but not limited to, the following: acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Additional suitable pharmaceutical agent that can be used in conjunction with compounds of the present invention comprises the combination of ezetimibe and simvastatin.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

Other suitable pharmaceutical agents that can be used in conjunction with compounds of the present invention include nonsteroidal anti-inflammatory drug (e.g., celecoxib, rofecoxib), aminosalicylate (e.g., sulfasalazine, mesalamine, azodisalicylate, balsalazide), hydroxychoroquine, aurothioglucose, sodium-aurothiomalate, auranofin, penicillamine, leflunomide, corticosteroid (e.g., prednisone, prednisolone, budesonide, hydrocortisone, methylprednisolone), immunosuppressant (e.g., azathioprine, cyclosporine, methotrexate, 6-mercaptopurine), and biologic agent (e.g., etanercept, infliximab, or other such biologic agent for neutralizing tumor necrosis factor alpha (TNFα) activity; e.g., adiponectin or an analog thereof, or other such biologic agent having agonist or partial agonist activity at adiponectin receptor AdipoR1 or AdipoR2; e.g., interleukin-10 (IL-10); e.g., CTLA4-Ig (inclusive of abatacept)). Additionally, it is expressly contemplated that the modulators of the invention, e.g. agonists and partial agonists of the invention, may be provided alone or in combination with a phosphodiesterase (PDE) inhibitor (inclusive of an inhibitor selective for type 4 cAMP-specific PDE (PDE4), e.g. roflumilast; an inhibitor selective for PDE4B; and an inhibitor selective for PDE4B2). PDE4 inhibitors are known in the art and include compounds disclosed in U.S. Pat. Nos. 7,087,634, 7,087,625, 7,022,696, 6,953,810, 6,919,353 and 6,894,041.

In particular embodiment, a compound of the invention (e.g. an agonist or partial agonist of a mammalian GPR84) is used in combination with an HMG-CoA reductase inhibitor (i.e. a statin), an agonist or partial agonist of the nicotinic acid receptor GPR109A (e.g. niacin), adiponectin or an orally active analog thereof (including orally active agonists or partial agonists of adiponectin receptor AdipoR1 or AdipoR2), methotrexate, a phosphodiesterase (PDE) inhibitor (inclusive of an inhibitor selective for type 4 cAMP-specific PDE (PDE4), e.g. roflumilast, or an inhibitor selective for PDE4B, or an inhibitor selective, for PDE4B2), a biologic agent for neutralizing tumor necrosis factor alpha (TNFα) activity (such as etanercept and infliximab), or CTLA4-Ig.

In accordance to an aspect of the present invention, a compound of the present invention can be used in combination with a pharmaceutical agent or agents belonging to one or more of the classes of drugs cited herein. In certain embodiments, it is expressly contemplated that the pharmaceutical agent belonging to one or more of the classes of drugs cited herein is orally active.

Routes of Administration

Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In certain embodiments, route of administration is oral.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in multi-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). Other controlled release systems are discussed in the review by Langer (1990, Science 249: 1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount (of a compound of the invention, e.g. an agonist or partial agonist of a mammalian GPR84, or of a combination comprising said compound) means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to decrease MCP-1 expression or to increase ABCA1 expression in monocyte/macrophage assay. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the subject physician in view of the patient's condition. (See, e.g., Fingl et al., 1975, in "The Pharmacological Basis of Therapeutics", Ch. 1).

Dosage amount and interval may be adjusted subjectly to provide plasma levels of the active compound which are sufficient to prevent or treat a disorder of the invention, depending on the particular situation. Dosages necessary to achieve these effects will depend on subject characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention. Said desired results include, but are not limited to, inhibiting atherogenesis, treating or preventing atherosclerosis or an atherosclerotic disease, and treating or preventing a condition related to MCP-1 expression.

G. Methods of Treatment

The invention is drawn inter alia to methods including, but not limited to, methods of inhibiting atherogenesis, of treating or preventing atherosclerosis or an atherosclerotic disease, and of treating or preventing a condition related to MCP-1 expression, comprising administering to a subject in need of said inhibiting, treating or preventing with a modulator of the invention. In some embodiments, the preventing or treating atherosclerosis or an atherosclerotic disease is preventing or treating atherosclerosis. In some embodiments, the preventing or treating atherosclerosis or an atherosclerotic disease is preventing or treating an atherosclerotic disease. In some embodiments, the modulator is an agonist. In some embodiments, the agonist is a partial agonist. In some embodiments, said modulator is orally active. In some embodiments, said orally active modulator is further able to cross the blood-brain barrier. In some embodiments, said orally active modulator is not able to cross the blood-brain barrier. In some embodiments, the modulator is administered to the subject in a pharmaceutical composition. In some embodiments, the modulator is provided to the subject in a pharmaceutical composition. In some embodiments, the modulator is provided to the subject in a pharmaceutical composition that is taken orally. In some embodiments, the subject is a non-human mammal. In some embodiments, the subject is a mammal. In certain embodiments, the mammal is a non-human primate. In certain preferred embodiments, the subject or mammal is a human.

In some embodiments, the subject is in need of having atherogenesis inhibited. In some embodiments, the subject is in need of preventing or treating atherosclerosis or an atherosclerotic disease. In some embodiments, the subject is in need of preventing or treating a condition related to MCP-1 expression.

In some embodiments, the atherosclerotic disease is selected from the group consisting of coronary artery disease, myocardial infarction, peripheral artery disease, and ischemic stroke. Atherosclerotic diseases may be included in embodiments of the invention individually or in any combination.

In some embodiments, the condition related to MCP-1 expression is selected from the group consisting of atherosclerosis, an atherosclerotic disease, rheumatoid arthritis, Crohn's disease, and multiple sclerosis. Conditions related to MCP-1 expression may be included in embodiments of the invention individually or in any combination.

In some embodiments, the condition related to MCP-1 expression is selected from the group consisting of atherosclerosis, arthritis (inclusive of rheumatoid arthritis, psoriatic arthritis and osteoarthritis), inflammatory bowel disease (inclusive of ulcerative colitis and Crohn's disease), a metabolic-related disorder (inclusive of insulin resistance, diabetes (inclusive of Type 1 diabetes and Type 2 diabetes), metabolic syndrome, obesity, lower than normal HDL-cholesterol, hypertension and hyperlipidemia), ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, and a neuroinflammatory disorder (inclusive of multiple sclerosis, ischemic stroke, Parkinson's disease, prion-associated disease, excitotoxic injury, mild cognitive impairment (MCI) and Alzheimer's disease). Conditions related to MCP-1 expression may be included in embodiments of the invention individually or in any combination.

In some embodiments, the condition related to MCP-1 expression is an inflammation-related disease or disorder. In some embodiments, the condition related to MCP-1 is an inflammation-related disease or disorder selected from the group consisting of atherosclerosis, arthritis (inclusive of rheumatoid arthritis, psoriatic arthritis and osteoarthritis), inflammatory bowel disease (inclusive of ulcerative colitis and Crohn's disease), a metabolic-related disorder (inclusive of insulin resistance, diabetes (inclusive of Type 1 diabetes and Type 2 diabetes), metabolic syndrome, obesity, lower than normal HDL-cholesterol, hypertension, and hyperlipidemia), ischemic heart disease, congestive heart failure, osteoporosis, restenosis, septic shock, ischemia/reperfusion injury, disseminated intravascular coagulation, psoriasis, allergic inflammation, asthma, systemic lupus erythematosus, acute transplant rejection, chronic hepatitis, interstitial lung disease, idiopathic pulmonary fibrosis, bronchiolitis obliterans syndrome, interstitial nephritis, hepatic steatosis, chronic obstructive pulmonary disease, higher than normal osteoclastogenesis, and a neuroinflammatory disorder (inclusive of multiple sclerosis, ischemic stroke, Parkinson's disease, prion-associated disease, excitotoxic injury, mild cognitive impairment (MCI) and Alzheimer's disease). Conditions related to MCP-1 expression that are inflammation-related disorders may be included in embodiments of the invention individually or in any combination.

I. Other Utility

Agents that modulate (i.e., increase, decrease, or block) receptor functionality of a GPCR of the invention such as a mammalian GPR84 may be identified by contacting a candidate compound with the GPCR and determining the effect of the candidate compound on receptor functionality. The selectivity of a compound that modulates the functionality of a mammalian GPR84 such as human GPR84 can be evaluated by comparing its effects on GPR84 to its effects on one or more other G protein-coupled receptors. In certain embodiments, a GPR84 selective compound is a GPR84 selective agonist having a selectivity for GPR84 over GPR88 (GenBank® Accession No. NP 071332) of at least about 100-fold. Following identification of compounds that modulate GPR84 functionality, such candidate compounds may be further tested in other assays including, but not limited to, in vivo models, in order to confirm or quantitate their activity. Modulators of GPR84 functionality are therapeutically useful, e.g., in treatment of diseases and physiological conditions in which normal or aberrant GPR84 functionality is involved.

Agents that are ligands of a GPCR of the invention such as a mammalian GPR84 may be identified by contacting a candidate compound with the GPCR (or with a recombinant host cell that comprises the mammalian GPR84 or with a host cell membrane that comprises the mammalian GPCR) and determining whether the candidate compound binds to the receptor. The selectivity of a compound that binds to a mammalian GPR84 such as human GPR84 can be evaluated by comparing its binding to GPR84 to its binding to one or more other G protein-coupled receptors. Ligands that are modulators of GPR84 receptor functionality are therapeutically useful in treatment of diseases and physiological conditions in which normal or aberrant GPR84 functionality is involved.

Antagonists and inverse agonists of the invention (e.g., an antagonist or inverse agonist of a mammalian GPR84) are envisioned to be useful as adjuvants for increasing the immunogenicity of vaccine compositions for the purpose of eliciting a specific immune response. The specific immune response may be an antibody response and/or a cytotoxic T cell response. The present invention expressly contemplates vaccine compositions comprising an antagonist and/or inverse agonist of the invention and the use thereof in a subject for elicitation of a specific immune response. An antagonist or inverse agonist of the invention can be shown to have adjuvant activity using methods well known in the art, including methods disclosed in U.S. Pat. Nos. 6,780,421 and 6,630,161.

The present invention also relates to radioisotope-labeled versions of compounds of the invention identified as modulators or ligands of a GPCR of the invention such as a mammalian GPR84 that would be useful not only in radio-imaging but also in assays, both in vitro and in vivo, for localizing and quantitating GPR84 in tissue samples, including human, and for identifying GPR84 ligands in methods relating to inhibition of binding of a radioisotope-labeled compound such as a known ligand of GPR84. It is a further object of this invention to develop novel assays relating to a GPCR of the invention such as a mammalian GPR84, such as human GPR84, which comprise such radioisotope-labeled compounds.

The present invention embraces radioisotope-labeled versions of compounds of the invention identified as modulators or ligands of a GPCR of the invention such as a mammalian GPR84, such as human GPR84.

The present invention also relates to radioisotope-labeled versions of test ligands that are useful for detecting a ligand bound to a GPCR of the invention such as a mammalian GPR84, such as human GPR84. In some embodiments, the present invention expressly contemplates a library of said radiolabeled test ligands useful for detecting a ligand bound to a GPCR of the invention such as a mammalian GPR84, such as human GPR84. In certain embodiments, said library comprises at least about 10, at least about $10^2$, at least about $10^3$, at least about $10^5$, or at least about $10^6$ said radiolabeled test compounds. It is a further object of this invention to develop novel assays relating to a GPCR of the invention such as a mammalian GPR84, such as human GPR84, which comprise such radioisotope-labeled test ligands.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro RUP40 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F $^{35}$S, $^{36}$Cl, $^{82}$Br, $^{75}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro RUP40 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Methods for adding one or more substituents comprising a radionuclide are within the purview of the skilled artisan and include, but are not limited to, addition of radioisotopic iodine by enzymatic method [Marchalonic J J, Biochemical Journal (1969) 113:299-305; Thorell J I and Johansson B G, Biochimica et Biophysica Acta (1969) 251:363-9; the disclosure of each of which is herein incorporated by reference in its entirety] and or by Chloramine-T/Iodogen/Iodobead methods [Hunter W M and Greenwood F C, Nature (1962) 194: 495-6; Greenwood F C et al., Biochemical Journal (1963) 89:114-23; the disclosure of each of which is herein incorporated by reference in its entirety].

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. Such modified approaches are considered within the purview of this disclosure. Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Recombinant DNA techniques relating to the subject matter of the present invention and well known to those of ordinary skill in the art can be found, e.g, in Maniatis T et al., *Molecular Cloning: A Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is herein incorporated by reference in its entirety.

Example 1

Full-Length Cloning of Endogenous Human GPR84

Polynucleotide encoding endogenous human GPR84 can be cloned by PCR using the GPR84 specific primers 5'-ACTAAGCTTCTATCATGTGGAACAGC-3' (SEQ ID NO:7; sense with HindIII site, ATG as initiation codon) and 5'-AGGAGACAGTCCTGAATT-3' (SEQ ID NO:8; antisense with the last 5 nucleotides being part of the endogenous EcoRI site in the 3' untranslated region) and human genomic DNA as template. Cloned pfu DNA polymerase (Stratagene) can be used for amplification by the following cycle with step 2 to step 4 repeated 25 times: 94° C., 3 minutes; 94° C., 1 minute; 52° C., 1 minute; 72° C., 2 minute; 72° C., 10 minutes.

A 1.24 Kb PCR fragment of predicted size can be isolated, digested with HindIII and EcoRI, and cloned into the pCMV expression vector and sequenced using the T7 DNA sequenase kit (Amersham). See, e.g., SEQ ID NO:1 for nucleic acid sequence encoding human GPR84 and SEQ ID NO:2 for the encoded human GPR84 amino acid sequence.

It is expressly contemplated that human cDNA derived from a tissue or cell type that expresses GPR84 can alternatively be used as template.

Example 2

Receptor Expression

Although a variety of cells are available to the art for the expression of proteins, it is most preferred that mammalian cells or melanophores be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells or melanophores. Of the mammalian cells, CHO, COS-7, MCB3901, 293 and 293T cells are particularly preferred, although the specific mammalian cell utilized can be predicated upon the particular needs of the artisan. See infra as relates to melanophores, including Example 9.

a. Transient Transfection

On day one, $4 \times 10^6$ 293 cells per 10 cm dish are plated out. On day two, two reaction tubes are prepared (the proportions to follow for each tube are per plate): tube A is prepared by mixing 4 μg DNA (e.g., pCMV vector; pCMV vector comprising polynucleotide encoding a GPCR of the invention, etc.) in 0.5 ml serum free DMEM (Gibco BRL); tube B is prepared by mixing 24 μl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 μg of DNA (e.g., pCMV-neo$^4$ vector comprising polynucleotide encoding a GPCR of the invention). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/ml. The transfected cells now undergo selection for positively transfected cells containing the G418 resistance gene. The medium is replaced every four to five days as selection occurs. During selection, cells are grown to create stable pools, or split for stable clonal selection.

Example 3

Assays for Determination of GPCR Activation (e.g., Screening Assays)

A variety of approaches are available for assessing activation of a GPCR of interest, or "target" GPCR. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used to screen candidate compounds as modulators of GPCRs. The assay is generic and has application to drug discovery at all G protein-coupled receptors.

The [$^{35}$S]GTPγS assay is incubated in 20 mM HEPES and between 1 and about 20 mM MgCl$_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 µg membrane protein (e.g, 293 cells expressing a GPCR of the invention; this amount can be adjusted for optimization) and 10 µM GDP (this amount can be changed for optimization) for 1 hour. Wheatgerm agglutinin beads (25 µl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty-four to forty-eight hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) is prepared and maintained in accordance with the manufacturer's instructions. Assay Buffer is prepared fresh for screening and contains 50 µl of Stimulation Buffer, 3 µl of test compound (12 µM final assay concentration) and 50 µl cells. Assay Buffer is stored on ice until utilized. The assay, preferably carried out e.g. in a 96-well plate, is initiated by addition of 50 µl of cAMP standards to appropriate wells followed by addition of 50 µl of PBSA to wells H-11 and H12. 50 µl of Stimulation Buffer is added to all wells. DMSO (or selected candidate compounds) is added to appropriate wells using a pin tool capable of dispensing 3 µl of compound solution, with a final assay concentration of 12 µM test compound and 100 µl total assay volume. The cells are then added to the wells and incubated for 60 min at room temperature. 100 µl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP Assay for Gi-Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi coupled Target GPCR to establish a baseline level of cAMP. The Gi coupled receptor is co-transfected with the signal enhancer, and it is this material that can be used for screening. Such an approach can be utilized to effectively generate a signal when a cAMP assay is used. In some embodiments, this approach is preferably used in the identification of candidate compounds against Gi coupled receptors. It is noted that for a Gi coupled GPCR, when this approach is used, an inverse agonist of the Target GPCR will increase the cAMP signal and an agonist will decrease the cAMP signal.

On day one, 4×10⁶ 293 cells per 10 cm dish will be plated out. On day two, two reaction tubes will be prepared (the proportions to follow for each tube are per plate): tube A will be prepared by mixing 2 μg DNA of each receptor transfected into the mammalian cells, for a total of 4 μg DNA (e.g., pCMV vector; pCMV vector with mutated THSR (TSHR-A623I); TSHR-A623I and the Target GPCR, etc.) in 0.5 ml serum free DMEM (Irvine Scientific, Irvine, Calif.); tube B will be prepared by mixing 24 μl lipofectamine (Gibco BRL) in 0.5 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 5 ml serum free DMEM. 1.0 ml of the transfection mixture will then be added to the cells, followed by incubation for 4 hrs at 37° C./5% $CO_2$. The transfection mixture will then be removed by aspiration, followed by the addition of 10 ml of DMEM/10% Fetal Bovine Serum. Cells will then be incubated at 37° C./5% $CO_2$. After approximately 24-48 hr incubation, cells will then be harvested and utilized for analysis.

A Flash Plate™ Adenylyl Cyclase kit (New England Nuclear; Cat. No. SMP004A) is designed for cell-based assays, but can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty-four to forty-eight hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 μl/well).

cAMP standards and Detection Buffer (comprising 1 μCi of tracer [$^{125}$I] cAMP (50 μl) to 11 ml Detection Buffer) will be prepared and maintained in accordance with the manufacturer's instructions. Assay Buffer should be prepared fresh for screening and contained 50 μl of Stimulation Buffer, 3 μl of test compound (12 μM final assay concentration) and 50 μl cells, Assay Buffer can be stored on ice until utilized. The assay can be initiated by addition of 50 μl of cAMP standards to appropriate wells followed by addition of 50 μl of PBSA to wells H-11 and H12. Fifty μl of Stimulation Buffer will be added to all wells. Selected compounds (e.g., TSH) will be added to appropriate wells using a pin tool capable of dispensing 3 μl of compound solution, with a final assay concentration of 12 μM test compound and 100 μl total assay volume. The cells will then be added to the wells and incubated for 60 mm at room temperature. 100 μl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-LUC Reporter Assay (Gs-Associated Receptors)

293 and 293T cells are plated-out on 96 well plates at a density of 2×10⁴ cells per well and were transfected using Lipofectamine Reagent (BRL) the following day according to manufacturer instructions. A DNA/lipid mixture is prepared for each 6-well transfection as follows: 260 ng of plasmid DNA in 100 μl of DMEM is gently mixed with 2 μl of lipid in 100 μl of DMEM (the 260 ng of plasmid DNA consists of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BgIV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BgIV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 μl of DMEM and 100 μl of the diluted mixture is added to each well. 100 μl of DMEM with 10% FCS are added to each well after a 4 hr incubation in a cell culture incubator. The following day the transfected cells are changed with 200 μl/well of DMEM with 10% FCS. Eight (8) hours later, the wells are changed to 100 μl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue # 219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP (secreted alkaline phosphatase expression plasmid; alkaline phosphatase activity is measured in the media of transfected cells to control for variations in transfection efficiency between samples):

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetec™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with, e.g. 1 μM, test compound. Cells are then lysed and assayed for luciferase activity using a Luclite™ Kit (Packard, Cat. # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular IP3 Accumulation Assay (Gq-Associated Receptors)

On day 1, cells comprising the receptors (endogenous or non-endogenous) can be plated onto 24 well plates, usually $1\times10^5$ cells/well (although his number can be optimized. On day 2 cells can be transfected by first mixing 0.25 μg DNA in 50 μl serum free DMEM/well and 2 μl lipofectamine in 50 μl serum free DMEM/well. The solutions are gently mixed and incubated for 15-30 min at room temperature. Cells are washed with 0.5 ml PBS and 400 μl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3H$-myo-inositol. Briefly, the media is removed and the cells are washed with 0.5 ml PBS. Then 0.5 ml inositol-free/serum free media (GIBCO BRL) is added/well with 0.25 μCi of $^3H$-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 μM pargyline 10 mM lithium chloride or 0.4 ml of assay medium and optionally 50 μl of test compound to final concentration of 10 μM. The cells are then incubated for 30 min at 37° C. The cells are then washed with 0.5 ml PBS and 200 μl of fresh/ice cold stop solution (1M KOH; 18 mM Na-borate; 3.8 mM EDTA) is added/well. The solution is kept on ice for 5-10 min or until cells were lysed and then neutralized by 200 μl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 WN and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 4

Fusion Protein Preparation a. GPCR:Gs Fusion Construct

The design of the GPCR-G protein fusion construct can be accomplished as follows: both the 5' and 3' ends of the rat G protein Gsα (long form; Itoh, H. et al., 83 *PNAS* 3776 (1986)) are engineered to include a HindIII (5'-AAGCTT-3') sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the Gsα sequence is determined after subcloning into pcDNA3.1(−). The modified pcDNA3.1(−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 amino acid deletion)/Gi Fusion Construct

A Gq(del)/Gi fusion construct is a chimeric G protein whereby the first six (6) amino acids of the Gq-protein α-subunit ("Gαq") are deleted and the last five (5) amino acids at the C-terminal end of Gαq are replaced with the corresponding amino acids of the Gαi subunit. A Gq(del)/Gi fusion construct will force an endogenous Gi coupled receptor to couple to its non-endogenous G protein, Gq (in the form of Gq(del)/Gi), such that the second messenger, for example, inositol triphosphate or diacylglycerol or $Ca^{2+}$, can be measured in lieu of cAMP production.

The Gq(del)/Gi fusion construct was designed as follows: the N-terminal six (6) amino acids (amino acids 2 through 7, having the sequence of TLESIM (SEQ ID NO: 9) of the Gαg-subunit were deleted and the C-terminal five (5) amino acids, having the sequence EYNLV (SEQ ID NO: 10) were replaced with the corresponding amino acids of the Gαi Protein, having the sequence DCGLF (SEQ ID NO: 11). This fusion construct was obtained by PCR using the following primers:
5'-gatcaagcttcCATGGCGTGCTGCCTGAGCGAGGAG-3' (SEQ ID NO: 12) and 5'-gatcggatccTTAGAACAGGCCG-CAGTCCTTCAGGTTCAGCTGCAGGATGGTG-3' (SEQ ID NO: 13) and Plasmid 63313 (ATCC®, Number 63313) which contains the mouse Gαq-wild-type version with a hemagglutinin tag as a template. Nucleotides in lower case include cloning sites for HindIII/BamHI and spacers.

TaqPlus Precision DNA polymerase (Stratagene) was utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product was cloned into a pCRII-TOPO vector (Invitrogen) and sequenced using the ABI Big Dye Terminator kit (P. E. Biosystems). Inserts from a TOPO clone containing the sequence of the fusion construct was shuttled into the expression vector pcDNA3.1(+) at the HindIII/BamHI site by a 2 step cloning process. See, SEQ ID NO:14 for the nucleic acid sequence and SEQ ID NO:15 for the encoded amino acid sequence of Gq(del)/Gi construct.

Example 5

[$^{35}S$]GTPγS Assay

A. Membrane Preparation

In some embodiments membranes comprising a Target GPCR and for use in the identification of candidate compounds as, e.g., inverse agonists, agonists, or antagonists, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1, 000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 µl Binding Buffer. Thereafter, 10 µl of Bradford Protein Standard (1 mg/ml) will be added to each tube, and 10 µl of membrane Protein will then be added to just one tube (not the blank). Thereafter, 200 µl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595 nm.

Identification Assay a. Materials

GDP Buffer consists of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 µg/well). Thereafter, 100 µl GDP Buffer is added to each well of a Wallac Scintistrip™ (Wallac). A 5 µl pin-tool will then be used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

Example 6

Cyclic AMP Assay

Another assay approach for identifying candidate compounds as, e.g., inverse agonists, agonists, or antagonists, is accomplished by utilizing a cyclase-based assay. In addition to so identifying candidate compounds, this assay approach can be utilized as an independent approach to provide confirmation of the results from the [$^{35}$S]GTPγS approach as set forth in Example 5, supra.

A modified Flash Plate™ Adenylyl Cyclase kit (New England Nuclear; Cat. No. SMP004A) is preferably utilized for identification of candidate compounds as modulators of a Target GPCR in accordance with the following protocol.

Cells transfected with the Target GPCR are harvested approximately three days after transfection. Membranes are prepared by homogenization of suspended cells in buffer containing 20 mM HEPES, pH 7.4 and 10 mM $MgCl_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM $MgCl_2$, to yield a final protein concentration of 0.60 mg/ml (the resuspended membranes are placed on ice until use).

cAMP standards and Detection Buffer (comprising 2 µCi of tracer [$^{125}$I]cAMP (100 µl) to 11 ml Detection Buffer) are prepared and maintained in accordance with the manufacturer's instructions. Assay Buffer is prepared fresh for screening and contains 20 mM HEPES, pH 7.4, 10 mM $MgCl_2$, 20 mM phosphocreatine (Sigma), 0.1 units/ml creatine phosphokinase (Sigma), 50 µM GTP (Sigma), and 0.2 mM ATP (Sigma); Assay Buffer is then stored on ice until utilized.

Candidate compounds are added, preferably, to e.g. 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

By way of example and not limitation, an illustrative screening assay plate (96 well format) result obtained is presented in FIG. 1. Each bar represents the result for a compound that differs in each well, the "Target GPCR" being a Gsα Fusion Protein construct of an endogenous, constitutively active Gs-coupled GPCR unrelated to GPR84. The results presented in FIG. 1 also provide standard deviations based upon the mean results of each plate ("m") and the mean plus two arbitrary preference for selection of inverse agonists as "leads" from the primary screen involves selection of candidate compounds that that reduce the percent response by at least the mean plate response, minus two standard deviations. Conversely, an arbitrary preference for selection of agonists as "leads" from the primary screen involves selection of candidate compounds that increase the percent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, it is possible to ascertain compounds that are able to reduce the functional activity of this receptor (Compound A) as well as increase the functional activity of the receptor (Compound B).

Example 7

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 μl DMSO and 467 μl Pluronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 μl of 4 μM Fluo4-AM/ 2.5 mM Probenicid (Sigma, #P8761)/20 mM HEPES/complete medium at pH 7.4. Incubation at 37° C./5% $CO_2$ is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% $CO_2$ for 60 min.

FLIPR (Fluorometric Imaging Plate Reader; Molecular Device) is programmed to add 50 μl candidate compound on the 30th second and to record transient changes in intracellular calcium concentration ($[Ca^{2+}]$) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise Gα15, Gα16, or Gq(del)/Gi chimeric G protein.

Although the foregoing provides a FLIPR assay for agonist activity using stably transfected cells, a person of ordinary skill in the art would readily be able to modify the assay in order to characterize antagonist activity. The person of ordinary skill in the art would also readily appreciate that, alternatively, transiently transfected cells could be used.

Example 8

MAP Kinase Assay

MAP kinase (mitogen activated kinase) may be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then be aspirated through the filter, which retains, the phosphorylated myelin basic protein. The filter is washed and counted for $^{32}$P by liquid scintillation counting.

Example 9

Melanophore Technology

Melanophores skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition: Dispersion of pigments cells due to the candidate compound, including but not limited to a ligand, coupling to the GPCR will appear dark on a petri dish, while aggregation of pigments cells will appear light.

Materials and methods can be followed according to the disclosure of U.S. Pat. Nos. 5,462,856 and 6,051,386. These patent disclosures are herein incorporated by reference in their entirety.

The cells are plated in e.g. 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7×L-15 (Gibco). After one hour, the cells in serum-free media remain in a pigment-dispersed state while the melatonin-treated cells are in a pigment-aggregated state. At this point, the cells are treated with a dose response of a test/candidate compound. If the plated GPCRs bind to the test/candidate compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Example 10

Monocyte/Macrophage Expression of GPR84

A. Microarray Analysis of GPR84 Expression

Figure 2A:
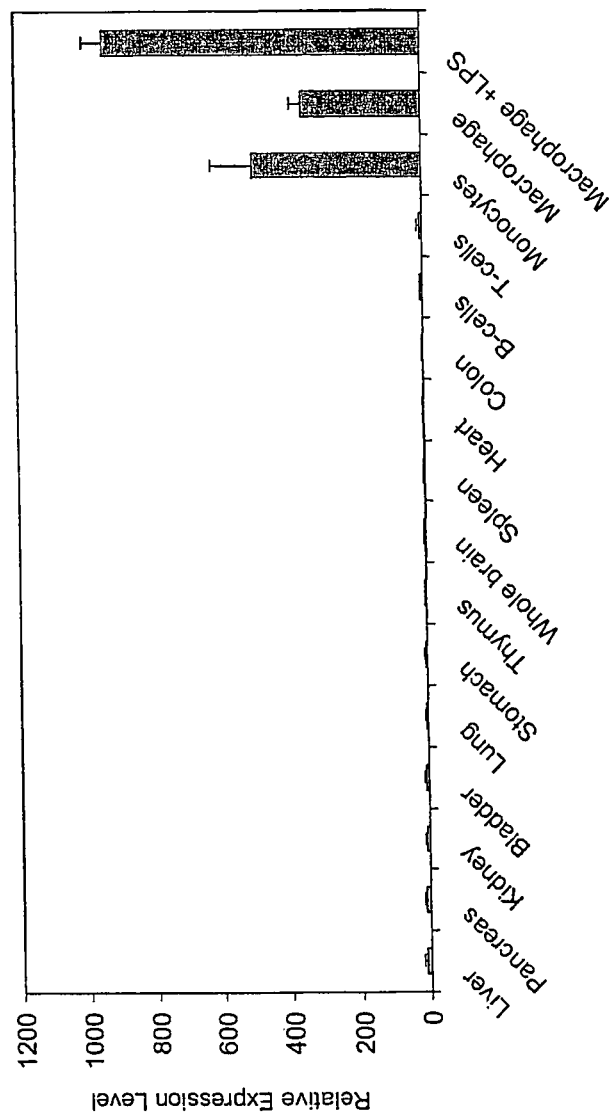
FIG. 2. A. Microarray analysis of GPR84 expression. B. Expression of GPR84 in human macrophage. C. Expression of GPR84 in mouse macrophage. (See, Example 10.)

GPR84 expression across a panel of normal human tissues and isolated cells was assessed by microarray analysis of total RNA and is shown in FIG. 2A. The microarray analysis used 26 probes for GPR84 to assess expression. The expression levels in FIG. 2A are the average and SD of two replicates. GPR84 expression was found to be enriched in human monocyte and macrophage cell types.

B. Expression of GPR84 in Human Macrophage

Figure 2B:
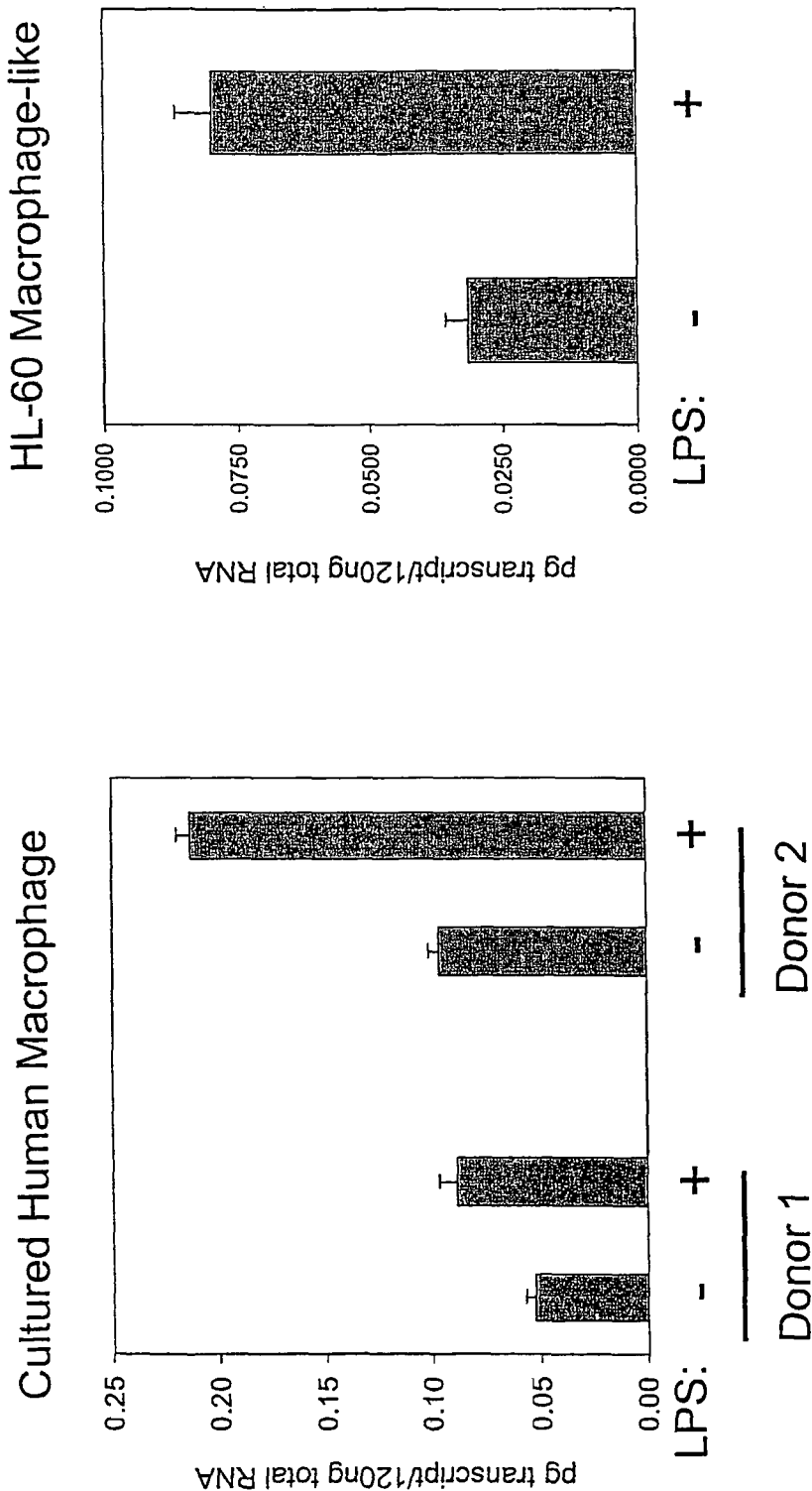

Taqman analysis of GPR84 in human macrophage was carried as shown in FIG. 2B. TaqMan analysis was performed on cultured monocyte-derived macrophages from two donors as well as the stable cell line HL-60 differentiated into macrophage-like cells by TPA treatment for 24 hrs. Cells were either vehicle treated or stimulated with 1 ng/ml of LPS. For quantitative PCR (qPCR) analysis, the cDNA was synthesized from total RNA using the Bio-Rad cDNA synthesis kit following the manufacturer's protocol. The Bio-Rad PCR machine was used for this synthesis.

The qPCR reactions were prepared from the cDNA using the Bio-Rad qPCR kit, following the manufacturer's protocol. The qPCR reactions were performed using the ABI Prism 7900HT machine with the following temperatures and times: 50° C., 2 minutes; 95° C., 10 minutes; followed by 40 cycles of 95° C., 15 seconds and 60° C., 1 minute.

Primers and probe sequences used for qPCR analysis human GPR84 were as follows:

```
                                           (SEQ ID NO: 16)
    Forward Primer-5'-TCCTTTTTGCCTCCAATTCTGT-3'

(SEQ ID NO: 17)
    Reverse Primer-5'-GCGTCCCAGTGCGATGAG-3'

(SEQ ID NO: 18)
    Taqman MGB Probe-6FAM-5'-TCCATCCTGACCCTCT-3'
```

GPR84 was found to be expressed in human macrophage, and the level of GPR84 expression in human macrophage was found to be up-regulated by LPS (FIG. 2B).

C. Expression of GPR84 in Mouse Macrophage

Microarray analysis of mouse GPR84 expression in the macrophage cell lines RAW and Jaws2 was carried out. Cell lines were cultured to subconfluency and then stimulated with 10 ng/ml of LPS for the indicated times. Total RNA was extracted from treated cells and analyzed by microarray analysis. Expression levels are the average and SD of two replicates.

Figure 2C:
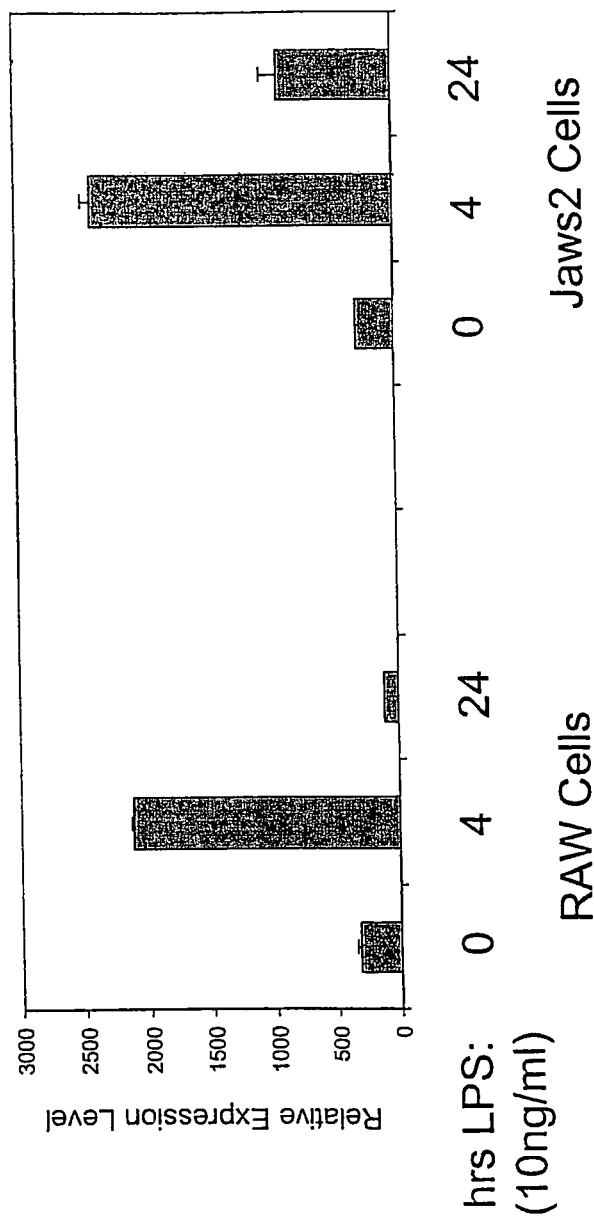

GPR84 was found to be expressed in mouse macrophage lines, and the level of GPR84 expression in mouse macrophage was found to be up-regulated by LPS (FIG. 2C).

Example 11

Upregulation of GPR84 mRNA in Human Monocytes by Proinflammatory Cytokines

Regulation of GPR84 mRNA expression in human monocytes by the proinflammatory cytokines tumor necrosis factor alpha (TNFα) and interferon gamma (IFNγ) was assessed by QRT-PCR as described below.

Peripheral blood leukocytes were separated from erythrocytes by sedimentation in a dextran containing saline solution. The leukocytes were washed, and mononuclear cells were isolated on a Ficoll density gradient. Peripheral blood mononuclear cells were then washed and negatively selected using a MACS® monocyte isolation kit II (Miltenyi Biotec, Auburn, Calif.) and LS MACS® cell separation columns according to manufacturer's instructions. Freshly isolated monocytes were then resuspended in culture medium alone or culture medium supplemented with TNFα (10 ng/ml) or IFNγ (10 or 100 ng/ml) and allowed to adhere to wells precoated with vitronectin. Cultures were harvested at the indicated times. GPR84 TaqMan analysis was performed essentially as described in Part A of Example 15, infra. Multiple replicates were obtained from different individual donors. Data are expressed as the mean of the ratio of the GPR84 signal to the HS9 (Human ribosomal protein S9, housekeeping gene) signal±SEM.

From FIG. 3A, it is apparent that overnight incubation of primary human monocytes with TNFα under the conditions of the assay led to a significant increase in GPR84 mRNA expression (p=0.0252 by Student's t test, with a value of p<0.05 considered significant). From FIG. 3B, it is apparent that overnight incubation of primary monocytes with IFNγ under the conditions of the assay led to a dose-dependent increase in GPR84 mRNA expression.

Example 12

Analysis of GPR84 mRNA Expression in Rheumatoid Arthritis Synovium by In Situ Hybridization The expression of GPR84 mRNA in rheumatoid arthritis synovial tissue was examined by in situ hybridization. Sections of human tissue obtained from biopsy were embedded in paraffin and subjected to in situ hybridization as described here.

Tissue sections were deparaffinized and rehydrated, followed by acetylation to quench nonspecific binding of probe to tissue. Single-stranded sense and anti-sense $^{33}$P-labeled RNA probes were generated by in vitro transcription from the cDNA encoding human GPR84 (the 820 bp cDNA fragment corresponding to nucleotides 372 to 1191 of SEQ ID NO:1). Hybridization with the probes was performed at 55° C. for 16 h, after which the sections were washed in 0.1×SSC buffer, followed by digestion with ribonuclease A. Slides were then washed in 2×SSC, 1×SSC and 0.5×SSC (5 min) prior to incubation in 0.1×SSC at 65° C. for 1 hour. Following incubation, slides were washed in 0.1×SSC (room temp) and dehydrated. Slides were exposed to film for 3-5 days and images were captured with MTI CCD camera (Compix Inc.). Tissues were stained with hematoxalin and eosin for histology, including for the characterization of leukocyte infiltration. CD68$^+$ macrophages were identified by immunohistochemistry.

GPR84 mRNA expression in rheumatoid arthritis synovial tissue was found to be associated with areas of leukocyte infiltration. A representative analysis is shown in FIG. 4. The sense probe (Panel A) did not show hybridization, evidencing the specificity of the GPR84 signal obtained using the anti-sense probe (Panel B). Analysis of the boxed area in Panel B at increased magnification showed that the area of high GPR84 mRNA expression corresponded to an area of high infiltration by CD68$^+$ macrophages (Panels C and D).

Example 13

Identification of Candidate Compounds as Agonists of GPR84

A. Identification of Compound 1 as an Agonist of GPR84

Figure 5A:
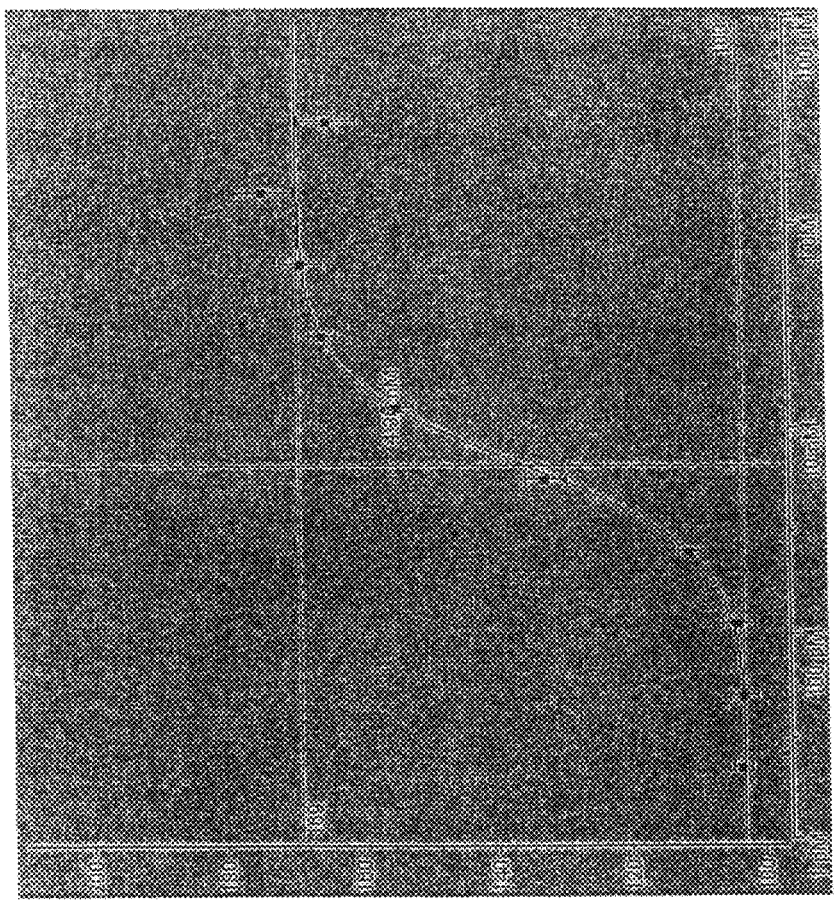
FIG. 5. A. Identification of Compound 1 as an agonist of GPR84. B. Identification of Compound 2 as an agonist of GPR84. C. Identification of Compound 3 as an agonist of GPR84. (See, Example 13.)

Melanophores were transiently transfected with plasmid DNA encoding human GPR84 and used in aggregation assay. Cells were cultured for 48 hours, plated into assay plates and initial absorbance readings collected (Ai). Serial diluted compound was added to assay plates. After a one hour incubation, a final absorbance reading was collected (Af). Absorbance was calculated (Af–Ai)–1 and plotted as percent of positive control versus molar compound concentration. These results demonstrate that Compound 1 is a potent agonist at GPR84 in vitro. These results also are consistent with GPR84 being a Gi-coupled receptor. In the representative melanophore assay shown in FIG. 5A, Compound 1 was found to have an EC$_{50}$ at GPR84 of 4.36 nM. As Compound 1 has an EC$_{50}$ at GPR88 of greater than 100 μM (not shown), Compound 1 is a selective GPR84 agonist.

B. Identification of Compound 2 as an Agonist of GPR84

Figure 5B:
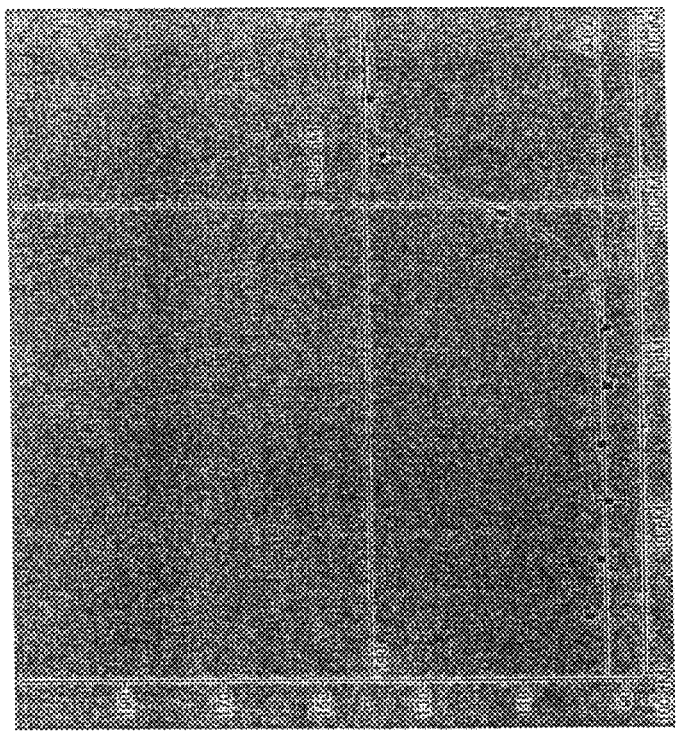

Melanophores were transiently transfected with plasmid DNA encoding human GPR84 and used in aggregation assay. Cells were cultured for 48 hours, plated into assay plates and initial absorbance readings collected (Ai). Serial diluted compound was added to assay plates. After a one hour incubation, a final absorbance reading was collected (Af). Absorbance was calculated (Af–Ai)–1 and plotted as percent of positive control versus molar compound concentration. These results demonstrate that Compound 2 is a potent agonist at GPR84 in vitro. These results also are consistent with GPR84 being a Gi-coupled receptor. In the representative melanophore assay shown in FIG. 5B, Compound 2 was found to have an EC$_{50}$ at GPR84 of 48.2 nM. As Compound 2 has an EC$_{50}$ at GPR88 of greater than 10 μM (not shown), Compound 2 is a selective GPR84 agonist.

C. Identification of Compound 3 as an Agonist of GPR84

Melanophores were transiently transfected with plasmid DNA encoding human GPR84 and used in aggregation assay. Cells were cultured for 48 hours, plated into assay plates and initial absorbance readings collected (Ai). Serial diluted compound was added to assay plates. After a one hour incubation, a final absorbance reading was collected (Af). Absorbance was calculated (Af–Ai)–1 and plotted as percent of positive control versus molar compound concentration. These results demonstrate that Compound 3 is a potent agonist at GPR84 in vitro. These results also are consistent with GPR84 being a Gi-coupled receptor. In the representative melanophore assay shown in FIG. 5C, Compound 3 was found to have an EC$_{50}$ at GPR84 of 30.8 nM. As Compound 3 has an EC$_{50}$ at GPR88 of greater than 10 μM, Compound 3 is a selective GPR84 agonist.

Example 14

Evidence for GPR84 as a Gi-coupled GPCR

A. Agonist to GPR84 Stimulates GTPγS Binding to Membrane

GTPγS assay of GPR84 activity was carried out. Membranes prepared from GPR84 transfected CHO-KI cells were dissolved in binding buffer (20 mM HEPES, pH 7.4, 100 mM NaCl, 10 mM MgCl$_2$) and homogenized briefly using a polytron. Membrane protein concentration was determined by Bradford assay and the membranes were diluted to 0.4 mg/ml in binding buffer. 50 ul of the membranes were pre-incubated with Compound 1 in the absence or presence of pertussis toxin (PTX) diluted in assay buffer containing 40 mM GDP (final [GDP] was 10 mM) in Wallac Scintistrip plates for 10 minutes before the addition of 25 μl of 0.3 nM $^{35}$S-GTPγS. Binding was allowed to proceed for one hour before centrifuging the plates at room temperature to pellet the membrane and subsequent counting in a TopCount scintillation counter.

Figure 6A:
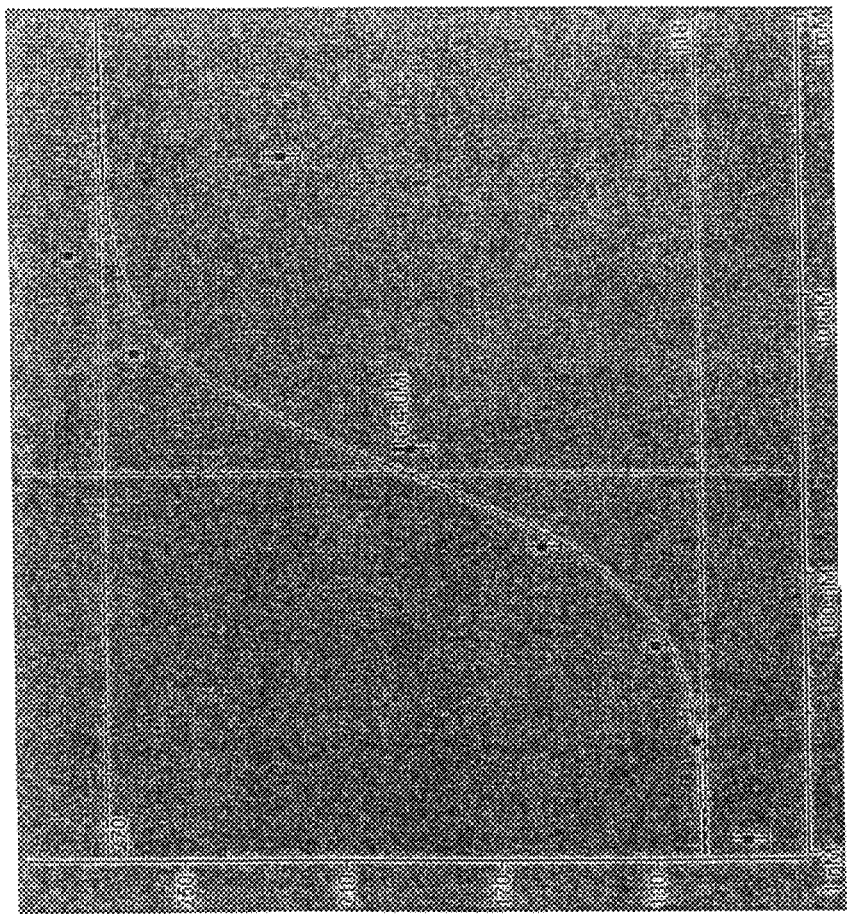
FIG. 6. A. Agonist to GPR84 stimulates GTPγS binding to membrane. B. Agonist to GPR84 decreases intracellular cAMP. C. Agonist to GPR84 increases IP$_3$ accumulation in the presence of Gq(del)/Gi chimeric G protein. (See, Example 14.)

In the representative GTPγS assay shown in FIG. 6A, Compound 1 was found to have an EC$_{50}$ at GPR84 of 540 nM. Pertussis toxin was found to inhibit the stimulation of GTPγS binding to membrane by Compound 1, consistent with GPR84 being a Gi-coupled receptor (not shown).

B. Agonist to GPR84 Decreases Intracellular cAMP

Thyroid-stimulating hormone (TSH, or thyrotropin) receptor (TSHR) causes the accumulation of intracellular cAMP on activation by its ligand TSH. An effective technique for measuring the decrease in production of cAMP corresponding to activation of a Gi-coupled receptor is to co-transfect TSHR with the Gi-coupled receptor and to carry out the assay in the presence of TSH to raise the level of basal cAMP, whereby TSHR acts as a "signal window enhancer." Such an approach was used here.

Cyclase assay of GPR84 activity was carried out. 293 cells were transfected with either vector alone or vector containing polynucleotide encoding GPR84. 48 hrs after transfection, 50,000 cells were treated for 1 hr with or without Compound 1 as GPR84 agonist and analyzed using the cAMP Flashplate kit from Perkin Elmer.

Figure 6B:
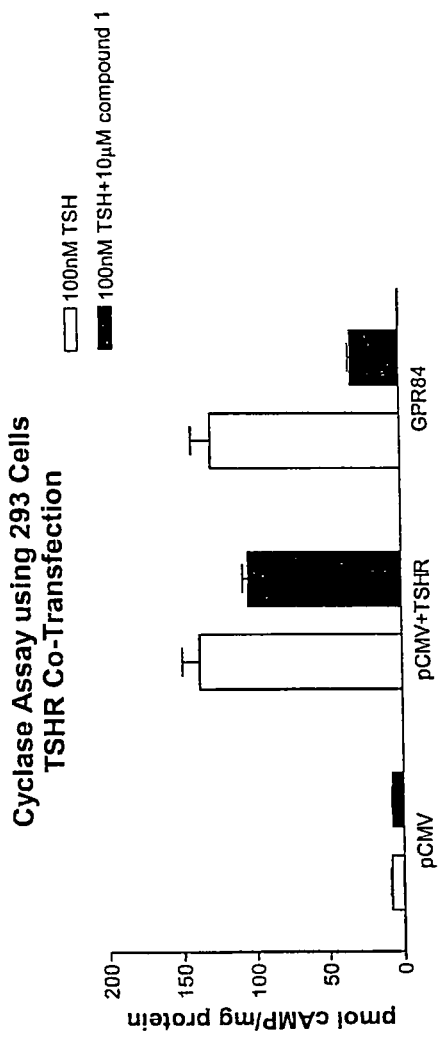

Compound 1 was found to decrease the level of intracellular cAMP (FIG. 6B). The results are consistent with GPR84 being a Gi-coupled receptor.

C. Agonist to GPR84 Increases IP$_3$ Accumulation in the Presence of Gq(Del)/Gi Chimeric G Protein IP$_3$ Assay of GPR84 activity was carried out. 293 cells were transfected with either vector alone or vector containing polynucleotide encoding GPR84. The 293 cells comprised or did not comprise Gq(del)/Gi chimeric G protein. 24 hrs after transfection, cells were plated into 96 well plates, labeled overnight with $^3$H-myoinositol. The following day, cells were stimulated for 3 hrs with 10 µM Compound 1 as GPR84 agonist or vehicle and IP accumulation was measured.

Figure 6C:
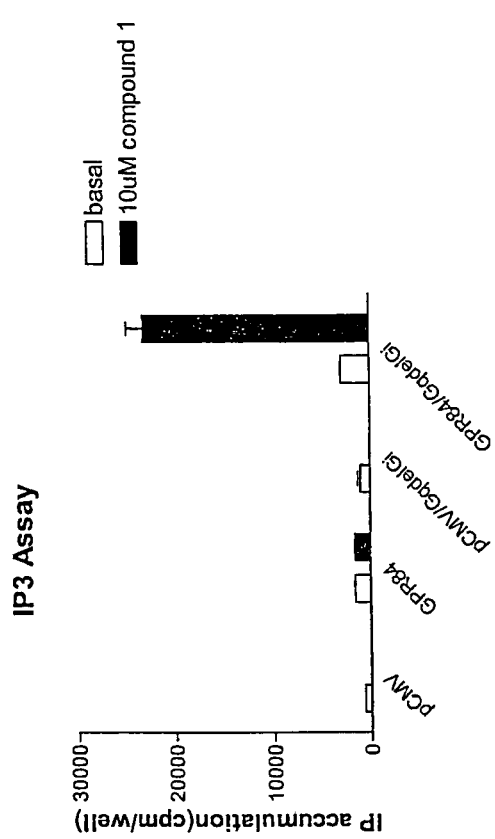

Compound 1 was found to increase the level of intracellular IP accumulation in 293 cells comprising Gq(del)/Gi chimeric G protein, but not in 293 cells which did not comprise Gq(del)/Gi (FIG. 6C). The results are consistent with GPR84 being a Gi-coupled receptor.

Example 15

Agonist to GPR84 Selectively Modulates Gene Expression in Monocytes/Macrophages

A. Agonist to GPR84 Increases Steady-State ABCA1 mRNA Level in Human Macrophage

The effect of Compound 1 treatment on steady-state ABCA1 mRNA level in human macrophage was assessed. Macrophages were derived from monocytes as previously indicated. Cells were treated for 24 hours with vehicle or Compound 1. Vehicle was dimethyl sulfoxide (DMSO); the final concentration of DMSO in the culture was 0.1% (v/v). Total RNA was extracted from the cells and analyzed by TaqMan analysis as previously indicated to assess steady-state ABCA1 mRNA level. Data are the average and SD of three replicates.

The qPCR reactions were prepared from the cDNA using the Bio-Rad qPCR kit, following the manufacturer's protocol. The qPCR reactions were performed using the ABI Prism 7900HT machine with the following temperatures and times: 50° C.—2 min, 95° C.—10 min followed by 40 cycles of 95° C.—15 sec and 60° C.—1 min.

Primers and probe sequences used for qPCR analysis human ABCA1 are as follows:

```
                                        (SEQ ID NO: 21)
Forward primer 5'-TCCAGGCCAGTACGGAATTC-3'

(SEQ ID NO: 22)
Reverse primer 5'-ACTTTCCTCGCCAAACCAGTAG-3'

(SEQ ID NO: 23)
Taqman MGB Probe 5'-CTGGTATTTTCCTTGCACCAA-3'
```

Figure 7A:
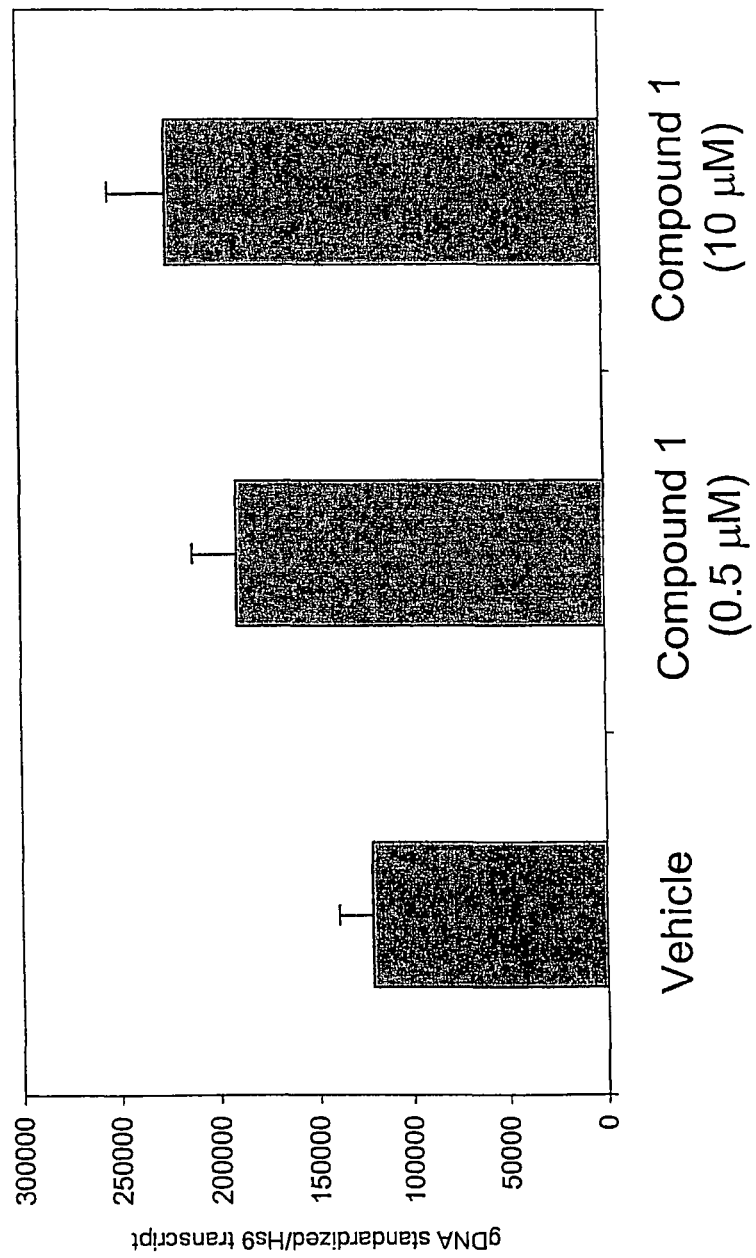
FIG. 7. A. Agonist to GPR84 increases steady-state ABCA1 mRNA level in human macrophage. B. Agonist to GPR84 selectively modulates steady-state chemokine mRNA level in human macrophage. C. Agonist to GPR84 does not increase TNFα secretion in human macrophage. D. Agonist to GPR84 does not increase TNFα secretion in mouse macrophage. (See, Example 15.)

Compound 1 was found to increase the steady-state level of ABCA1 mRNA in human macrophage (FIG. 7A).

B. Agonist to GPR84 Selectively Modulates Steady-State Chemokine mRNA Level in Human Macrophage The effect of Compound 1 treatment on steady state MCP-1 and IL-8 mRNA level in human macrophage was assessed by microarray analysis. Human peripheral blood monocytes were isolated from buffy coat by dextran and ficoll purification. Monocytes were then purified using a monocyte isolation kit from Miltenyi Biotec. Monocytes were cultured for 7 days with 10 ng/ml GM-CSF to derive macrophage cells. Cells were treated with vehicle or 10 µM Compound 1 for 24 hours. MCP-1 and IL-8 steady-state mRNA levels were assessed by microarray analysis. Vehicle was dimethyl sulfoxide (DMSO); the final concentration of DMSO in the culture was 0.1% (v/v). Expression levels are the average and SD of two replicates.

Figure 7B:
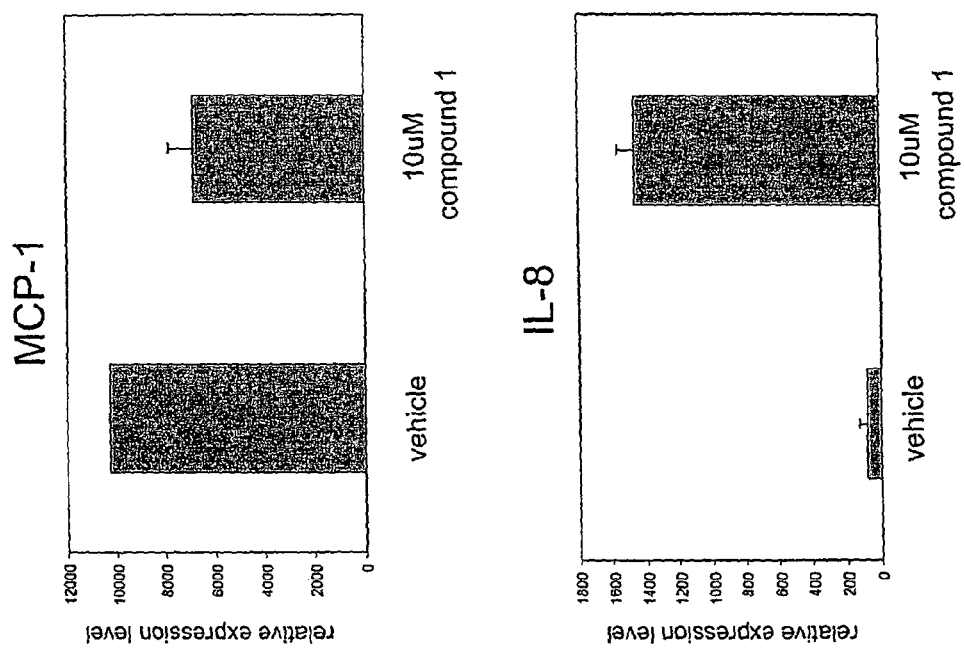

Compound 1 was found to decrease the steady-state level of MCP-1 mRNA and to increase the steady-state level of IL-8 mRNA in human macrophage (FIG. 7B).

C. Agonist to GPR84 does not Increase TNFα Secretion in Human Macrophage

The effect of Compound 1 treatment TNFα secretion by human macrophage in the absence or presence of LPS was assessed. Human peripheral blood monocytes were isolated from buffy coat by dextran and ficoll purification. Monocytes were then purified using a monocyte isolation kit from Miltenyi Biotec. Monocytes were cultured for 7 days with 10 ng/ml GM-CSF to derive macrophage cells. Cells were treated with vehicle or 10 µM Compound 1 for 24 hrs. Vehicle was dimethyl sulfoxide (DMSO); the final concentration of DMSO in the culture was 0.1% (v/v). Cells were then stimulated with the indicated concentrations of LPS for 24 hours. Supernatants were collected and TNFα levels were assayed using a human specific TNFα ELISA kit from Biosource.

Figure 7C:
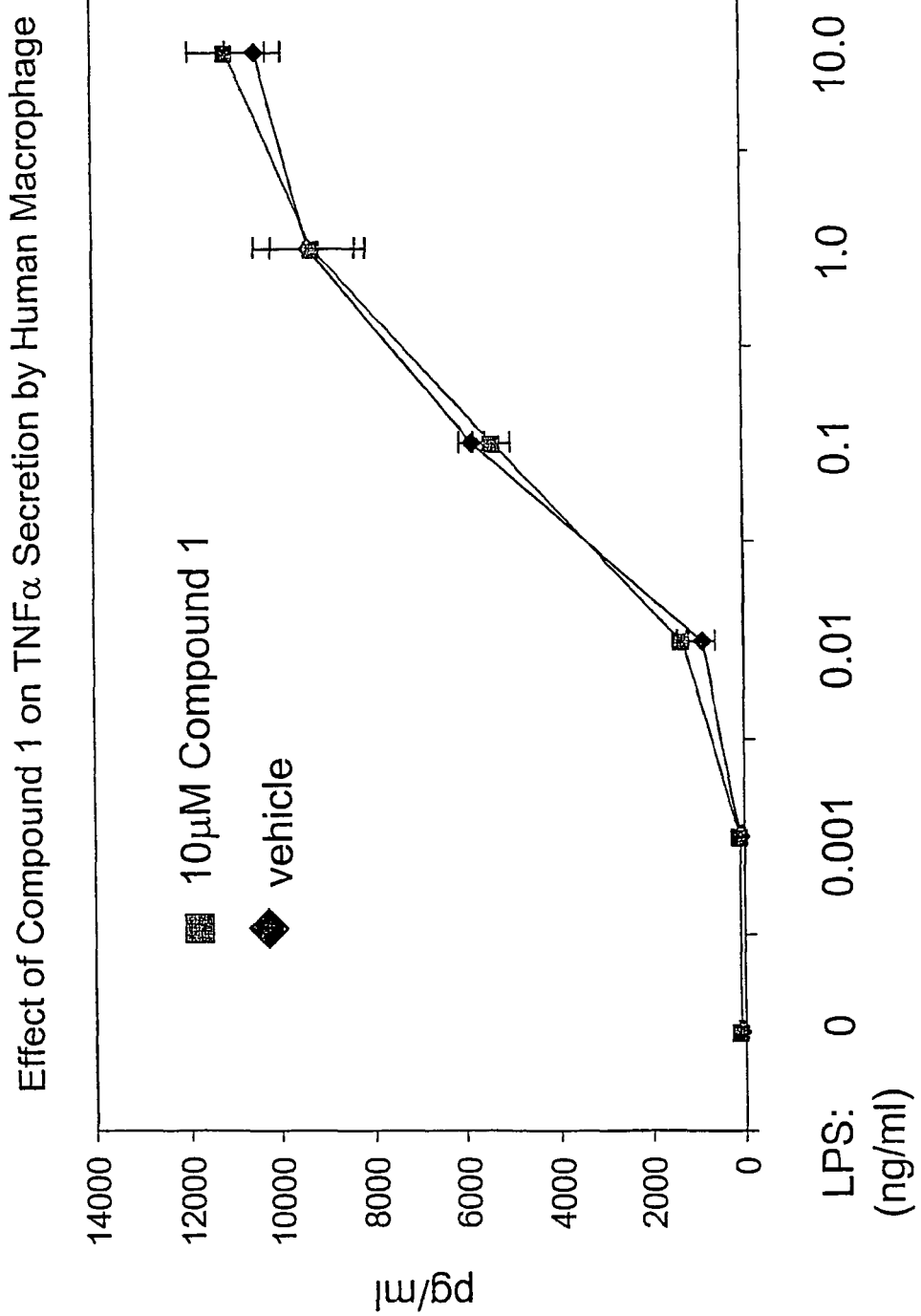

Compound 1 was found to have no effect on TNFα secretion by human macrophage (FIG. 7C) under the conditions of the assay.

D. Agonist to GPR84 Does not Increase TNFα Secretion in Mouse Macrophage

The effect of Compound 1 treatment on TNFα secretion by the mouse macrophage cell line RAW in the absence or presence of LPS was assessed. RAW cells were cultured to subconfluency. Cells were treated with vehicle or 1 µM Compound 1 for 24 hours. Vehicle was dimethyl sulfoxide (DMSO); the final concentration of DMSO in the culture was 0.1% (v/v). Cells were then stimulated with the indicated concentrations of LPS for 24 hours. Supernatants were collected and TNFα levels were assayed using a mouse specific TNFα ELISA kit from Biosource.

Figure 7D:
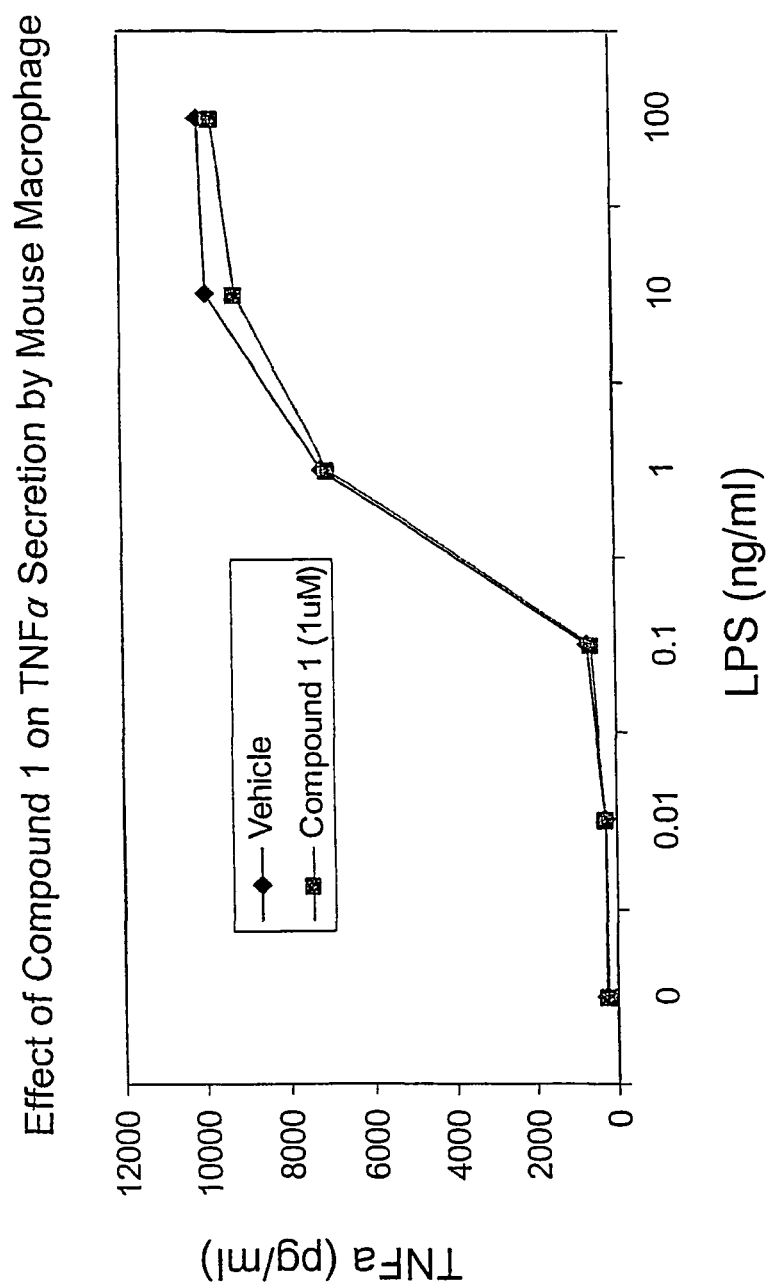

Compound 1 was found to have no effect on TNFα secretion by mouse macrophage cell line RAW (FIG. 7D) under the conditions of the assay.

Example 16

In Vivo Effects of a GPR84 Agonist on Atherogenesis in Mice

Male apoE$^{-/-}$ mice (Jackson Laboratory, Bar Harbor, Me.) are fed a normal chow. The apolipoprotein E-deficient (apoE$^{-/-}$) mouse is an established animal model of atherosclerosis, developing extensive atherosclerotic lesions on a chow diet [Zhang et al, Science (1992) 258:468-471]. At the age of 12 weeks, an agonist of GPR84 having agonist activity at mouse GPR84 or vehicle alone is injected daily into the tail vein. A preferred dose of the GPR84 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

The mice are anesthetized with an intraperitoneal injection of pentobarbital (50 mg/kg), and the hearts, which contain the aoritic sinus and aortic arch, are harvested 14 days after the injection of the GPR84 agonist. Hearts are also harvested from uninjected mice at the start of the experiment. Ten mice are used for each of the three experimental groups.

The frozen cross-sections (10 µM thick) of aortic sinus embedded in Optimal Cutting Temperature (OCT; Sakura Finetechnical Co., Ltd) compound after overnight fixation in 10% formalin are mounted on slides. For the analysis of plaque size, 3 sections (100 µM apart) from each mouse were stained with Oil Red O. The lesion size and the diameter of lipid droplets in the lesions are quantified with an image analyzing computer software, and the mean values are determined. The mean value for the group injection with the GPR84 agonist is compared with the mean value for the group injected with vehicle alone.

Data are presented as means±SEM and are analyzed by Student's t test or the Mann-Whitney U test, depending on their distribution pattern. A value of P<0.05 is considered statistically significant. See, e.g., Okamoto et al, Circulation (2002) 106:2767-2770.

These results can demonstrate that the GPR84 agonist is an inhibitor of atherogenesis.

It is expressly contemplated that in other embodiment a GPR84 agonist can be shown to be an inhibitor of atherogenesis in the ApoE$^{-/-}$ mice using a non-invasive in vivo technique [see, Fayad et al, Circulation (1998) 98:1541-1547]. It is expressly contemplated that in other embodiment, administration of the agonist is other than intravenous, for example that administration of the agonist is intraperitoneal or oral. It is expressly contemplated that in other embodiment, treatment begins other than at 12 weeks of age, either earlier or later than at 12 weeks of age. It is expressly contemplated that in other embodiment treatment continues for less than or more than 14 days. It is expressly contemplated that injection may be other than daily.

Example 17

In Vivo Effects of a GPR84 Agonist on Chronic Inflammatory Arthritis in Mice

Both male and female MRL-lpr mice (Jackson Laboratory, Bar Harbor, Me.) are used at 13-14 weeks of age. MRL-lpr mice spontaneously develop a chronic inflammatory arthritis with similar characteristics to human rheumatoid arthritis including cell infiltration, pannus formation, bone and cartilage breakdown, and the presence of serum rheumatoid factor. The disease normally develops towards the end of the animal's life span; however, injection with complete Freund's adjuvant (CFA) initiates early onset and increases the severity of arthritis [Rakay et al, J Immunol (1993) 151:5081-5087].

On Day 0 of each experiment, all groups of mice are injected with CFA intradermally into a thoracic and an inguinal site with 0.05 ml CFA supplemented to 10 mg/ml with heat inactivated *Mycobacterium tuberculosis* H37 Ra (Difco, Detroit, Mich.). Immediately, an agonist of GPR84 having agonist activity at mouse GPR84 or vehicle alone is injected daily into the tail vein. A preferred dose of the GPR84 agonist is 0.1-100 mg/kg. Other preferred dose is selected from the group consisting of 0.1 mg/kg, 0.3 mg/kg, 1.0 mg/kg, 3.0 mg/kg, 10 mg/kg, 30 mg/kg and 100 mg/kg.

Treatment is continued for 30 days. For quantifying swelling, ankle widths are measured with a micrometer. The statistical comparison of paired sets of ankle width measurements is carried out using the Student's t test.

Histopathological Analysis

At day 30 after CFA priming, the hind paws are fixed in buffered formalin. After decalcification in 10% formic acid for 48 hours, the tissues are processed for paraffin embedding. Serial sections of the tarso-metatarsal joints are cut to a thickness of 5 mm and stained with hematoxylin and eosin. Sections are examined by an individual without knowledge of the experimental protocol. A minimum of 10 sections/joint are assessed and scored to provide a semiquantitative measure of subsynovial inflammation (0, normal; 1 focal inflammatory infiltrates; 2, inflammatory infiltrate that dominates the cellular histology), synovial hyperplasia (0, normal; 1, a continuous, minimum three-layer thick, synovial lining seen in one joint; 2, minimum three-layer thick, synovial lining detected in several joints), pannus formation and cartilage erosion (0, normal; 1, pannus partially covered cartilage surfaces without evident cartilage loss; 2, pannus connected to evident cartilage loss), bone destruction (0, normal; 1, detectable destruction of bone by the pannus or osteoclast activity; 2, the pannus or osteoclast activity has destroyed a significant part of the bone), and finally, overall pathology is the overall assessment derived by the summation of the values for these criteria [see, e.g., Gong et al, J Exp Med (1997) 186:131-137]. Statistical analysis of the histopathology indices is done using the Student's t test.

These results can demonstrate that the GPR84 agonist is an inhibitor of a chronic inflammatory arthritis, for example that the GPR84 agonist is an inhibitor of rheumatoid arthritis.

It is expressly contemplated that in other embodiment, administration of the agonist is other than intravenous, for example that administration of the agonist is intraperitoneal or oral. It is expressly contemplated that in other embodiment, treatment begins other than at 13-14 weeks of age, either earlier or later than at 13-14 weeks of age. It is expressly contemplated that in other embodiment treatment continues for less than or more than 30 days. It is expressly contemplated that injection may be other than daily.

Example 18

Yeast Reporter Assay for GPR84 Agonist Activity

The yeast cell-based reporter assays have previously been described in the literature (e.g., see Miret et al, J Biol Chem (2002) 277:6881-6887; Campbell et al, Bioorg Med Chem Lett (1999) 9:2413-2418; King et al, Science (1990) 250:121-123; WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Step 3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic readout.

Yeast cells are transformed by an adaptation of the lithium acetate method described by Agatep et al (Agatep et al, 1998, Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 µg), 2 µg of each of two Fus1p-LacZ reporter plasmids (one with URA selection marker and one with TRP), 2 µg of GPR84 (e.g., human receptor) in yeast expression vector (2 µg origin of replication) and a lithium acetate/polyethylene glycol/TE buffer is pipetted into an Eppendorf tube. The yeast expression plasmid containing the receptor/no receptor control has a LEU marker. Yeast cells are inoculated into this mixture and the reaction proceeds at 30° C. for 60 min. The yeast cells are then heat-shocked at 42° C. for 15 min. The cells are then washed and spread on selection plates. The selection plates are synthetic defined yeast media minus LEU, URA and TRP (SD-LUT). After incubating at 30° C. for 2-3 days, colonies that grow on the selection plates are then tested in the LacZ assay.

In order to perform fluorimetric enzyme assays for β-galactosidase, yeast cells carrying the subject GPR84 receptor are grown overnight in liquid SD-LUT medium to an unsaturated concentration (i.e. the cells are still dividing and have not yet reached stationary phase). They are diluted in fresh medium to an optimal assay concentration and 90 µl of yeast cells are added to 96-well black polystyrene plates (Costar). Test compounds, dissolved in DMSO and diluted in a 10% DMSO solution to 10× concentration, are added to the plates and the plates placed at 30° C. for 4 h. After 4 h, the substrate for the β-galactosidase is added to each well. In these experiments, Fluorescein di(β-D-galactopyranoside) is used (FDG), a substrate for the enzyme that releases fluorescein, allowing a fluorimetric read-out. 20 µl per well of 500 µM FDG/2.5% Triton X100 is added (the detergent is necessary to render the cells permeable). After incubation of the cells with the substrate for 60 min, 20 µl per well of 1M sodium carbonate is added to terminate the reaction and enhance the fluorescent signal. The plates are then read in a fluorimeter at 485/535 nm.

An increase in fluorescent signal in GPR84-transformed yeast cells over that in yeast cells transformed with empty vector is indicative of a test compound being a compound that stimulates GPR84 receptor functionality. In certain embodiments, compounds of the invention give an increase in fluorescent signal above that of the background signal (the signal obtained in the presence of vehicle alone).

Example 19

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

In other aspect, a test compound can be radiolabeled and shown to be a ligand of a subject GPCR of the invention by evaluating its ability to bind to a cell comprising the subject GPCR or to membrane comprising the subject GPCR.

A level of specific binding of the radiolabeled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvester followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabeled known ligand.

What is claimed is:

1. A method of screening for a compound that reduces atherogenesis, comprising:
   (a) contacting a candidate compound with a G protein-coupled receptor (GPCR) comprising an amino acid sequence having at least 80% identity to SEQ ID NO:2, wherein said GPCR is present on a cell or isolated membrane thereof and wherein activation of said GPCR decreases steady state MCP-1 mRNA levels in macrophage;
   (b) identifying an agonist of said GPCR, wherein said identifying comprises assaying said candidate compound to determine whether the candidate compound stimulates said GPCR; and
   (c) administering said agonist to a mammal and examining an artery of said mammal, thereby identifying a compound that reduces atherogenesis.

2. The method of claim 1, wherein said identifying step (b) comprises contacting said candidate compound with a macrophage and determining if said candidate compound modulates ATP-binding cassette transporter 1 (ABCA1) expression.

3. The method of claim 1, wherein said identifying step (b) comprises contacting said candidate compound with a macrophage and determining if said compound modulates monocyte chemoattractant protein-1 (MCP-1) expression.

4. The method of claim 1, wherein said method further comprises determining if said agonist can treat or prevent, coronary artery disease, myocardial infarction, peripheral artery disease or ischemic stroke.

5. The method of claim 1, wherein said identifying step (b) comprises measuring a secondary messenger.

6. The method of claim 1, wherein said identifying step (b) comprises measuring expression of a reporter.

7. The method of claim 1, wherein said GPCR comprises an amino acid sequence having at least 95% identity to SEQ ID NO:2.

8. The method of claim 1, wherein said GPCR is recombinant.

9. The method of claim 1, wherein said method further comprises admixing said agonist with a pharmaceutically acceptable carrier to produce a pharmaceutical composition.

10. The method of claim 9, wherein said method further comprises administering said pharmaceutical composition to a mammal having an atherosclerotic disease.

* * * * *